(12) United States Patent
Sekine et al.

(10) Patent No.: US 7,135,579 B2
(45) Date of Patent: Nov. 14, 2006

(54) DIBENZOTHIOPHENE OXIDE COMPOUND, AND PROCESS FOR PRODUCING THE SAME

(75) Inventors: Chizu Sekine, Tsukuba (JP); Masamitsu Ishitobi, Tsukuba (JP); Koichi Fujisawa, Tsukuba (JP); Kazunori Iwakura, Ibaraki (JP); Masayoshi Minai, Moriyama (JP)

(73) Assignee: Sumitomo Chemical Company, Limited, Osaka (JP)

( * ) Notice: Subject to any disclaimer, the term of this patent is extended or adjusted under 35 U.S.C. 154(b) by 118 days.

(21) Appl. No.: 10/873,211

(22) Filed: Jun. 23, 2004

(65) Prior Publication Data

US 2004/0232384 A1  Nov. 25, 2004

Related U.S. Application Data

(62) Division of application No. 10/067,871, filed on Feb. 8, 2002, now Pat. No. 6,849,202.

(30) Foreign Application Priority Data

| Feb. 9, 2001 | (JP) | ............................. 2001-33782 |
| Feb. 14, 2001 | (JP) | ............................. 2001-37311 |
| Feb. 27, 2001 | (JP) | ............................. 2001-52954 |

(51) Int. Cl.
*C07D 333/76* (2006.01)

(52) U.S. Cl. .............................. 549/46; 549/29; 549/41; 549/43

(58) Field of Classification Search ................. 549/29, 549/41, 43, 46
See application file for complete search history.

(56) References Cited

U.S. PATENT DOCUMENTS

| 4,018,780 A | * | 4/1977 | Lappi et al. | .................... 546/62 |
| 4,965,284 A | * | 10/1990 | Nair et al. | .................... 514/443 |
| 6,849,202 B1 | * | 2/2005 | Sekine et al. | .......... 252/299.01 |

FOREIGN PATENT DOCUMENTS

| EP | 0776958 A1 | 6/1997 |
| EP | 1020510 A1 | 7/2000 |
| JP | 2-83340 A | 3/1990 |
| JP | 9-216841 A | 8/1997 |
| JP | 11-80090 A | 3/1999 |
| JP | 11-116534 A | 4/1999 |

OTHER PUBLICATIONS

Eberson et al., Acta Chemica Scandinavica, vol. 51, No. 4, pp. 492-500, (1997).
Miltsov et al., Organohalogen Compounds, vol. 19, pp. 133-135, (1994).
Jones et al., Phosphorus and Sulfur, vol. 35, No. 1-2, pp. 67-70, (1988).
Chambers et al., Tetrahedron, vol. 24, No. 10, pp. 3997-4005, (1968).
Gerdil et al., J. Am. Chem. Soc., vol. 88, No. 4, pp. 733-737, (1966).
Sekine et al., Liquid Crystals, vol. 29, No. 3, pp. 355-367, (2002).
Wu et al., Japanese Journal of Applied Physics, Part 2: Letters, vol. 38, No. 3B, pp. L286-L288, (1999); Chemical Abstracts, Abstract No. 130:359572.
Zhou et al., J. Am. Chem. Soc., vol. 117, No. 26, pp. 7017-7018, (1995); Chemical Abstracts, Abstract No. 123:245685.
Kumar, S., Journal of the Chemical Society, Perkins Transactions 1, No. 9, pp. 1018-1023, (2001); Chemical Abstracts, Abstract No. 135:166746.
Wu et al., Applied Physics Letters, vol. 74, No. 3, pp. 344-346, (1999); Chemical Abstracts, Abstract No. 130:216217.
Sinkkonen et al., Int., J. Environ. Anal. Chem., vol. 50, No. 2, pp. 117-128, (1993); Chemical Abstracts, Abstract No. 120:217148.

* cited by examiner

*Primary Examiner*—Golam M. M. Shameem
(74) *Attorney, Agent, or Firm*—Birch, Stewart, Kolasch & Birch, LLP

(57) ABSTRACT

There are disclosed novel compounds, liquid crystal compositions, polymers, optically anisotropic producgs, and optical or liquid crystal elements that have large refractive index anisotropy, mix easily with other liquid crystals, have advantageous stability against light, and exhibit absorption at practically short wavelength in the ultraviolet region. The compounds are represented by the formula (1) and have a phenylacetylene structure, wherein difference $\Delta E$ in energy of HOMO of parts (1-1), (1-2) and (1-3) calculated by the method of molecular orbitals is not less than 0.3 electronvolt, and the polarizability anisotropy $\Delta \alpha$ of a molecule represented by the formula (1) calculated in the same way is not lower than 500 A.U.:

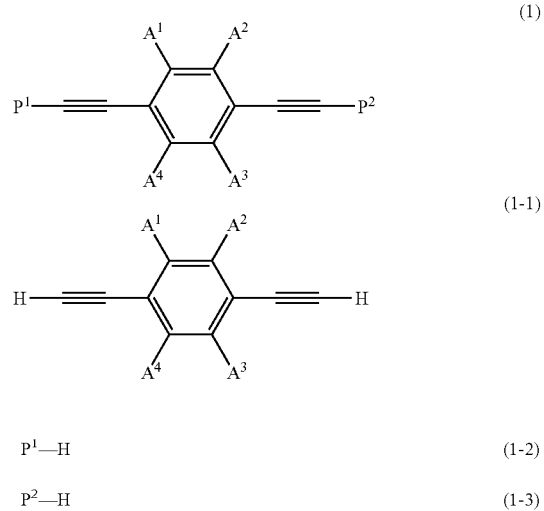

($A^1$ to $A^4$: H, F, alkyl or alkoxy group of C1 to C10 optionally substituted with F; $P^1$, $P^2$: structure fulfilling the conditions of HOMO energy and polarizability).

9 Claims, No Drawings

DIBENZOTHIOPHENE OXIDE COMPOUND, AND PROCESS FOR PRODUCING THE SAME

This application is a Divisional of application Ser. No. 10/067,871, filed on Feb. 8, 2002, now U.S. Pat. No. 6,849,202 and for which priority is claimed under 35 U.S.C. § 120; and this application claims priority of Application Nos. 2001-33782, 2001-37311 and 2001-52954 filed in Japan on Feb. 9, 2001, Feb. 14, 2001 and Feb. 27, 2001, respectively, under 35 U.S.C. § 119; the entire contents of all are hereby incorporated by reference.

FIELD OF ART

The present invention relates to novel compounds having a phenylacetylene structure, that are useful as optical, display, and recording materials, as optical compensators, polarizer materials, reflector plates, scattering plates, brightness enhancement films, and films having coloring effect, all for liquid crystal devices, and as a component of liquid crystal materials for liquid crystal display elements. The present invention also relates to liquid crystal compositions, polymers, optically anisotropic products, optical or liquid crystal elements, novel dibenzothiophene compounds that may be used for production of the compounds having a phenylacetylene structure, intermediates thereof, and process for producing the same.

BACKGROUND ART

Improvement in performance of liquid crystal display elements has become an essential issue with the recent development in information-oriented society. For higher processing speed and performance, liquid crystal compositions must contain a component having large refractive index anisotropy.

Tolan compounds are known as liquid crystal having relatively large refractive index anisotropy (Mol. Cryst. Liq. Cryst., Vol. 23, p233 (1973)). However, the refractive index anisotropy of this compound is about 0.2, which is not yet large enough.

There have also been developed compounds represented by the following formulae and disclosed in JP-2-83340-A and JP-9-216841-A:

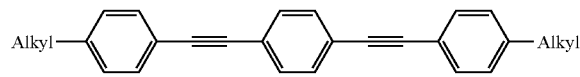

(wherein "Alkyl" stands for an alkyl group)

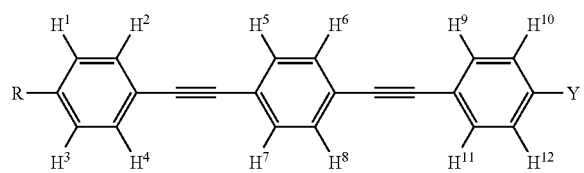

(wherein R stands for an alkyl group; Y stands for R, a fluorine, chlorine, bromine, or iodine atom, or a cyano group; $H^1$ to $H^{12}$ each stands for a hydrogen, fluorine, or chlorine atom, provided that at least one of $H^1$ to $H^{12}$ stands for a fluorine or chlorine atom).

The refractive index anisotropy of these compounds is larger than that of the tolan compounds, but is yet as small as about 0.4. In the second compound, when the hydrogen atoms are substituted with halogen atoms such as fluorine atoms for improved compatibility, the refractive index anisotropy becomes still smaller, e.g. about 0.3. Under such circumstances, development of liquid crystalline compounds with larger refractive index anisotropy is demanded.

However, if the improvement in refractive index anisotropy is sought by extending the conjugated pi-electron systems in such compounds, peaks of the absorption spectrum of the compounds in the ultraviolet and visible regions shift to the longer wavelength side, sometimes resulting in undesirable coloring of the compound.

There have been discussed possible application of liquid crystalline materials not only to a switching element of displays for switching the display modes such as TN or STN mode, but also to retarders, polarizers, polarizing prisms, beam splitters, reflectors, holographic elements, color separators, or various optical filters, which make use of the optical anisotropy of the materials such as alignment and refractive index. Improvement in performance of display elements has also become an essential issue with the recent development of the information-oriented society.

As techniques for production of optically anisotropic products from such liquid crystalline materials, there are known, for example, methods of photopolymerizing a liquid crystalline compound having a polymerizable functional group, or a polymerizable liquid crystal composition containing such a compound, by irradiating the compound or the composition in a liquid crystal state with ultraviolet or visible irradiation. These methods intend, in other words, to produce polymers wherein the liquid crystal molecules aligned in the liquid crystal state are semipermanently fixed for achieving stable optical functions.

Recently known liquid crystalline compounds having a polymerizable functional group are disclosed in JP-A-11-116534 and JP-A-11-80090, the former proposing mainly a compound having a phenylbenzoate core, and the latter a compound having a core including phenylbenzoate, cyclohexylphenyl, and tolan. Neither of the compounds, however, has a core exhibiting particularly large refractive index anisotropy ($\Delta n$).

It is known that a substituent may be introduced into a dibenzothiophene compound through a process disclosed in J. Am. Chem. Soc., 1948, 70, 1748, or in Heterocyclic Chem., 1985, 22, 215. However, by these processes, it is hard to introduce two highly reactive substituents selectively into the 3- and 7-positions of a dibenzothiophene compound.

DISCLOSURE OF THE INVENTION

It is therefore an object of the present invention to provide novel compounds having a phenylacetylene structure that have large refractive index anisotropy, mix easily with other liquid crystals, have advantageous stability against light, and exhibit absorption at wavelength in the ultraviolet region that is short enough for practical use.

It is another object of the present invention to provide, utilizing the above-mentioned novel compounds having a phenylacetylene structure, polymers, liquid crystal compositions, optically anisotropic products, and optical or liquid crystal elements, which are useful in manufacturing optical compensators for liquid crystal devices, polarizer materials, reflectors, scattering plates, and films having coloring effect.

It is still another object of the present invention to provide novel dibenzothiophene compounds having two reactive substituents at 3- and 7-positions, which are useful as optically functional materials, and also useful, for example, in manufacture of the novel compounds having a phenylacetylene structure, as well as to provide intermediates of the dibenzothiophene compounds, and methods for highly selectively producing such compounds or intermediates.

The present inventors have made intensive studies for achieving the above objects to find that a certain kind of phenylacetylene compounds has sufficiently large refractive index anisotropy, exhibits absorption at practically short wavelength in the ultraviolet region of the absorption spectrum, and thus achieve the above objects, thereby completing the present invention.

According to the present invention, there is provided a compound represented by the formula (1) having a phenylacetylene structure, wherein difference ΔE in energy of the highest occupied molecular orbital (HOMO) of parts in the formula (1) each represented by the formula (1-1), (1-2), or (1-3) calculated by method of molecular orbitals satisfies the following formula:

$$\Delta E = E_{1-1} - (E_{1-2} + E_{1-3})/2 \geq 0.3 \text{ electronvolt}$$

wherein $E_{1-1}$, $E_{1-2}$, and $E_{1-3}$ denote the HOMO energy of corresponding parts represented by the formulae (1-1), (1-2), and (1-3), respectively, of the formula (1) calculated by the method of molecular orbitals, and wherein polarizability anisotropy Δα of a molecule represented by the formula (1) calculated by said method is not lower than 500 atomic units:

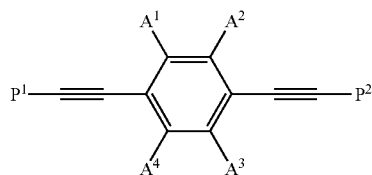
(1)

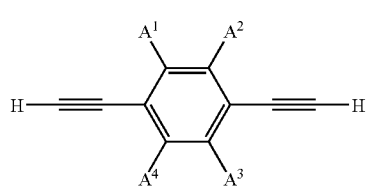
(1-1)

$P^1$—H (1-2)

$P^2$—H (1-3)

wherein $A^1$ to $A^4$ each independently stands for a hydrogen atom, a fluorine atom, or an alkyl or alkoxy group having 1 to 10 carbon atoms optionally substituted with at least one fluorine atom; and $P^1$ and $P^2$ may have any chemical structures as long as $P^1$ and $P^2$ satisfy said conditions of the HOMO energy and polarizability anisotropy.

According to the present invention, there is also provided a compound represented by the formula (2) having a phenylacetylene structure:

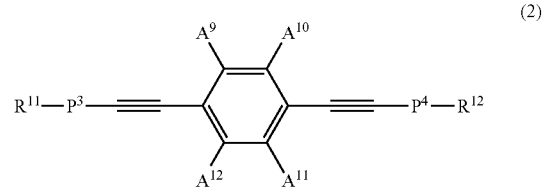
(2)

wherein $A^9$ to $A^{12}$ each independently stands for a hydrogen atom, a fluorine atom, or an alkyl or alkoxy group having 1 to 10 carbon atoms optionally substituted with at least one fluorine atom; $P^3$ and $P^4$ each stands for the formula (2-1) or (2-2), with at least one of $P^3$ and $P^4$ standing for the formula (2-1):

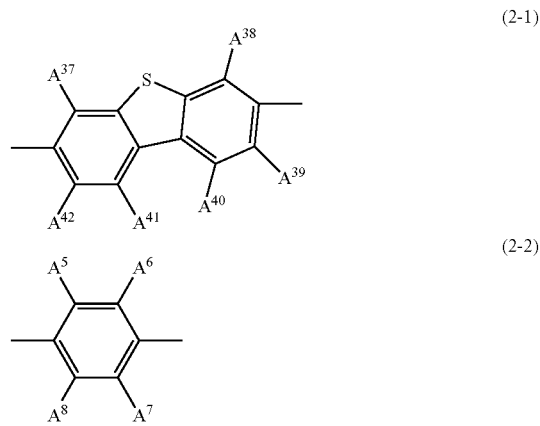
(2-1)

(2-2)

wherein $A^{37}$ to $A^{42}$ in the formula (2-1) and $A^5$ to $A^8$ in the formula (2-2) each independently stands for a hydrogen atom, a fluorine atom, or an alkyl or alkoxy group having 1 to 10 carbon atoms optionally substituted with at least one fluorine atom;

$R^{11}$ and $R^{12}$ each independently stands for a hydrogen atom, a fluorine atom, a cyano group, —$SF_5$, —NCS, a 4-$R^{23}$-(cycloalkyl) group, a 4-$R^{23}$-(cycloalkenyl) group, an $R^{24}$-(O)q group, or a group represented by the formula (3), wherein $R^{23}$ stands for a hydrogen atom or a straight or branched alkyl group having 1 to 12 carbon atoms optionally substituted with at least one fluorine atom, $R^{24}$ stands for a straight or branched alkyl group having 1 to 12 carbon atoms optionally substituted with at least one fluorine atom, or a strait or branched alkenyl or alkynyl group having 3 to 12 carbon atoms optionally substituted with at least one fluorine atom, q denotes 0 to 1,

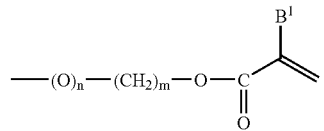
(3)

wherein n denotes 0 to 1, and m denotes an integer of 1 to 20, $B^1$ stands for a hydrogen atom or a methyl group, when both $R^{11}$ and $R^{12}$ stand for a group represented by the formula (3), n, m, and $B^1$ in one group of the formula (3) may be the same as or different from those of the other.

According to the present invention, there is provided a liquid crystal composition comprising at least one compound represented by the formula (1) or (2).

According to the present invention, there is also provided a polymer obtained by polymerization of at least one compound represented by the formula (1) wherein at least one of $P^1$ and $P^2$ has an acrylate or methacrylate group on its terminal, or by polymerization of at least one compound represented by the formula (2) wherein at least one of $R^{11}$ and $R^{12}$ stands for a group represented by the formula (3).

According to the present invention, there is further provided a polymer obtained by polymerization of the liquid crystal composition mentioned above.

According to the present invention, there is further provided a liquid crystal composition comprising:

at least one material selected from the group consisting of the above-mentioned compounds and the above-mentioned polymers, and at least one monomer other than the above-mentioned compounds selected from the group consisting of methacrylate esters, acrylate esters, epoxy, and vinyl ethers.

According to the present invention, there is also provided a polymer obtained by polymerization of this liquid crystal composition.

According to the present invention, there is also provided an optically anisotropic product produced with at least one material selected from the group consisting of the above-mentioned compounds, the above-mentioned polymers, and the above-mentioned liquid crystal compositions, as well as an optical or liquid crystal element manufactured with at least one of these materials.

According to the present invention, there is further provided a dibenzothiophene compound represented by the formula (A-1):

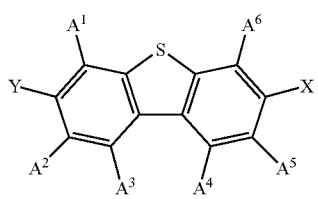

(A-1)

wherein $A^1$ to $A^6$ each independently stands for a hydrogen atom, a fluorine atom, or an alkyl or alkoxy group having 1 to 10 carbon atoms optionally substituted with at least one fluorine atom; X stands for a halogen atom; and Y stands for a halogen atom or a hydroxyl group.

According to the present invention, there is also provided a dibenzothiophene compound represented by the formula (A-2):

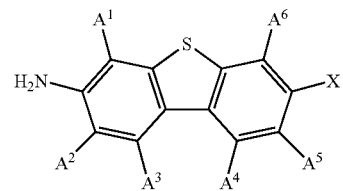

(A-2)

wherein $A^1$ to $A^6$ and X mean the same as those in the formula (A-1).

According to the present invention, there is further provided a dibenzothiophene oxide compound represented by the formula (A-3):

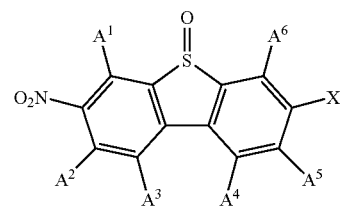

(A-3)

wherein $A^1$ to $A^6$ and X mean the same as those in the formula (A-1).

According to the present invention, there is also provided a dibenzothiophene oxide compound represented by the formula (A-4):

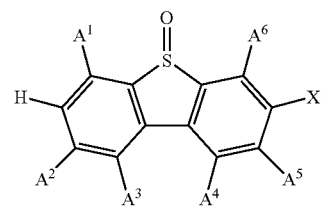

(A-4)

wherein $A^1$ to $A^6$ and X mean the same as those in the formula (A-1).

According to the present invention, there is also provided a method for producing a dibenzothiophene compound represented by the formula (A-1) comprising:

diazotizing a dibenzothiophene compound represented by the formula (A-2) to obtain a diazonium salt, and decomposing said diazonium salt in the presence of an anion corresponding to Y in the formula (A-1).

According to the present invention, there is also provided a method for producing a dibenzothiophene compound represented by the formula (A-2) comprising reducing a dibenzothiophene oxide compound represented by the formula (A-3).

According to the present invention, there is also provided a method for producing a dibenzothiophene oxide compound represented by the formula (A-3) comprising nitrating a dibenzothiophene oxide compound represented by the formula (A-4).

According to the present invention, there is also provided a method for producing a dibenzothiophene oxide compound represented by the formula (A-4) comprising oxidizing a dibenzothiophene compound represented by the formula (A-5):

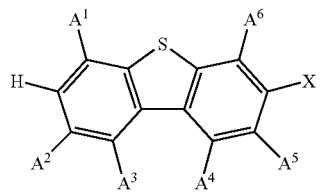

(A-5)

wherein $A^1$ to $A^6$ and X mean the same as those in the formula (A-1).

PREFERRED EMBODIMENTS OF THE INVENTION

The present invention will now be explained in detail.

The compounds having a phenylacetylene structure according to the present invention (referred to as compounds of the present invention hereinbelow) are compounds represented by the formula (1) or (2) mentioned above. $A^1$ to $A^4$ in the formula (1) and $A^9$ to $A^{12}$ in the formula (2) each independently stands for a hydrogen atom, a fluorine atom, an alkyl or alkoxy group having 1 to 10 carbon atoms optionally substituted with at least one fluorine atom. It is preferred that at least one of $A^1$ to $A^4$ and at least one of $A^9$ to $A^{12}$ stand for the alkyl or alkoxy group optionally substituted with at least one fluorine atom. In the formula (2), when all of $A^9$ to $A^{12}$ each stands for an alkyl group, the number of carbon atoms in each group is preferably not less than two.

In the formula (1), $P^1$ and $P^2$ may have any chemical structures as long as $P^1$ and $P^2$ satisfy the conditions of the HOMO energy and polarizability anisotropy mentioned above. Examples of the combination of $P^1$ and $P^2$ may include the pairs of groups corresponding to $P^1$ and $P^2$ in the compounds to be specified later.

In the formula (2), $P^3$ and $P^4$ each stands for the formula (2-1) or (2-2), and at least one of $P^3$ and $P^4$ stands for the formula (2-1). $R^{11}$ and $R^{12}$ each independently stands for a hydrogen atom, a fluorine atom, a cyano group, $—SF_5$, —NCS, 4-$R^{23}$-(cycloalkyl) group, 4-$R^{23}$-(cycloalkenyl) group, $R^{24}$-(O)q group, or a group represented by the formula (3), wherein $R^{23}$ stands for a hydrogen atom, or a straight or branched alkyl group having 1 to 12 carbon atoms optionally substituted with at least one fluorine atom, $R^{24}$ stands for a straight or branched alkyl group having 1 to 12 carbon atoms optionally substituted with at least one fluorine atom, or a straight or branched alkenyl or alkynyl group having 3 to 12 carbon atoms optionally substituted with at least one fluorine atom, and q denotes 0 or 1. In the formula (3), n denotes 0 or 1, and m denotes an integer of 1 to 20, $B^1$ stands for a hydrogen atom or a methyl group. When both $R^{11}$ and $R^{12}$ stand for a group represented by the formula (3), n, m, and $B^1$ in one group of the formula (3) may be the same as or different from those of the other. Alternatively, only one of $R^{11}$ and $R^{12}$ may stand for a group represented by the formula (3).

The compound represented by the formula (1) is a compound wherein difference $\Delta E$ in energy of the highest occupied molecular orbital (HOMO) of the parts of the formula (1) each represented by the formula (1-1), (1-2) or (1-3) calculated by the method of molecular orbitals is not less than 0.3 electronvolt, preferably not less than 0.35 electronvolt, and the polarizability anisotropy $\Delta\alpha$ of a molecule represented by the formula (1) calculated by the same method is not lower than 500 atomic units, preferably not lower than 600 atomic units.

The polarizability anisotropy $\Delta\alpha$ of a molecule is a value obtained by calculation according to the following formula, denoting the polarizability along a long axis of the molecule by $\alpha xx$, and those along the axes perpendicular to this axis by $\alpha yy$ and $\alpha zz$:

$$\Delta\alpha = \alpha xx - (\alpha yy + \alpha zz)/2$$

A long axis of a molecule may be taken in the direction in which the molecule has approximately the maximum length. In the formula (1), for example, the axis connecting the terminal carbon in the carbon-carbon triple bond bonded to $P^1$ and the terminal carbon in the carbon-carbon triple bond bonded to $P^2$, maybe the long axis of the molecule represented by the formula (1).

Examples of the compounds represented by the formulae (1) and (2) may include compounds represented by the following formulae.

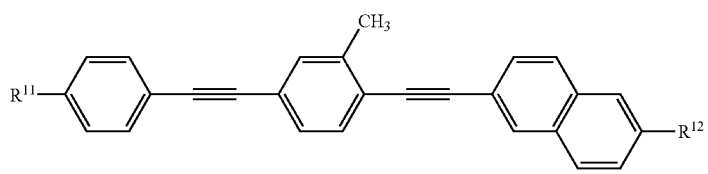

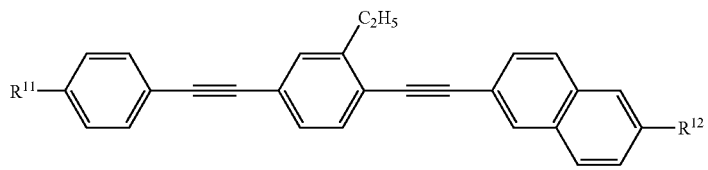

-continued
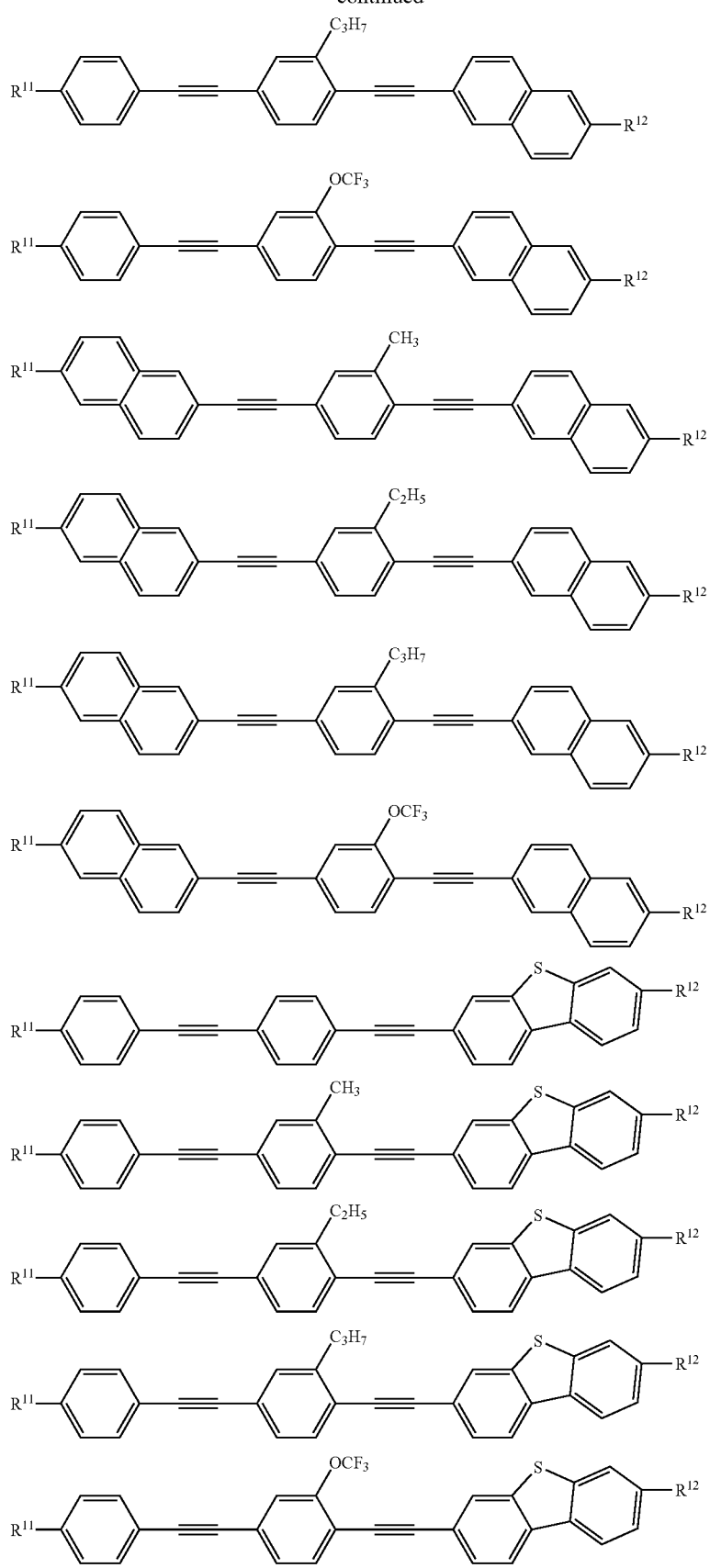

-continued
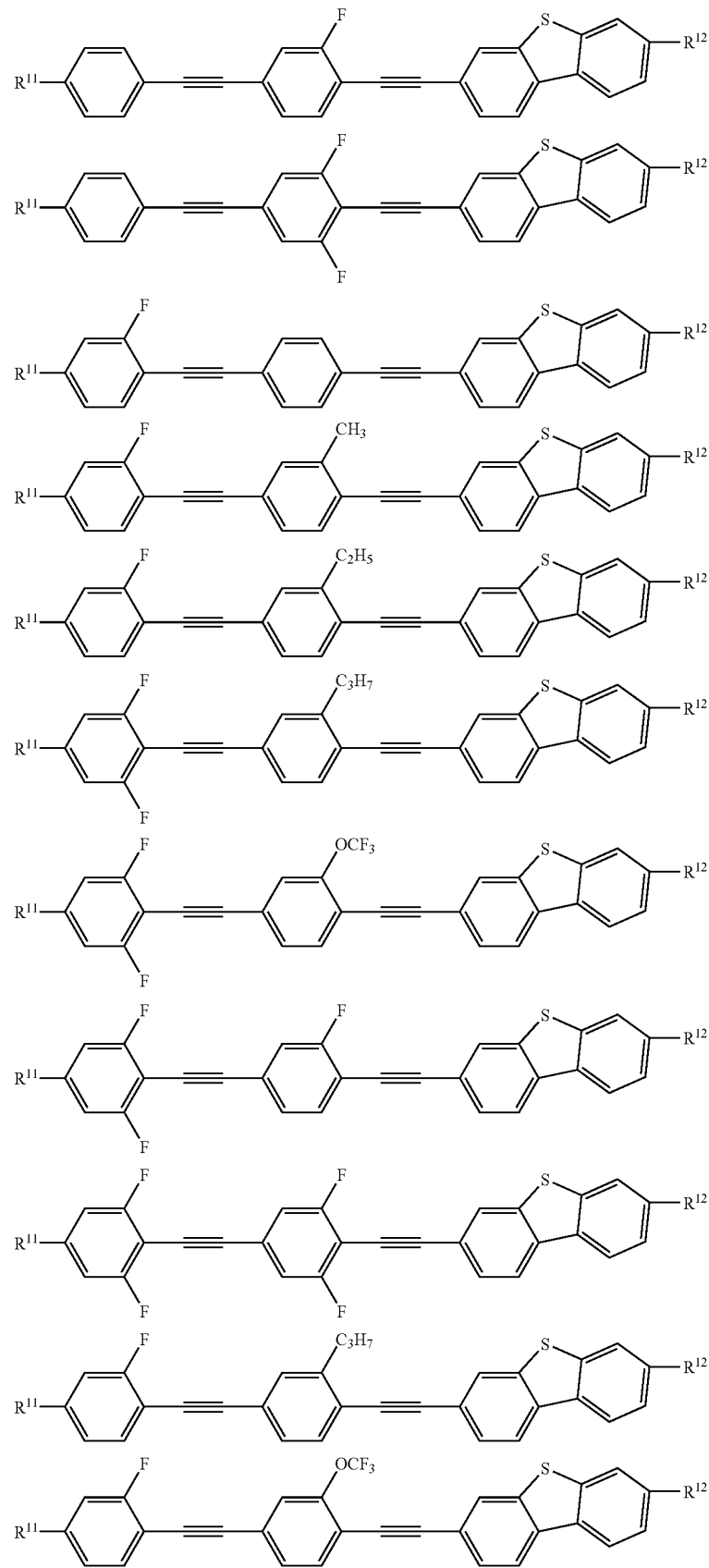

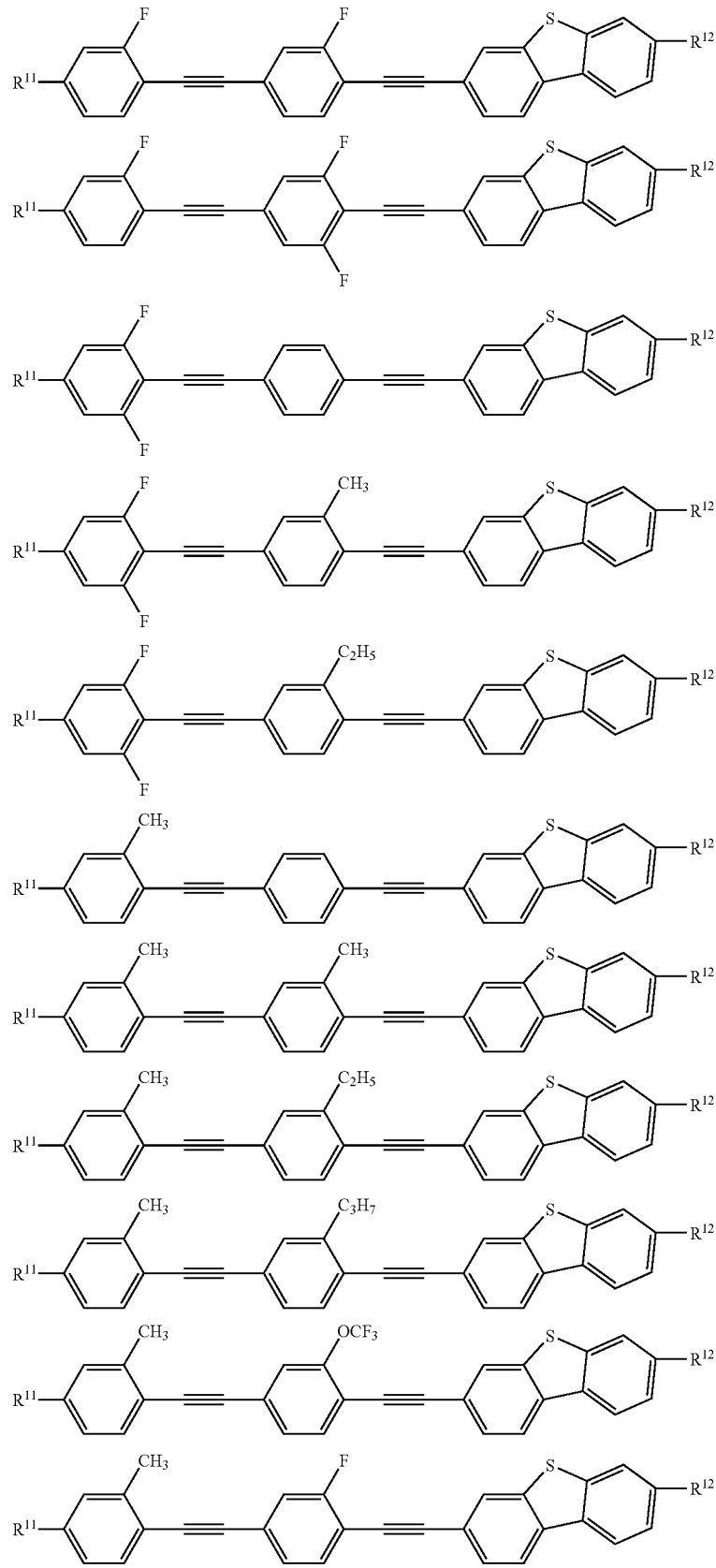

-continued

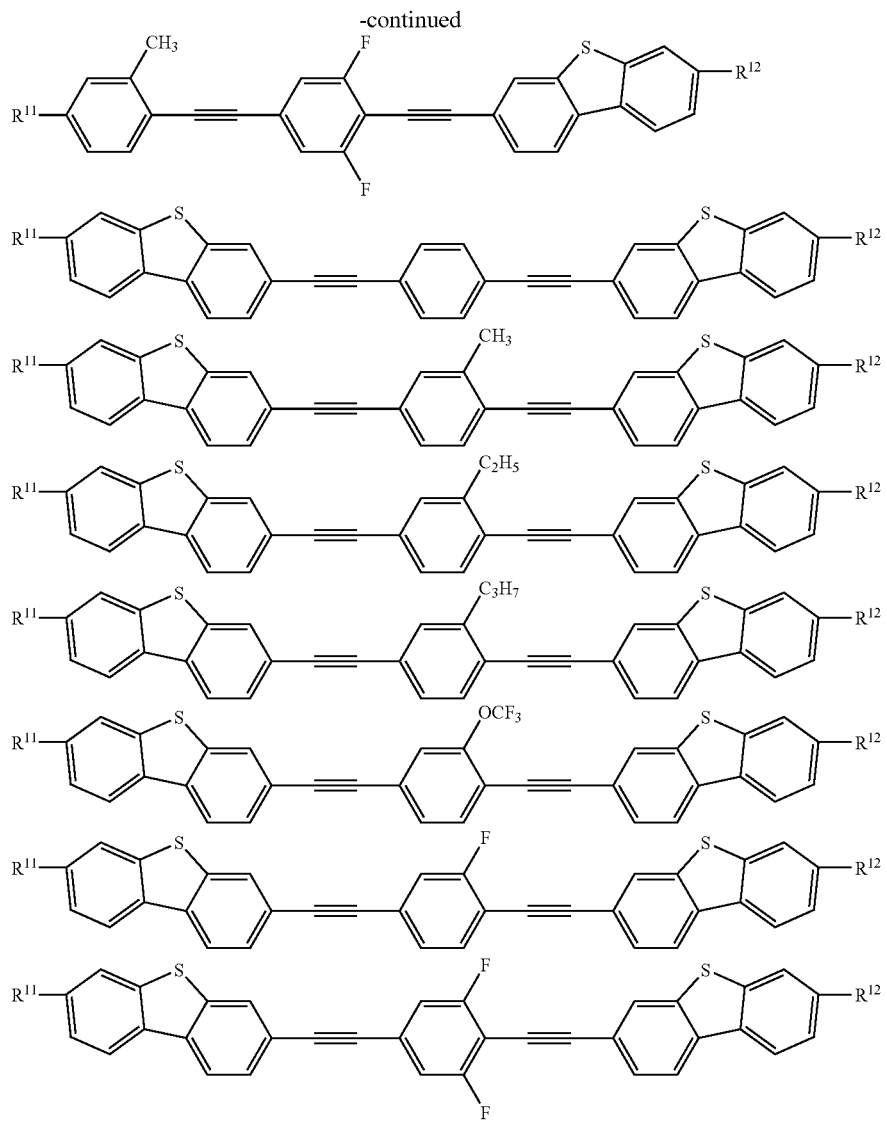

In the above formulae, $R^{11}$ and $R^{12}$ may stand for, for example, a hydrogen atom; a fluorine atom; an alkyl group such as a methyl, ethyl, propyl, butyl, pentyl, hexyl, heptyl, octyl, nonyl, decyl, undecyl, or dodecyl group, or an alkyl group substituted with at least one fluorine atom, i.e. a fluoroalkyl group such as a trifluoromethyl group; an alkenyl group such as an ethenyl, propenyl, butenyl, pentenyl, hexenyl, heptenyl, octenyl, nonenyl, decenyl, undecenyl, or dodecenyl group, or an alkenyl group substituted with at least one fluorine atom, i.e. a fluoroalkenyl group; an alkynyl group such as a propynyl, butynyl, pentynyl, hexynyl, heptynyl, octynyl, nonynyl, decynyl, or dodecynyl group, or an alkynyl group substituted with at least one fluorine atom, i.e. a fluoroalkynyl group; an alkoxy group such as a methoxy, ethoxy, propoxy, butoxy, pentyloxy, hexyloxy, octyloxy, nonyloxy, decyloxy, undecyloxy, or dodecyloxy group, or an alkoxy group substituted with at least one fluorine atom, i.e. a fluoroalkoxy group such as a methoxy group having 1 to 3 substituted fluorine atoms, or an ethoxy group having 1 to 5 substituted fluorine atoms; an alkenyloxy group such as a vinyloxy, propenyloxy, butenyloxy, pentenyloxy, hexenyloxy, heptenyloxy, octenyloxy, nonenyloxy, or decenyloxy group, or an alkenyloxy group substituted with at least one fluorine atom, i.e. a fluoroalkenyloxy group; an alkynyloxy group such as a propionyloxy, butynyloxy, pentynyloxy, hexynyloxy, heptynyloxy, octynyloxy, nonynyloxy, decynyloxy, undecynyloxy, or dodecynyloxy group, or an alkynyloxy group substituted with at least one fluorine atom, i.e. a fluoroalkynyloxy group; an alkoxyalkyl group such as a methoxymethyl, ethoxymethyl, propoxymethyl, butoxymethyl, pentyloxymethyl, hexyloxymethyl, heptyloxymethyl, octyloxymethyl, nonyloxymethyl, decyloxymethyl, methoxyethyl, ethoxyethyl, propoxyethyl, butoxyethyl, pentyloxyethyl, hexyloxyethyl, heptyloxyethyl, octyloxyethyl, nonyloxyethyl, decyloxyethyl, methoxypropyl, ethoxypropyl, propoxypropyl, butoxypropyl, pentyloxypropyl, hexyloxypropyl, heptyloxypropyl, octyloxypropyl, nonyloxypropyl, methoxybutyl, ethoxybutyl, propoxybutyl, butoxybutyl, pentyloxybutyl, hexyloxybutyl, heptyloxybutyl, octyloxybutyl, methoxypentyl, ethoxypentyl, propoxypentyl, butoxypentyl, pentyloxypentyl, hexyloxypentyl, or heptyloxypentyl group, or an alkoxyalkyl group substituted with at least one fluorine atom, i.e., a fluoroalkoxyalkyl group; a branched alkyl group such as a 2-methylpropyl, 2-methylbutyl, 3-methylbutyl, or 3-methylpentyl group, or a branched alkyl group substituted with at least one fluorine atom, i.e., a branched fluoroalkyl group; a branched alkyloxy group such as a 2-methylpropyloxy, 2-methylbutyloxy, 3-methylbutyloxy, or 3-methylpentyloxy group, or a branched alkyloxy group substituted with at least one fluorine atom, i.e., a branched fluoroalkyloxy group; a 4-alkylcycloalkyl group such as a 4-methylcyclohexyl, 4-ethylcyclohexyl, 4-propylcyclohexyl, 4-butylcyclohexyl, 4-pentylcyclohexyl, 4-hexylcyclohexyl, 4-heptylcyclohexyl, 4-octylcyclohexyl, 4-nonylcyclohexyl, or 4-decylcyclohexyl group, or a 4-alkylcycloalkyl group substituted with at least one fluorine atom, i.e., a 4-fluoroalkylcycloalkyl group; a 4-alkylcycloalkenyl group such as a 4-propylcyclohexenyl or 4-pentylcyclohexenyl group, or a 4-alkylcycloalkenyl group substituted with at least one fluorine atom, i.e., a 4-fluoroalkylcycloalkenyl group; a cyano group; —SF$_5$; —NCS; —OCH$_2$OCOCHCH$_2$, —OC$_2$H$_4$OCOCHCH$_2$, —OC$_3$H$_6$OCOCHCH$_2$, —OC$_4$H$_8$OCOCHCH$_2$, —OC$_5$H$_{10}$OCOCHCH$_2$, —OC$_6$H$_{12}$OCOCHCH$_2$, —OC$_7$H$_{14}$OCOCHCH$_2$, —OC$_8$H$_{16}$OCOCHCH$_2$, —OC$_9$H$_{18}$OCOCHCH$_2$, —OC$_{10}$H$_{20}$OCOCHCH$_2$; —OCH$_2$OCOC(CH$_3$)CH$_2$, —OC$_2$H$_4$OCOC(CH$_3$)CH$_2$, —OC$_3$H$_6$OCOC(CH$_3$)CH$_2$, —OC$_4$H$_8$OCOC(CH$_3$)CH$_2$, —OC$_5$H$_{10}$OCOC(CH$_3$)CH$_2$, —OC$_6$H$_{12}$OCOC(CH$_3$)CH$_2$, —OC$_7$H$_{14}$OCOC(CH$_3$)CH$_2$, —OC$_8$H$_{16}$OCOC(CH$_3$)CH$_2$, —OC$_9$H$_{18}$OCOC(CH$_3$)CH$_2$, or —OC$_{10}$H$_{20}$OCOC(CH$_3$)CH$_2$. However, $R^{11}$ and $R^{12}$ may not be limited to these examples.

The compounds of the present invention may be synthesized through ordinary organic synthesizing processes. For example, a phenylacetylene compound wherein three aryl groups are bonded together via two acetylene groups therebetween, may be synthesized by suitably combining Sonogashira reaction (Organo Copper Reagents. A Practical Approach; Taylor, R. J. K. Ed.; Oxford University Press: Oxford, 1994; Chapter 10, pp217–236. Metal-Catalyzed Cross-Coupling Reactions; Diederich, F., Stang, P. J. Eds; Wiley: Weinheim, 1997; Chapter 5, pp203–229), using suitable starting materials, such as by palladium-catalyzed coupling reaction of an aromatic halide or a sulfonate of aromatic alcohol such as trifluoromethanesulfonate with the methine part of an acetylene terminal of an acetylene compound in the presence of a base.

The liquid crystal composition of the present invention contains at least one compound of the present invention as a component. Other components of the composition are not particularly limited, but are preferably compounds or compositions exhibiting a liquid crystal phase.

Such other components of the liquid crystal composition of the present invention may include, for example, at least one liquid crystalline compound represented by any of the formulae (4) to (7). These liquid crystalline compounds may be synthesized through ordinary organic synthesizing processes.

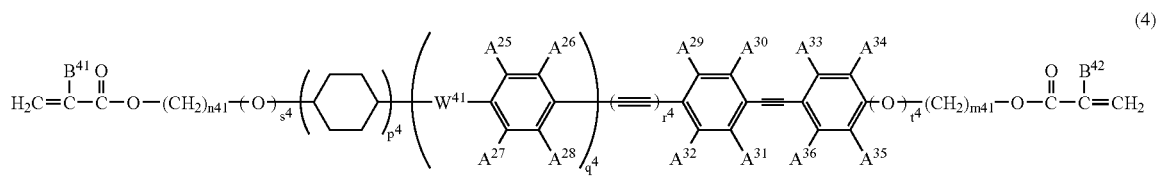

(4)

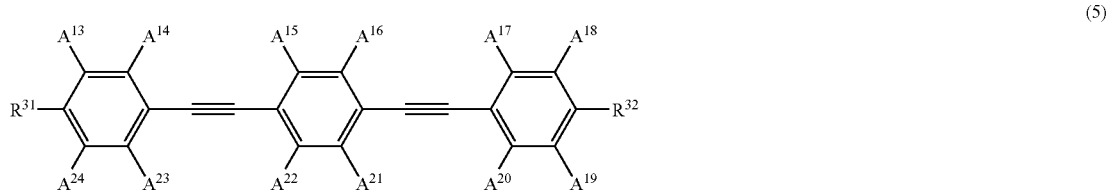

(5)

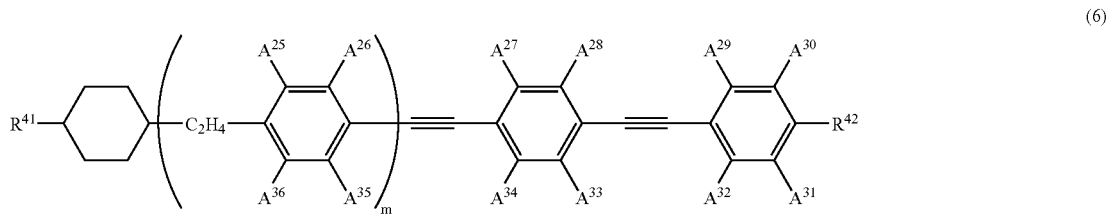

(6)

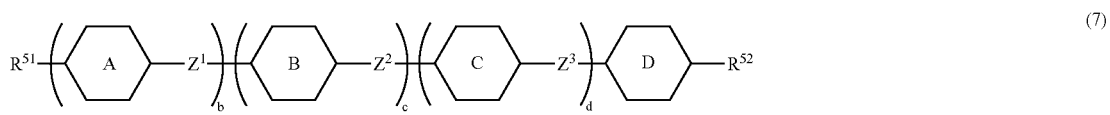

(7)

In the formula (4), $A^{25}$ to $A^{36}$ each independently stands for a hydrogen atom, a fluorine atom, an alkyl or alkoxy group having 1 to 10 carbon atoms optionally substituted with at least one fluorine atom. $B^{41}$ and $B^{42}$ each stands for a hydrogen atom or a methyl group. $p^4$, $q^4$, $r^4$, $s^4$, and $t^4$ each denotes 0 or 1, provided that when $q^4$ is 0, at least one of $A^{29}$ to $A^{36}$ stands for an alkyl or alkoxy group having 1 to 10 carbon atoms optionally substituted with at least one fluorine atom. $m^{41}$ and $n^{41}$ each denotes an integer of 0 to 14, provided that when $s^4$ is 1, $n^{41}$ is not 0, and that when $t^4$ is 1, $m^{41}$ is not 0. $W^{41}$ stands for a single bond, $-CH_2CH_2-$, or $-C\equiv C-$.

Examples of the compound represented by the formula (4) may include the compounds represented by the following formulae:

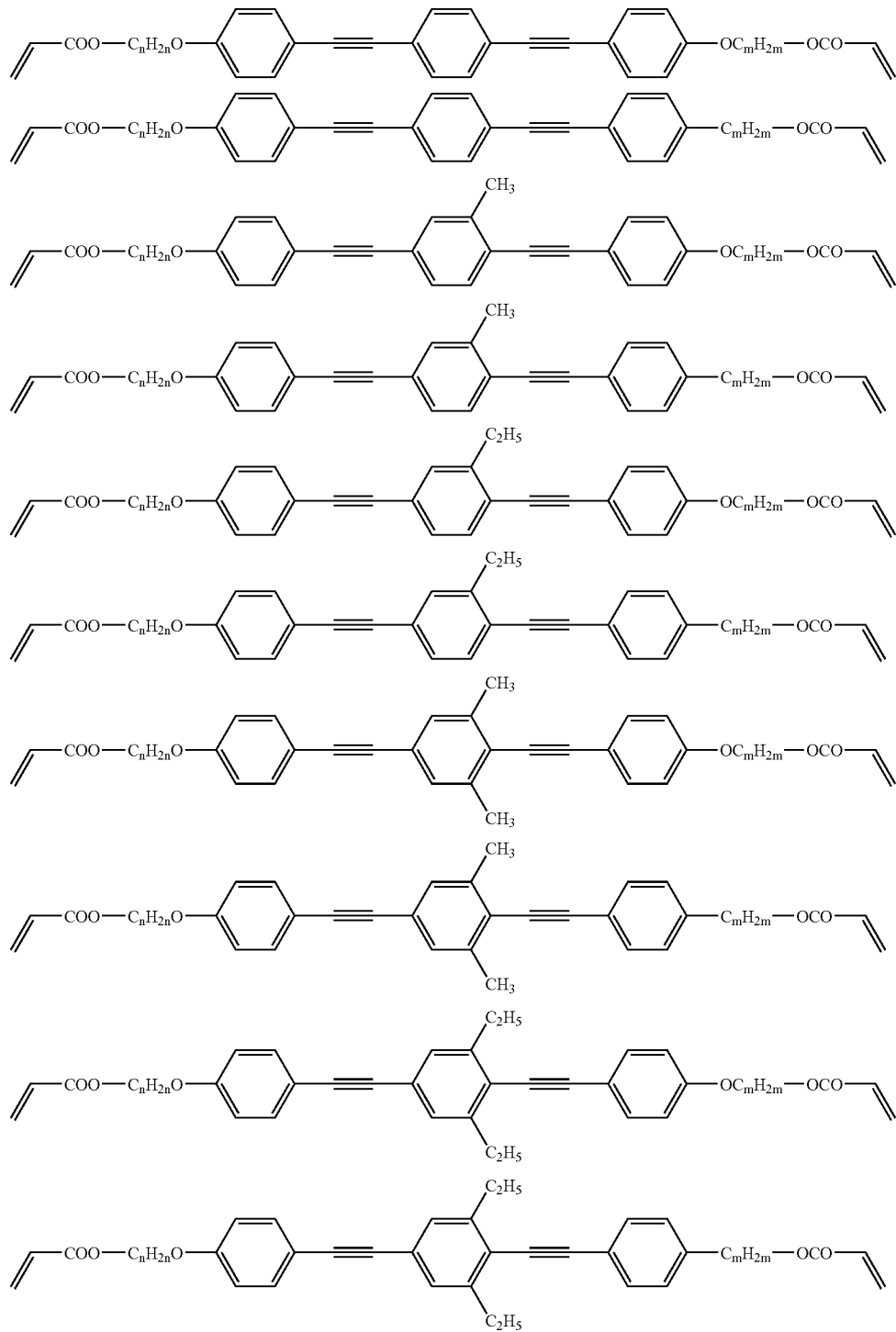

-continued
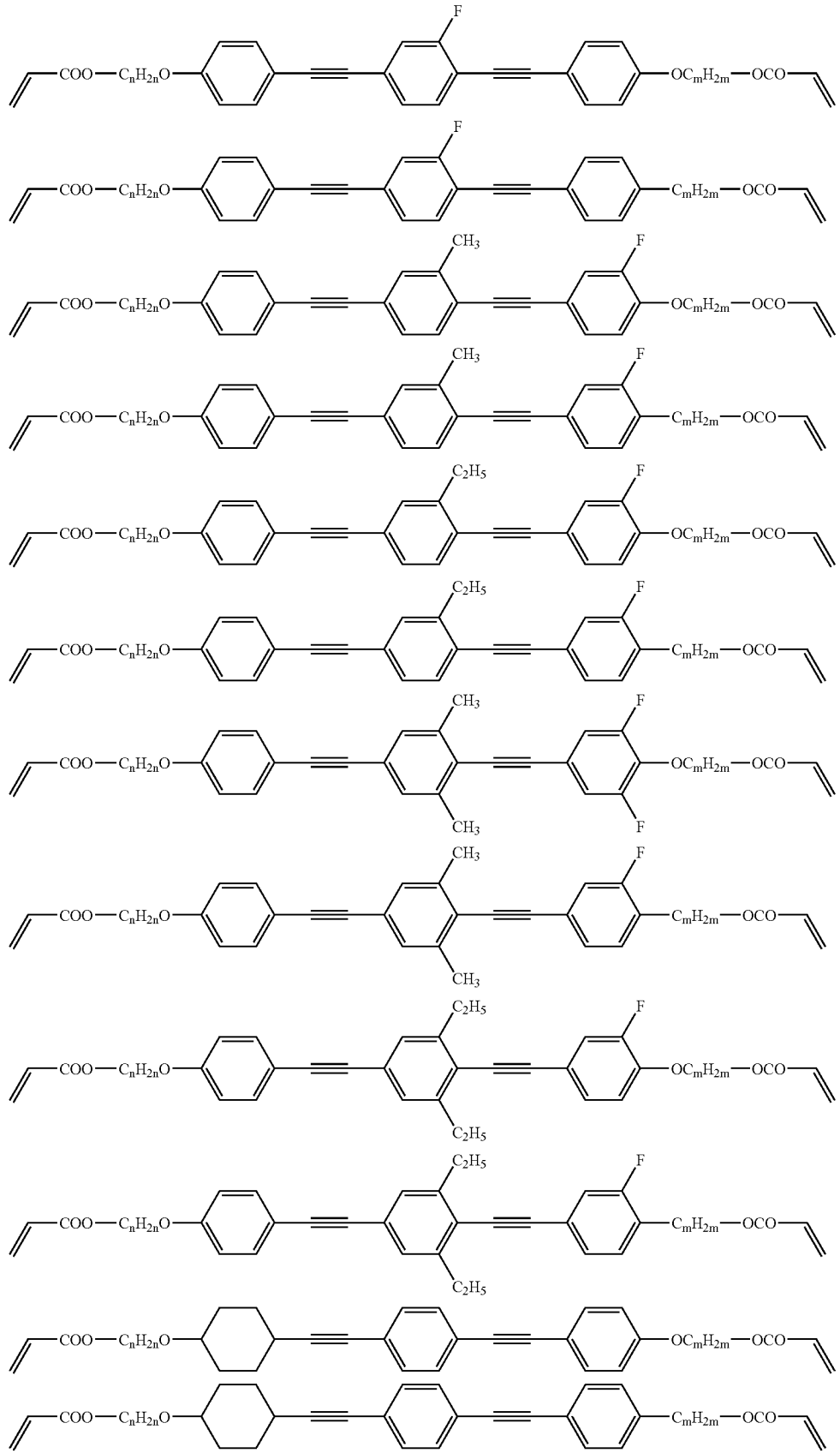

-continued
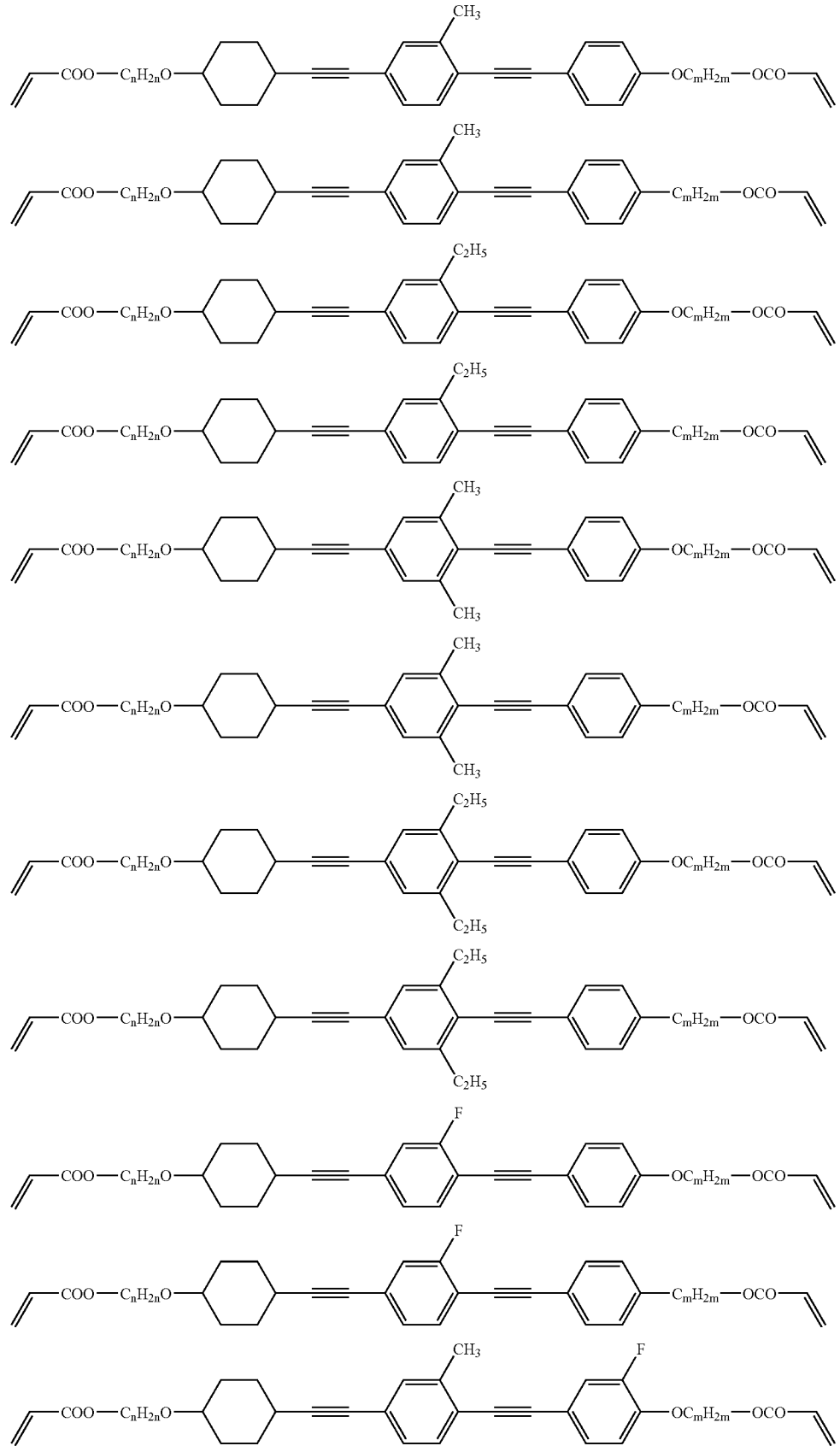

-continued
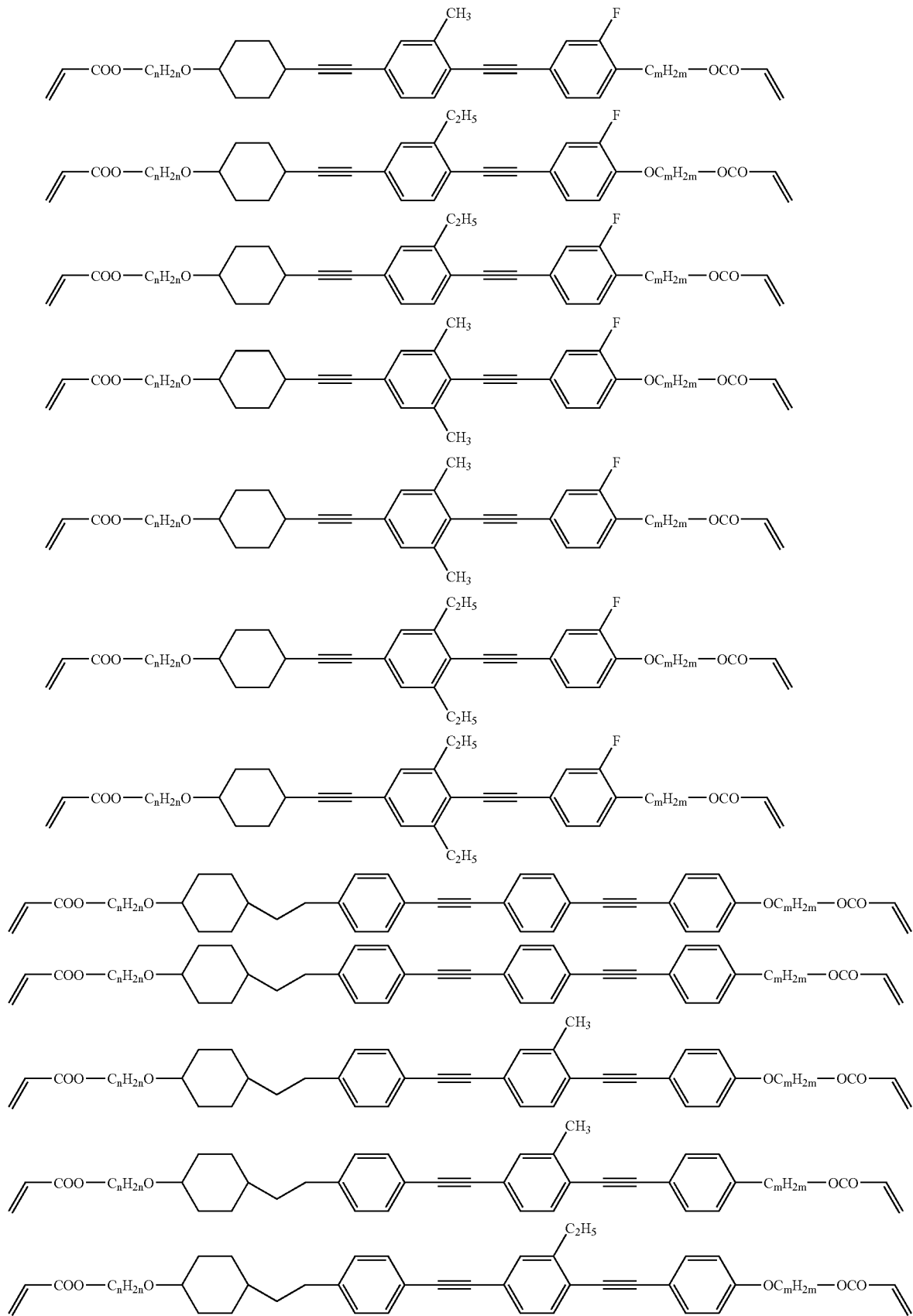

-continued
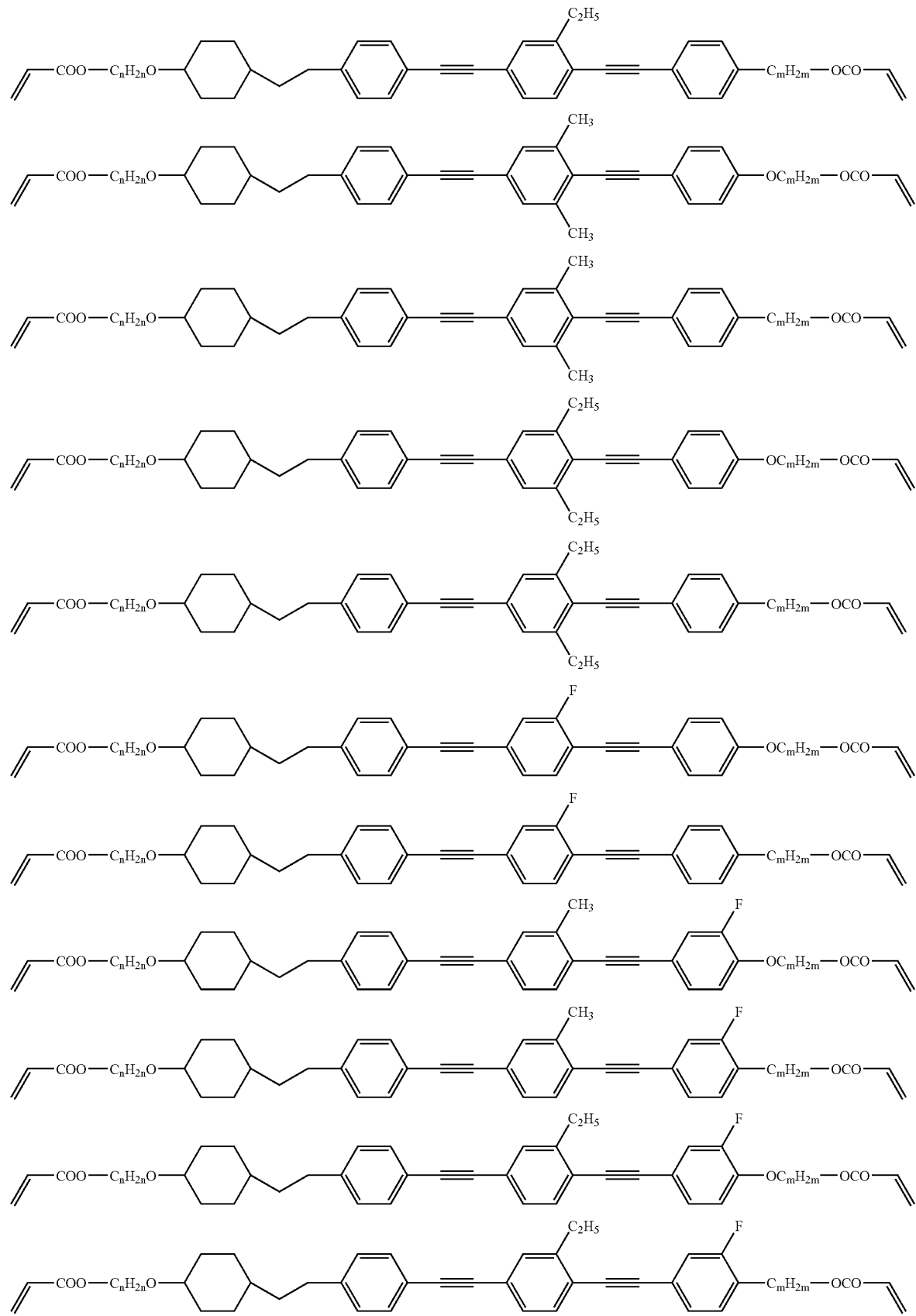

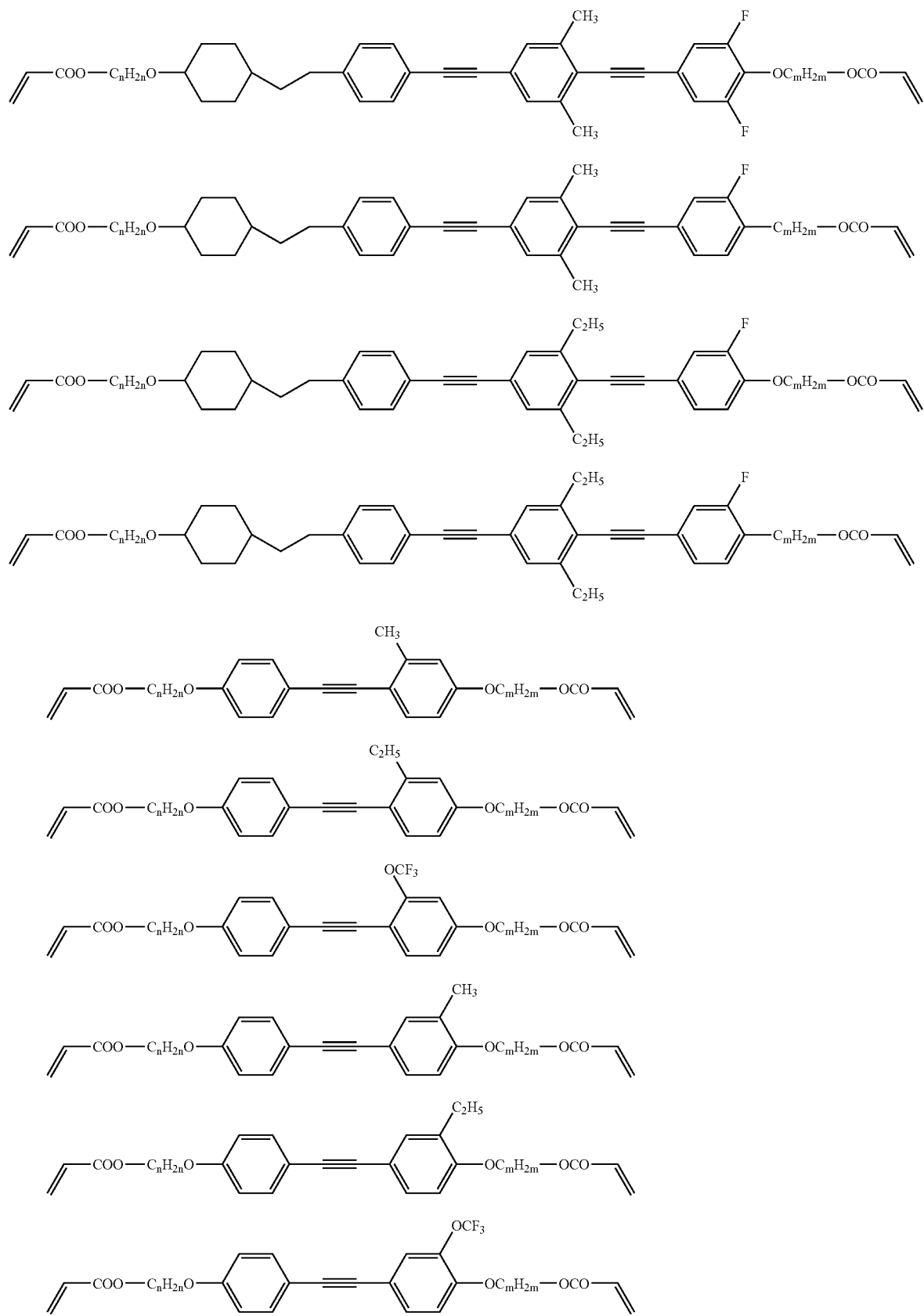

In the formula (5), $A^{13}$ to $A^{24}$ each independently stands for a hydrogen atom, a fluorine atom, an alkyl or alkoxy group having 1 to 10 carbon atoms optionally substituted with at least one fluorine atom, and at least one of $A^{13}$ to $A^{24}$ stands for an alkyl or alkoxy group having 1 to 10 carbon atoms optionally substituted with at least one fluorine atom. $R^{31}$ and $R^{32}$ each independently stands for a hydrogen atom, a fluorine atom, a cyano group, $-SF_5$, $-NCS$, 4-$R^{33}$-(cycloalkyl) group, 4-$R^{33}$-(cycloalkenyl) group, or $R^{34}-(O)_{q^{31}}$ group, wherein $R^{33}$ stands for a hydrogen atom or a straight or branched alkyl group having 1 to 12 carbon atoms optionally substituted with at least one fluorine atom, $R^{34}$ stands for a straight or branched alkyl group having 1 to 12 carbon atoms optionally substituted with at least one fluorine atom, and $q^{31}$ denotes 0 or 1.

Examples of the compound represented by the formula (5) may include the compounds represented by the following formulae:

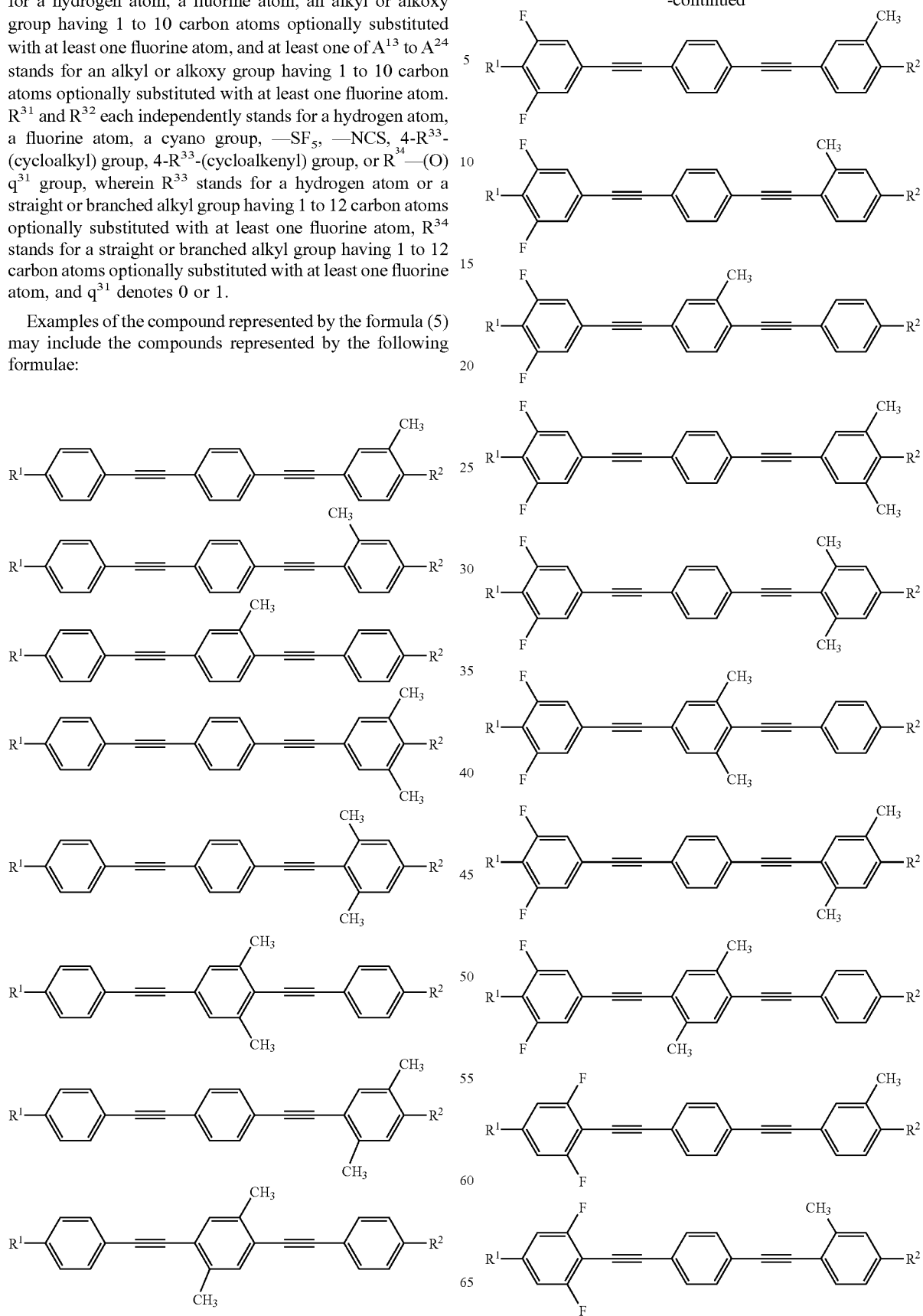

-continued
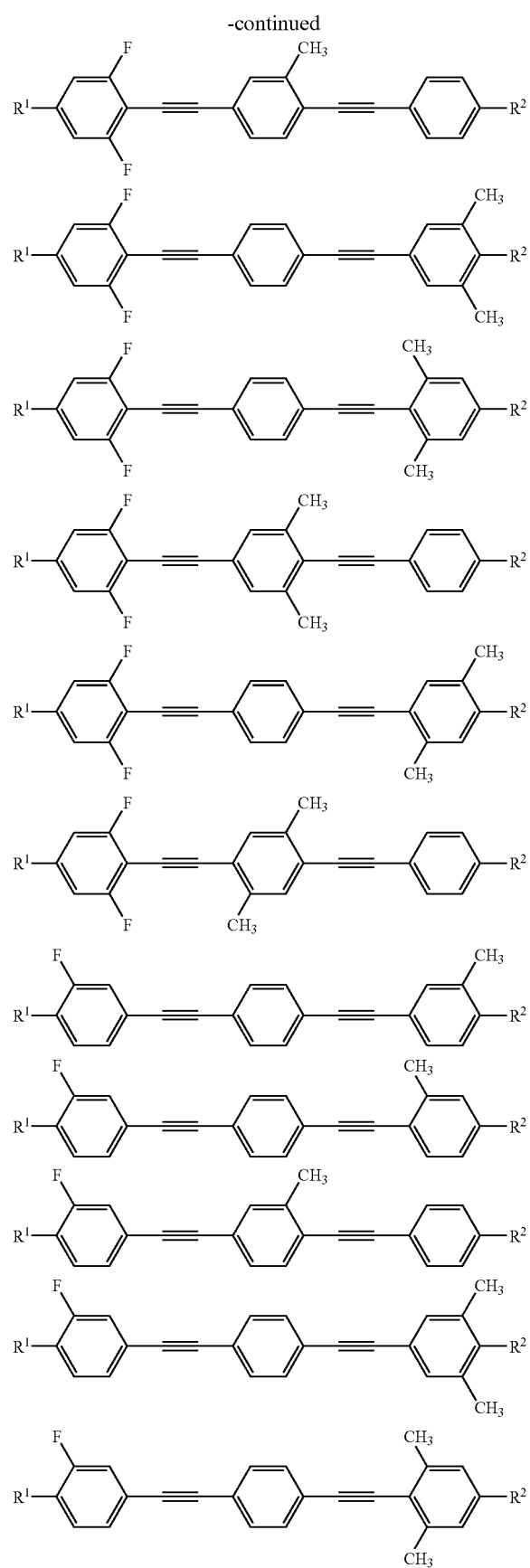
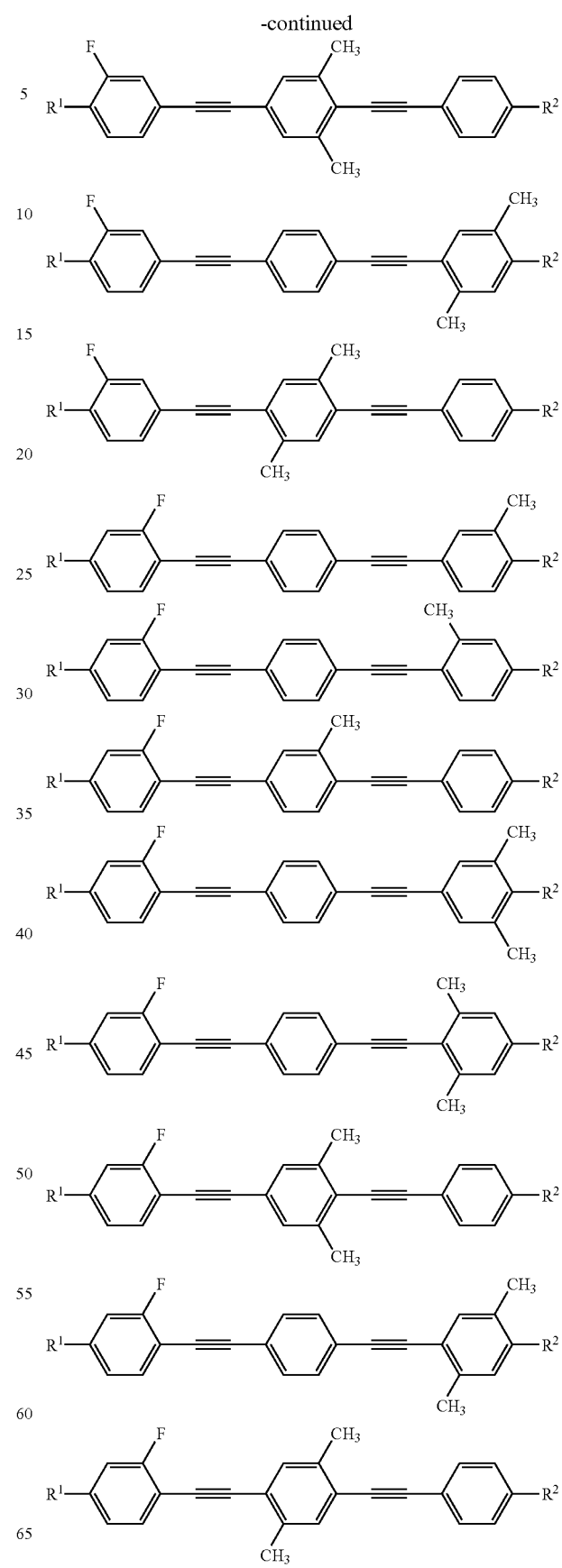

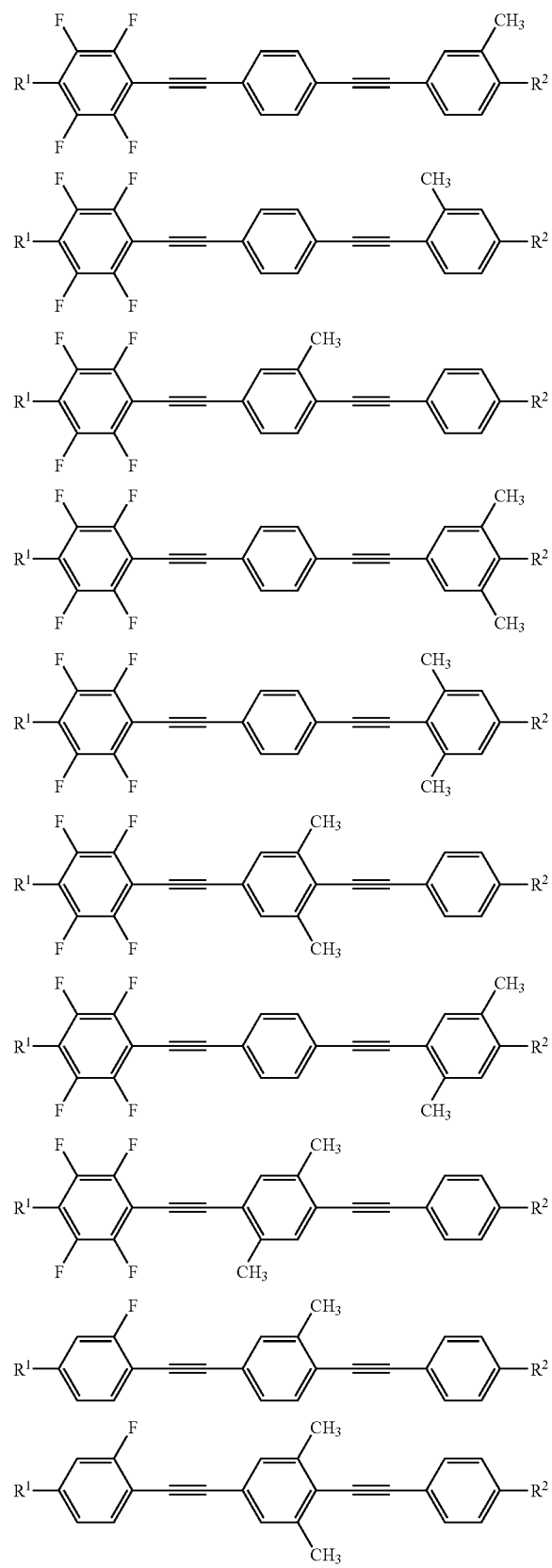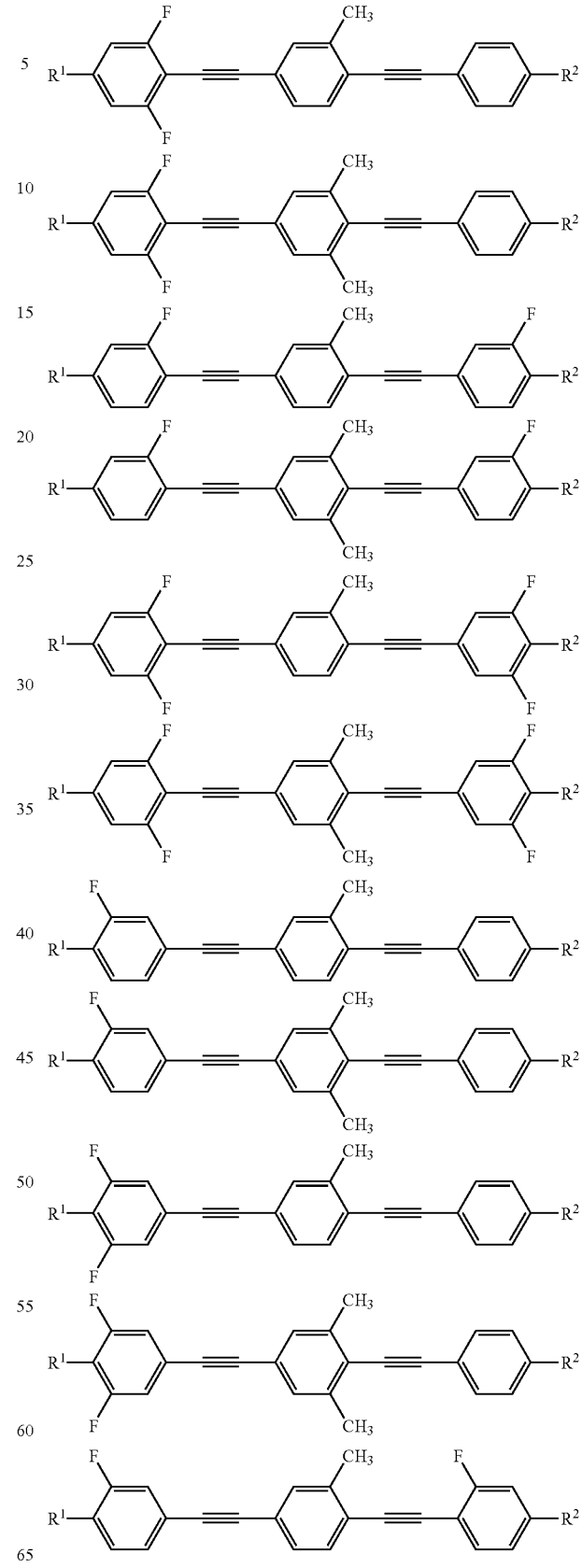

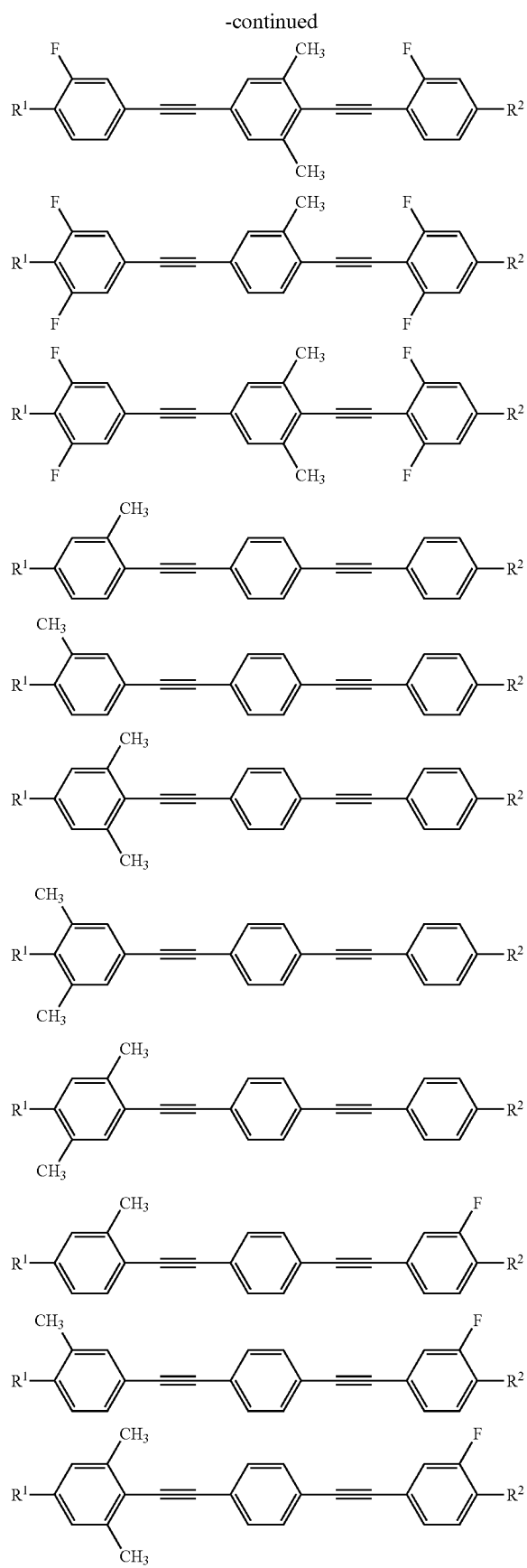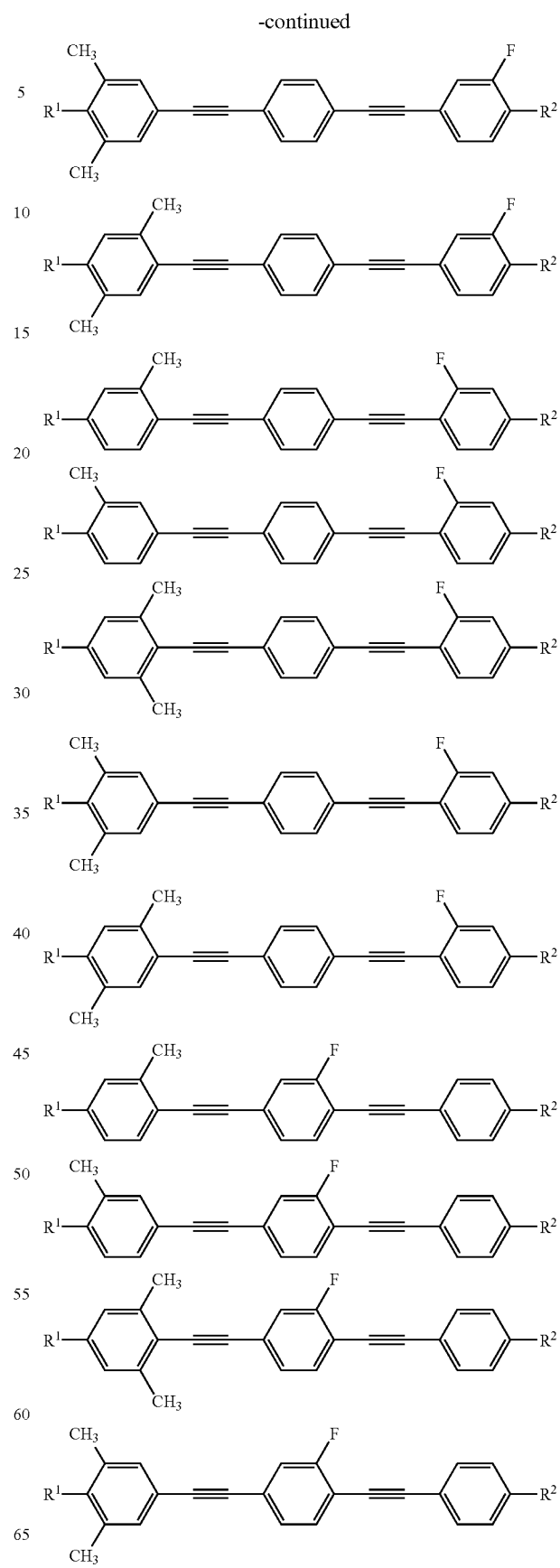

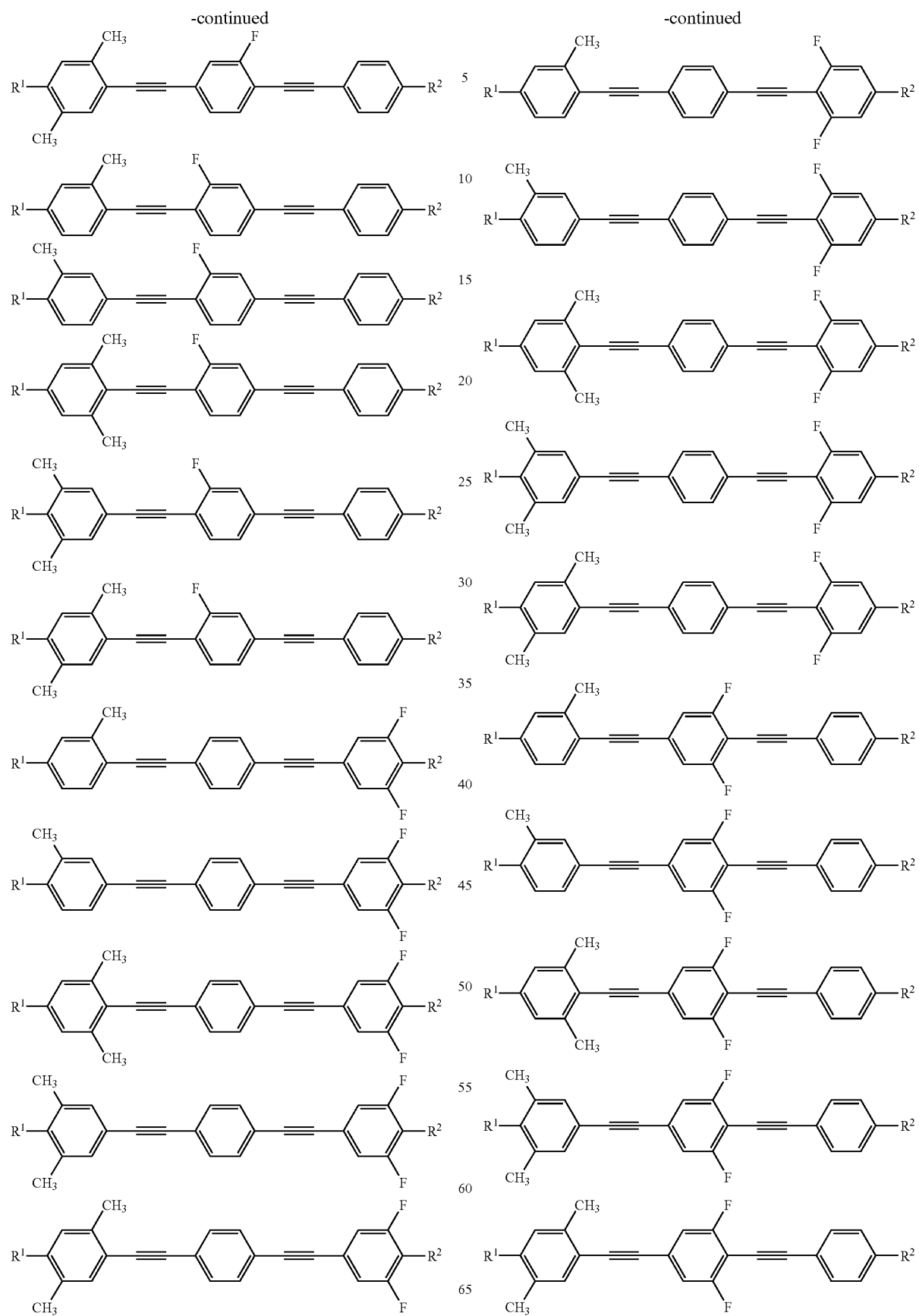

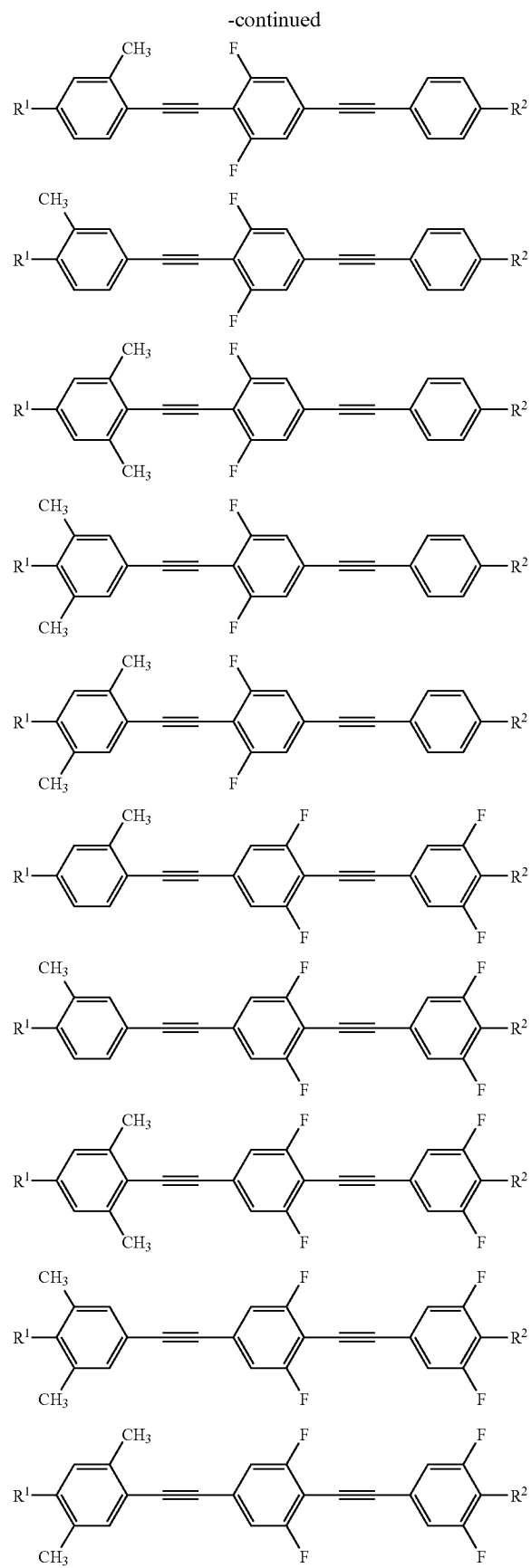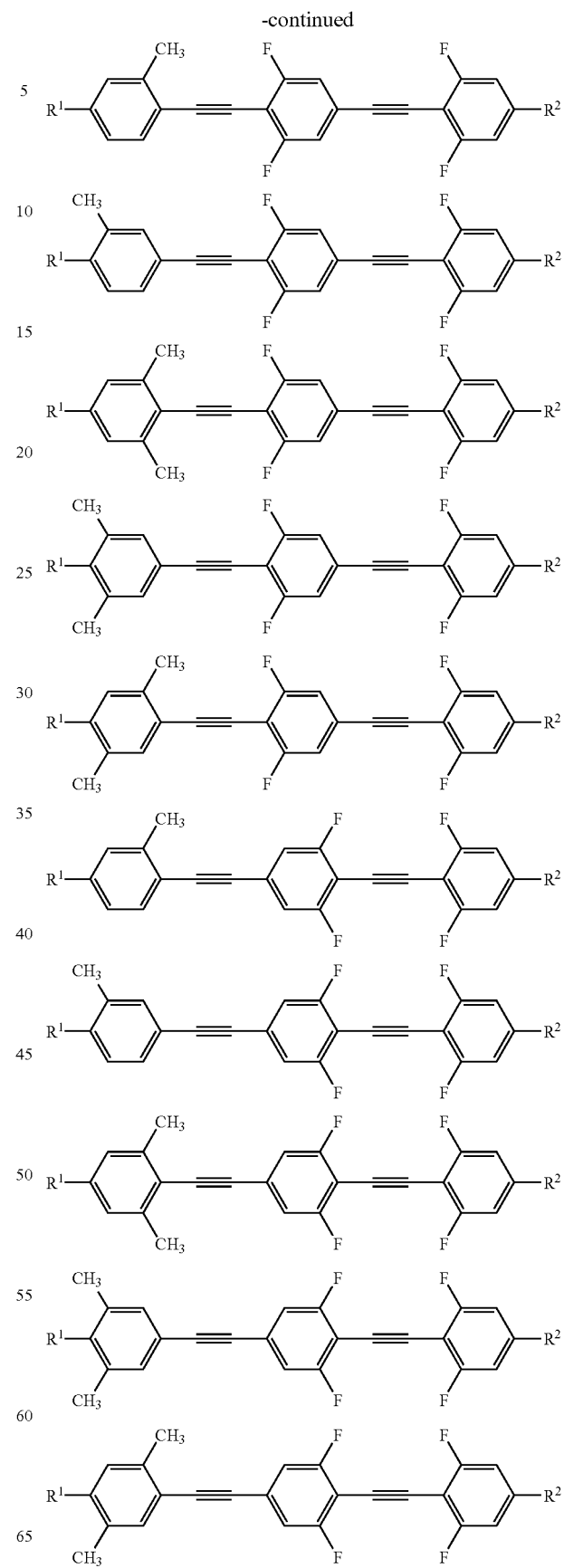

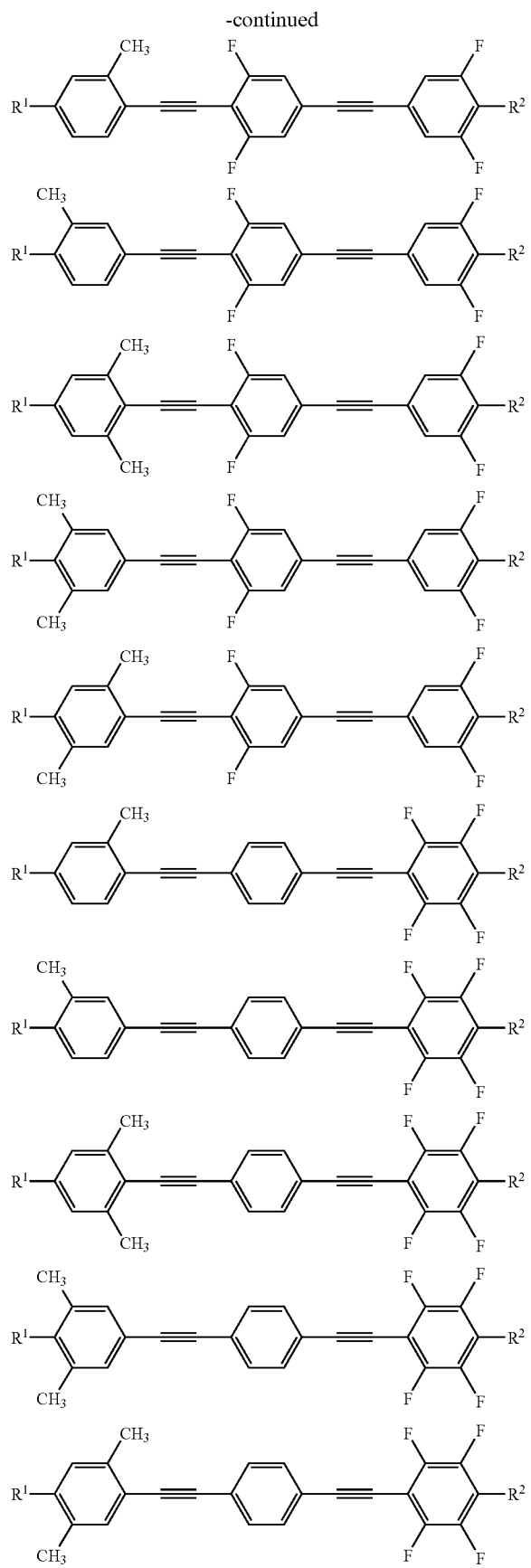

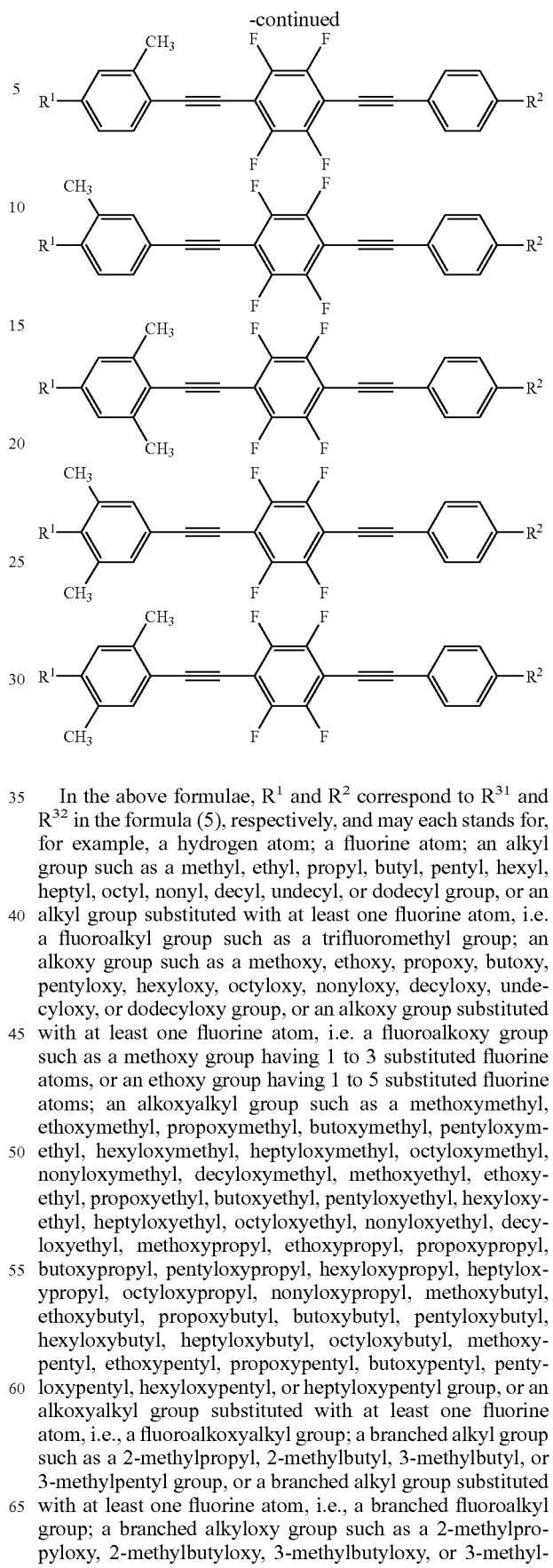

In the above formulae, $R^1$ and $R^2$ correspond to $R^{31}$ and $R^{32}$ in the formula (5), respectively, and may each stands for, for example, a hydrogen atom; a fluorine atom; an alkyl group such as a methyl, ethyl, propyl, butyl, pentyl, hexyl, heptyl, octyl, nonyl, decyl, undecyl, or dodecyl group, or an alkyl group substituted with at least one fluorine atom, i.e. a fluoroalkyl group such as a trifluoromethyl group; an alkoxy group such as a methoxy, ethoxy, propoxy, butoxy, pentyloxy, hexyloxy, octyloxy, nonyloxy, decyloxy, undecyloxy, or dodecyloxy group, or an alkoxy group substituted with at least one fluorine atom, i.e. a fluoroalkoxy group such as a methoxy group having 1 to 3 substituted fluorine atoms, or an ethoxy group having 1 to 5 substituted fluorine atoms; an alkoxyalkyl group such as a methoxymethyl, ethoxymethyl, propoxymethyl, butoxymethyl, pentyloxymethyl, hexyloxymethyl, heptyloxymethyl, octyloxymethyl, nonyloxymethyl, decyloxymethyl, methoxyethyl, ethoxyethyl, propoxyethyl, butoxyethyl, pentyloxyethyl, hexyloxyethyl, heptyloxyethyl, octyloxyethyl, nonyloxyethyl, decyloxyethyl, methoxypropyl, ethoxypropyl, propoxypropyl, butoxypropyl, pentyloxypropyl, hexyloxypropyl, heptyloxypropyl, octyloxypropyl, nonyloxypropyl, methoxybutyl, ethoxybutyl, propoxybutyl, butoxybutyl, pentyloxybutyl, hexyloxybutyl, heptyloxybutyl, octyloxybutyl, methoxypentyl, ethoxypentyl, propoxypentyl, butoxypentyl, pentyloxypentyl, hexyloxypentyl, or heptyloxypentyl group, or an alkoxyalkyl group substituted with at least one fluorine atom, i.e., a fluoroalkoxyalkyl group; a branched alkyl group such as a 2-methylpropyl, 2-methylbutyl, 3-methylbutyl, or 3-methylpentyl group, or a branched alkyl group substituted with at least one fluorine atom, i.e., a branched fluoroalkyl group; a branched alkyloxy group such as a 2-methylpropyloxy, 2-methylbutyloxy, 3-methylbutyloxy, or 3-methylpentyloxy group, or a branched alkyloxy group substituted with at least one fluorine atom, i.e., a branched fluoroalkyloxy group; a 4-alkylcycloalkyl group such as a 4-methylcyclohexyl, 4-ethylcyclohexyl, 4-propylcyclohexyl, 4-butylcyclohexyl, 4-pentylcyclohexyl, 4-hexylcyclohexyl, 4-heptylcyclohexyl, 4-octylcyclohexyl, 4-nonylcyclohexyl, or 4-decylcyclohexyl group, or a 4-alkylcycloalkyl group substituted with at least one fluorine atom, i.e., a 4-fluoroalkylcycloalkyl group; a 4-alkylcycloalkenyl group such as a 4-propylcyclohexenyl or 4-pentylcyclohexenyl group, or a 4-alkylcycloalkenyl group substituted with at least one fluorine atom, i.e., a 4-fluoroalkylcycloalkenyl group; a cyano group; —$SF_5$; or —NCS.

In the formula (6), $A^{25}$ to $A^{36}$ each independently stands for a hydrogen atom, a fluorine atom, or an alkyl group having 1 to 10 carbon atoms. m denotes 0 or 1. $R^{41}$ stands for a hydrogen atom or a straight or branched alkyl group having 1 to 12 carbon atoms optionally substituted with at least one fluorine atom. $R^{42}$ stands for $R^{41}$, a fluorine atom, a cyano group, 4-$R^{43}$-(cycloalkyl) group, 4-$R^{43}$-(cycloalkenyl) group, or $R^{44}$—(O)$q^{41}$ group, wherein $R^{43}$ stands for a hydrogen atom or a straight or branched alkyl group having 1 to 12 carbon atoms optionally substituted with at least one fluorine atom, $R^{44}$ stands for a straight or branched alkyl group having 1 to 12 carbon atoms optionally substituted with at least one fluorine atom, and $q^{41}$ denotes 0 or 1.

Examples of the compound represented by the formula (6) may include the compounds represented by the following formulae:

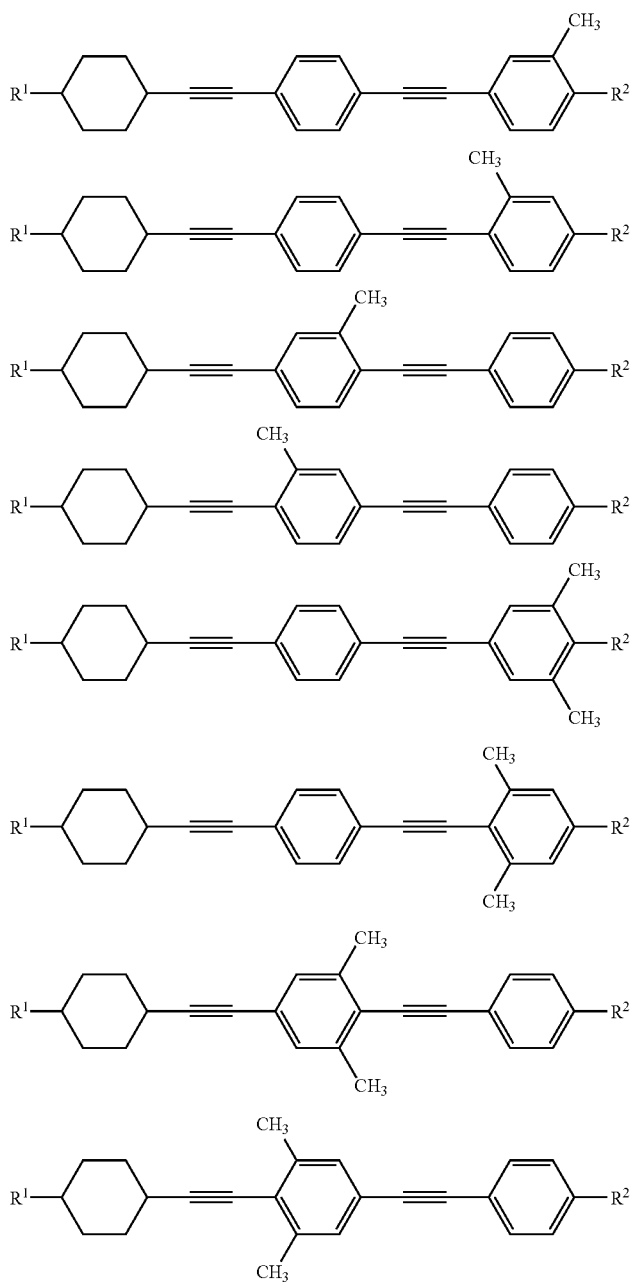

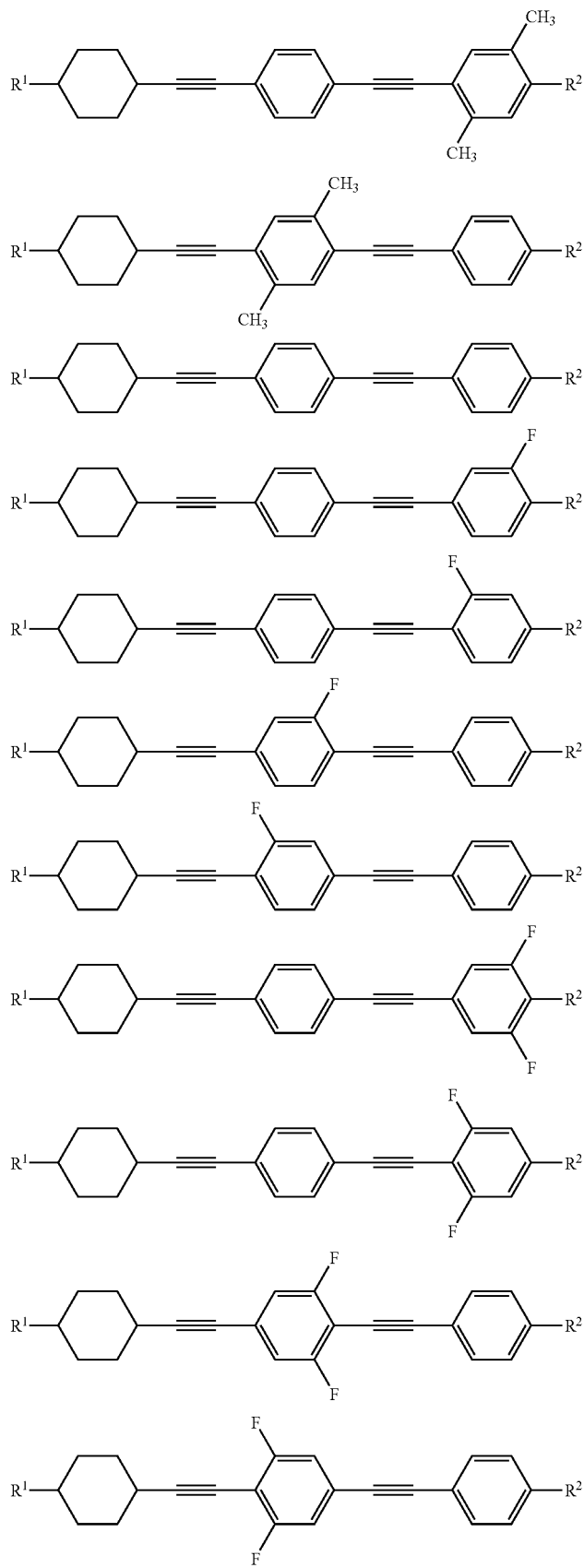

-continued
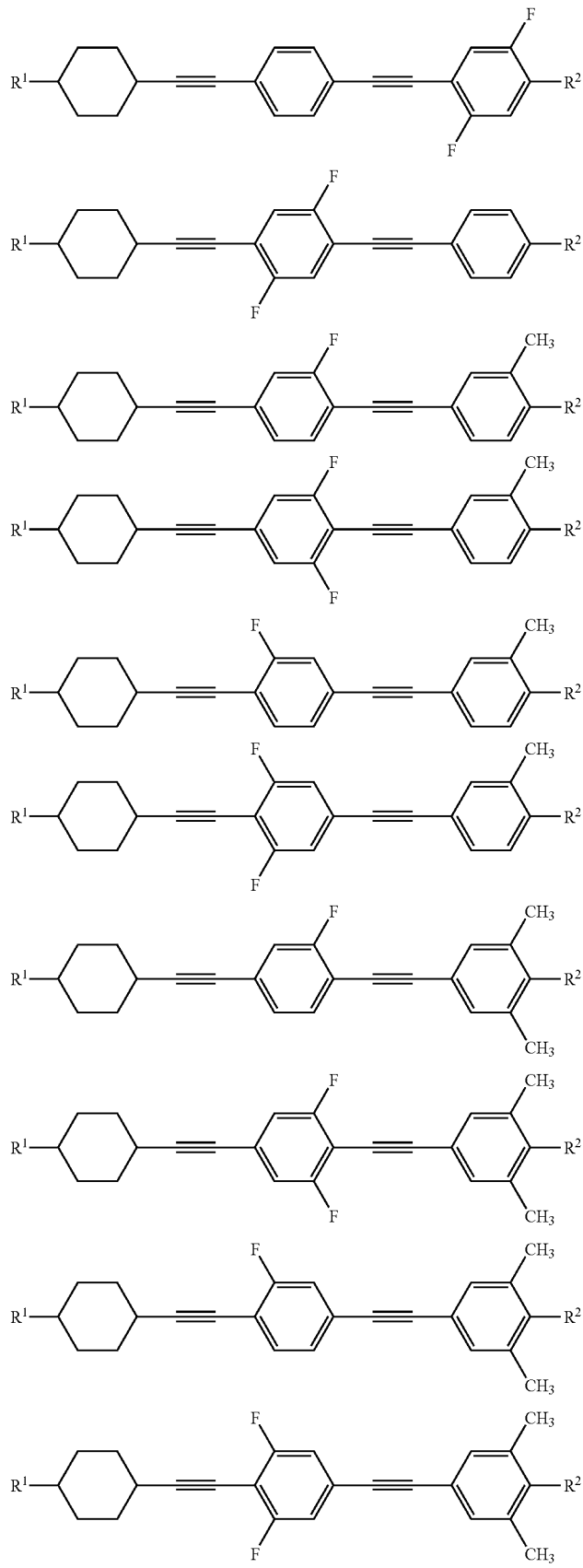

-continued
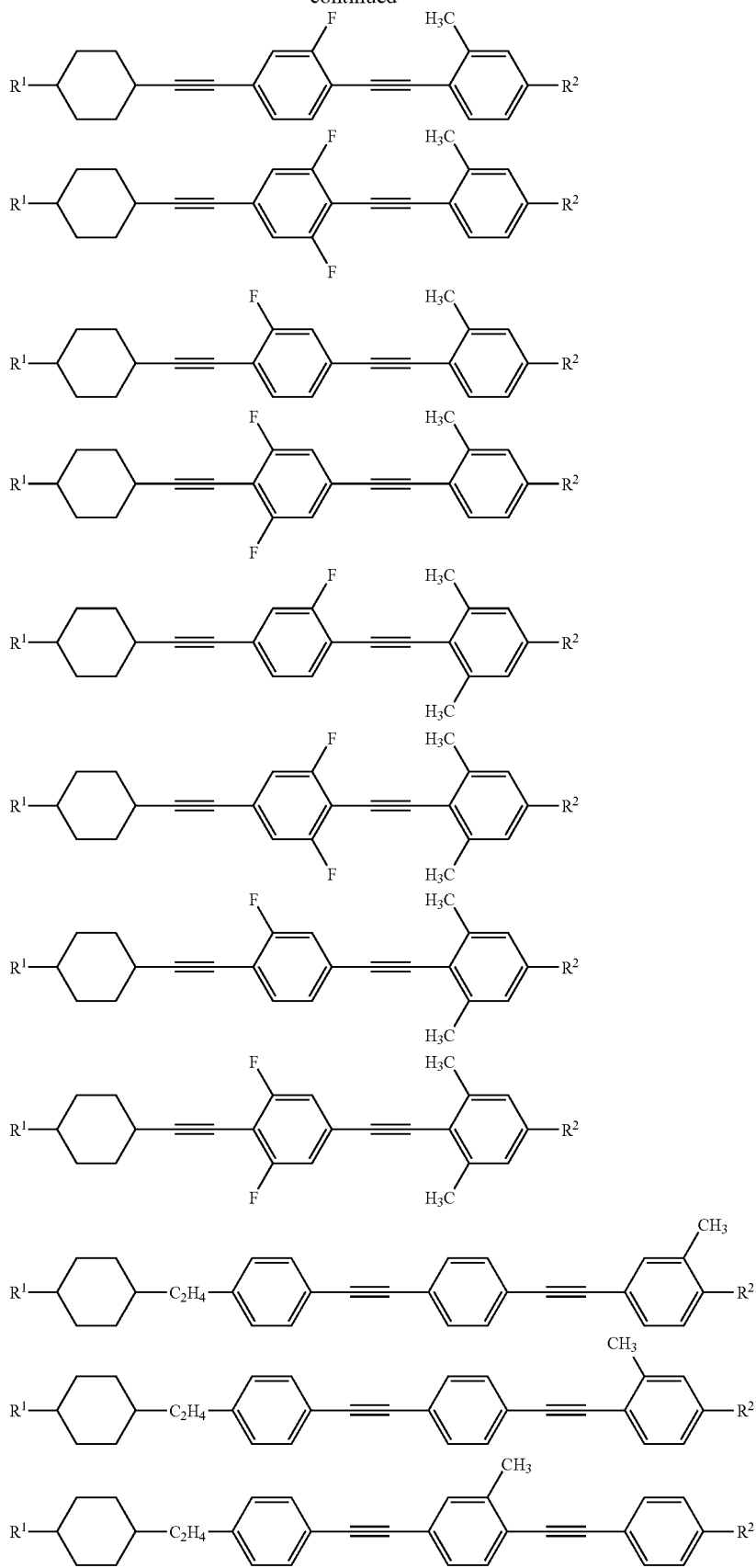

-continued
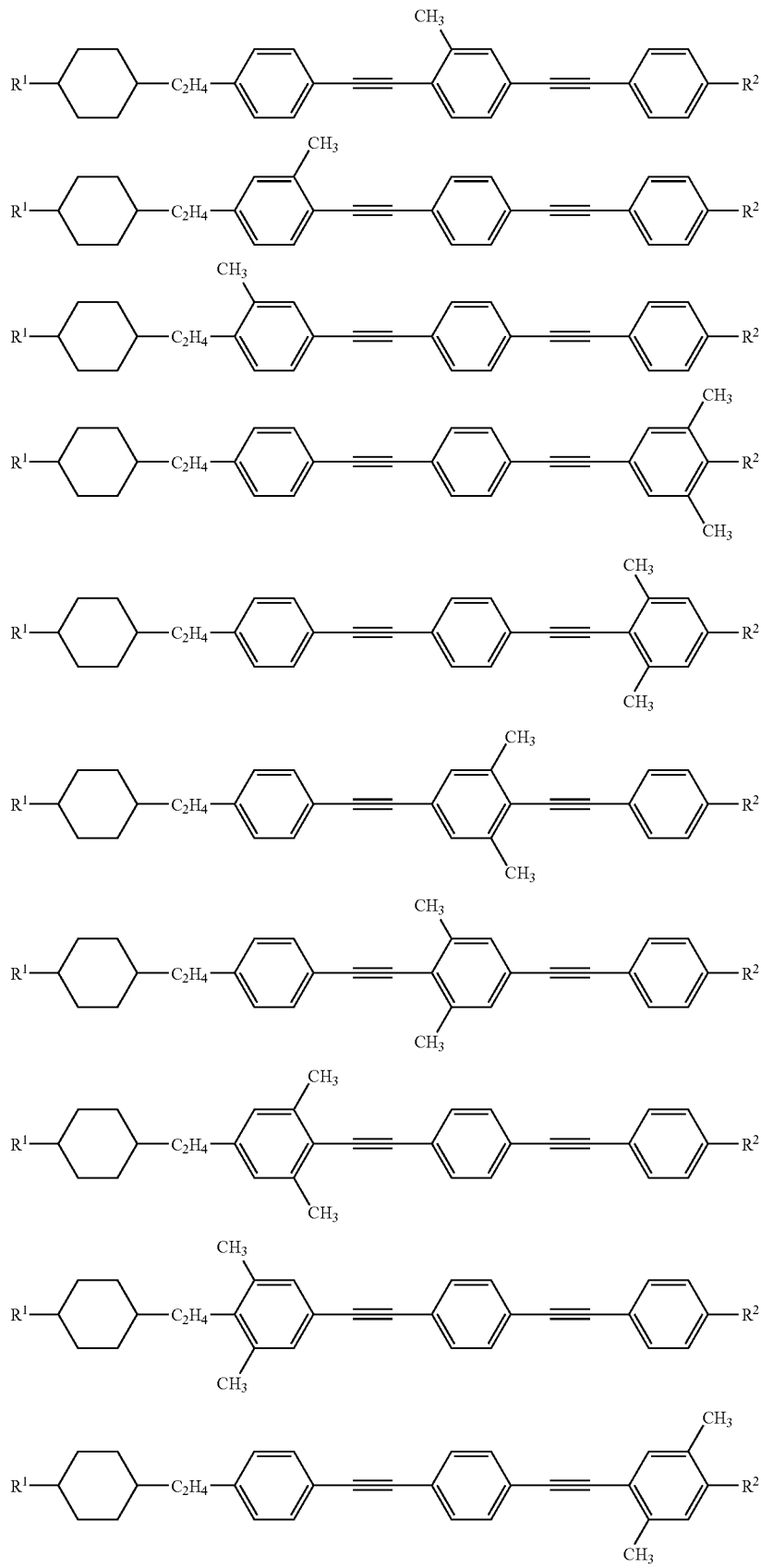

-continued
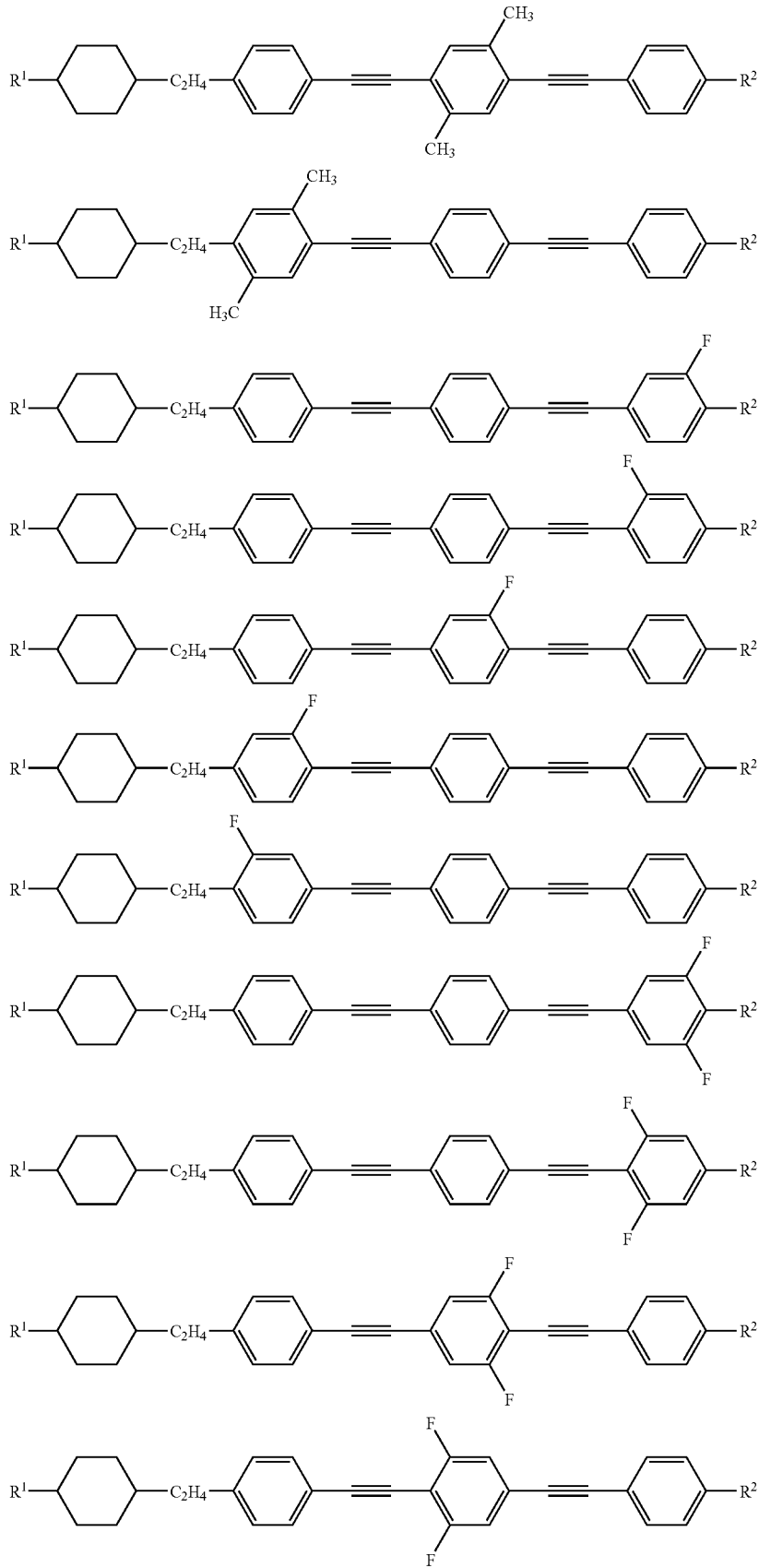

-continued
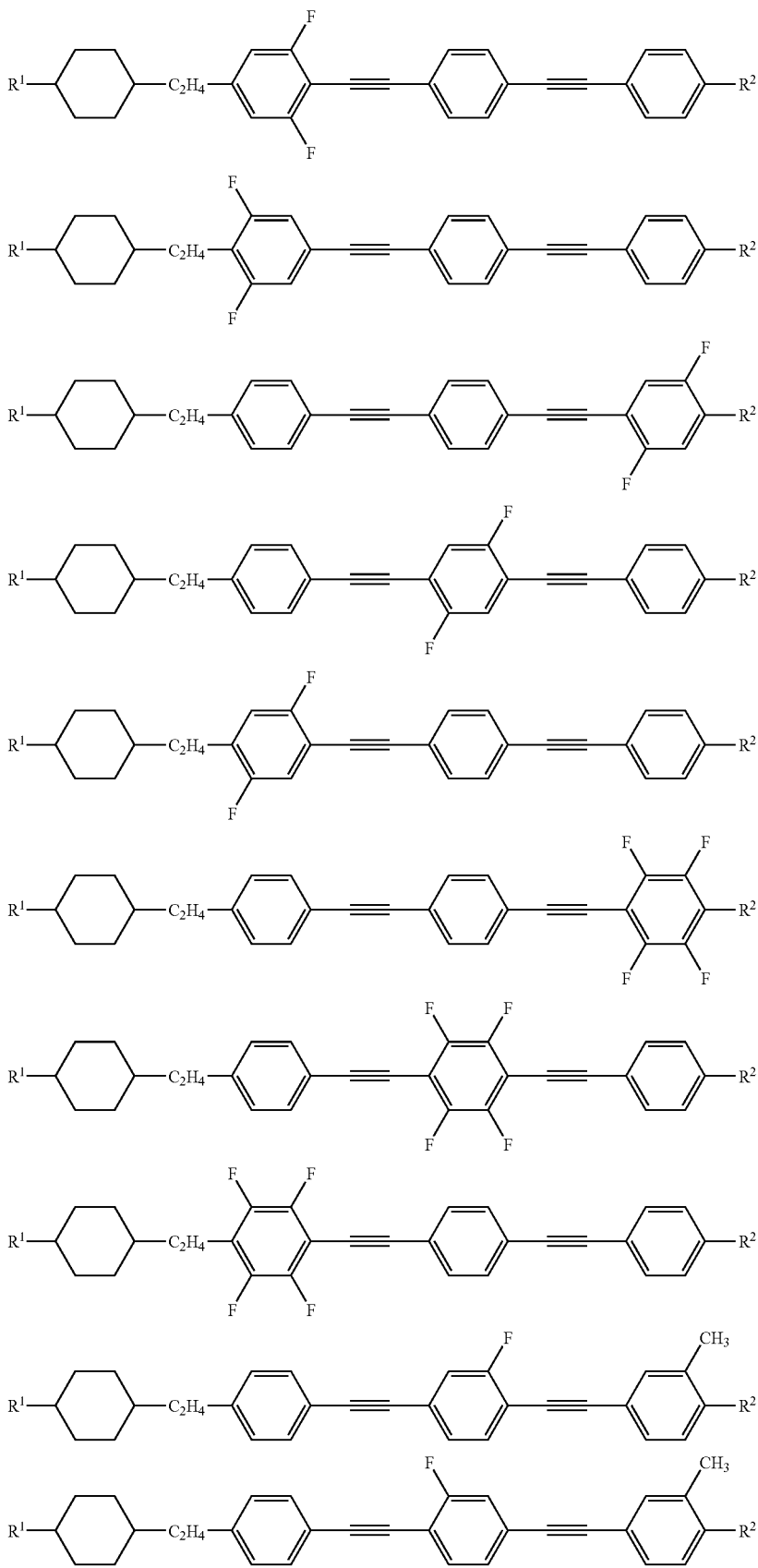

-continued
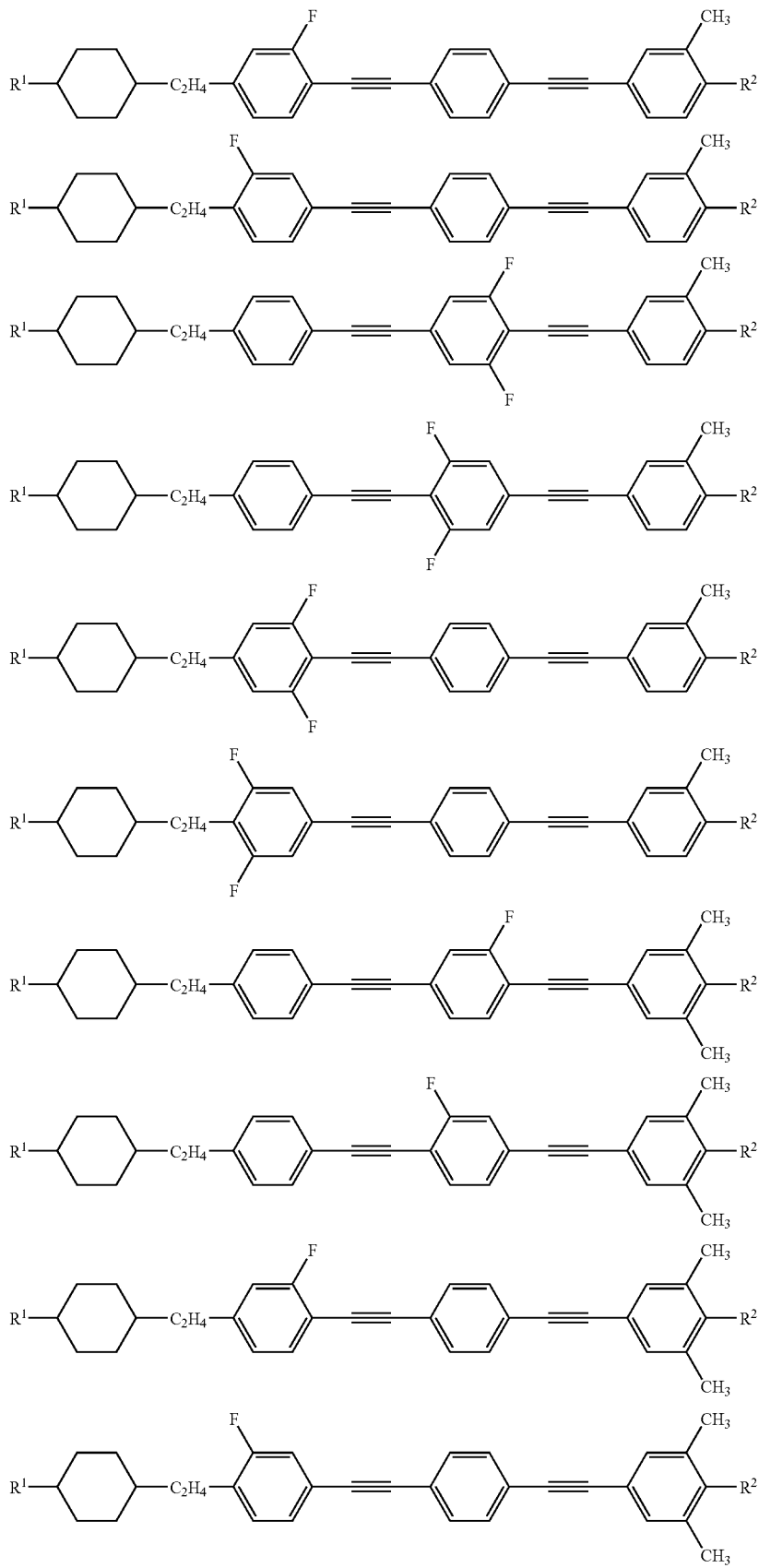

-continued
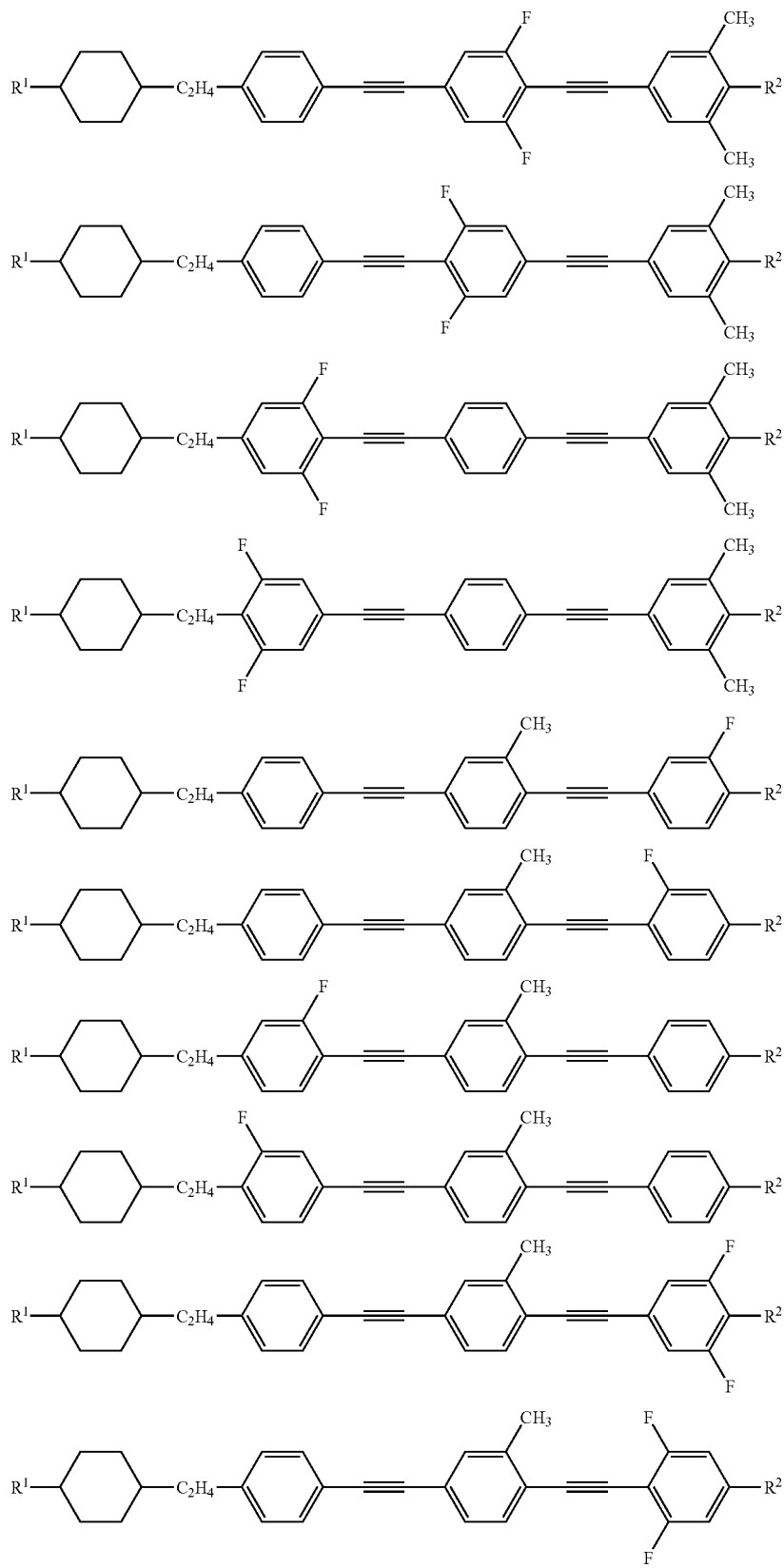

-continued
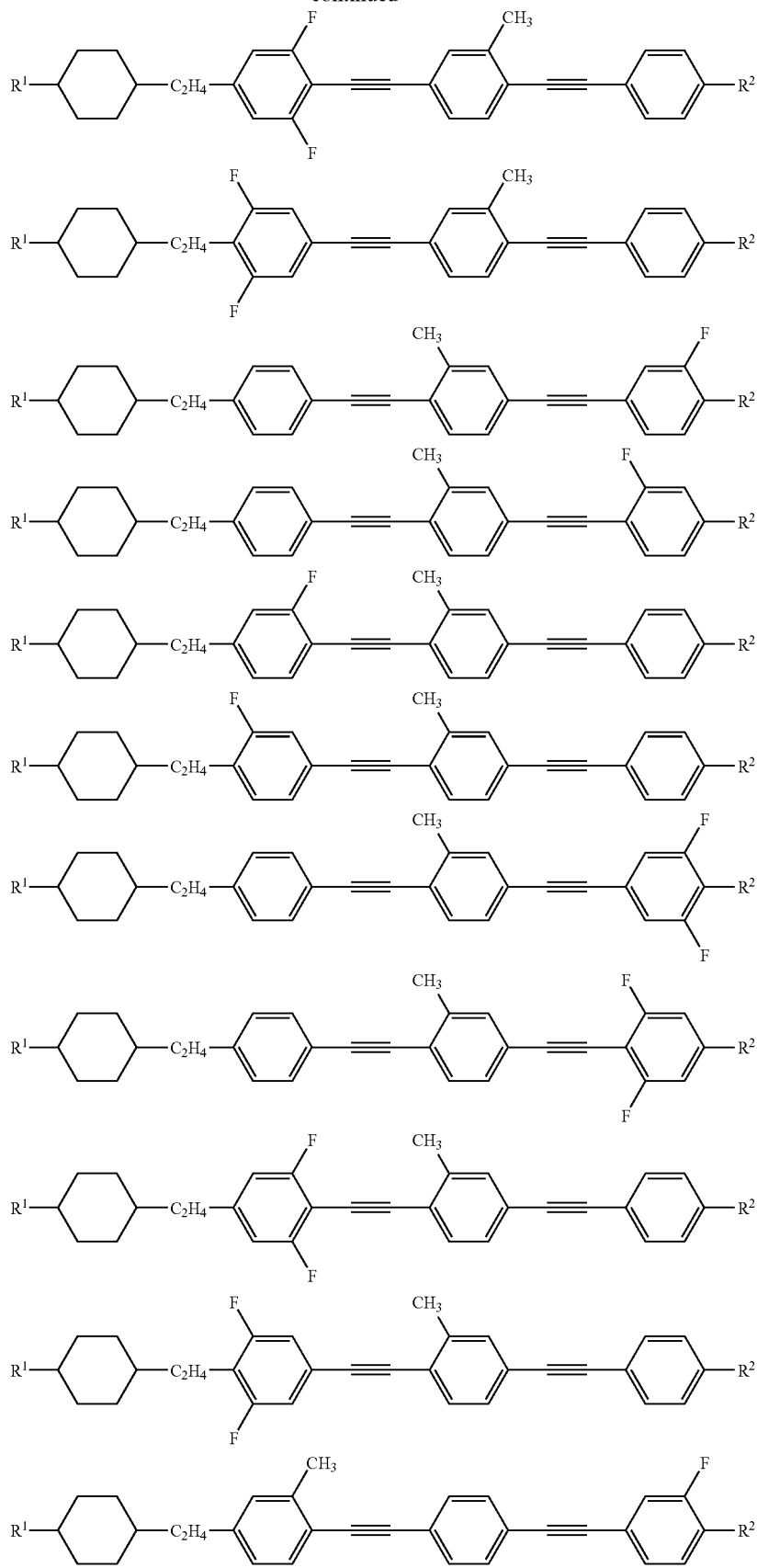

-continued
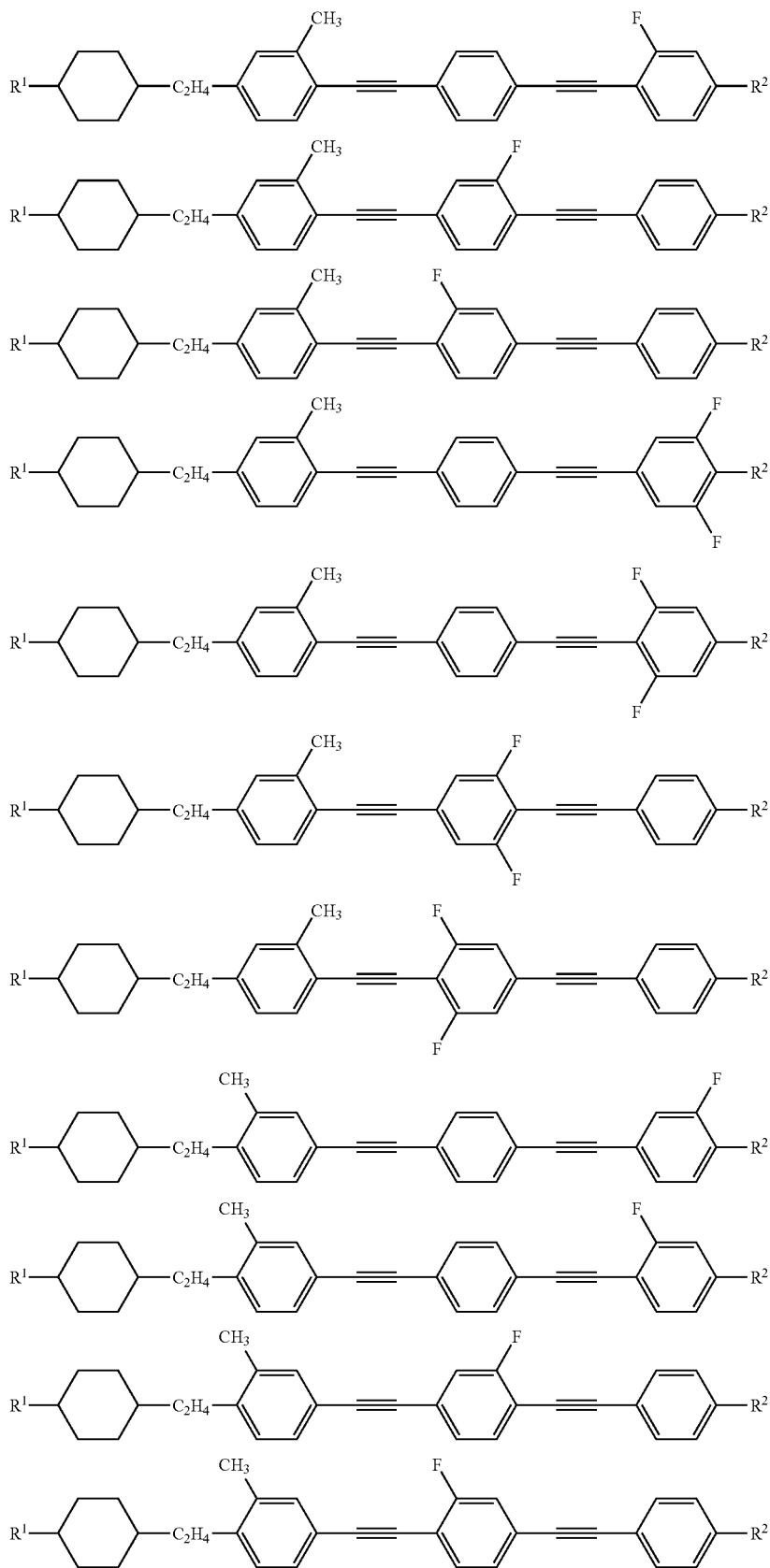

-continued
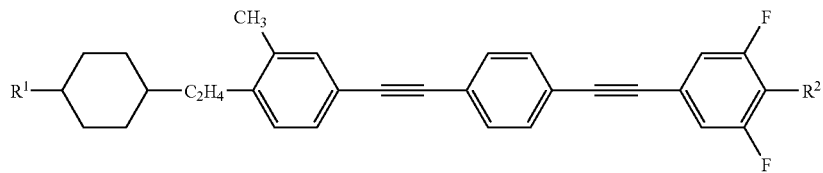
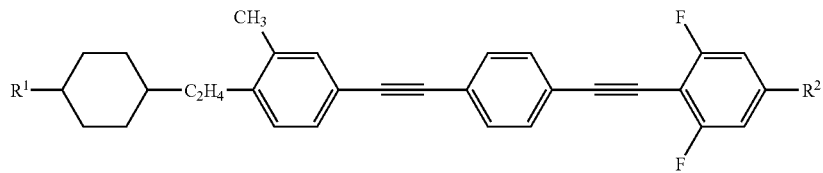
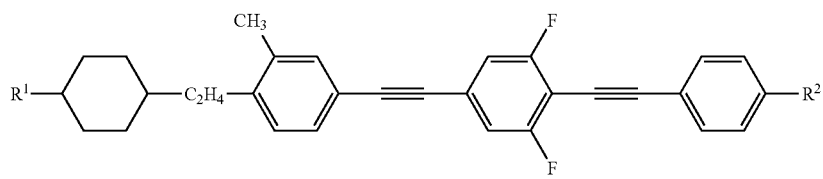
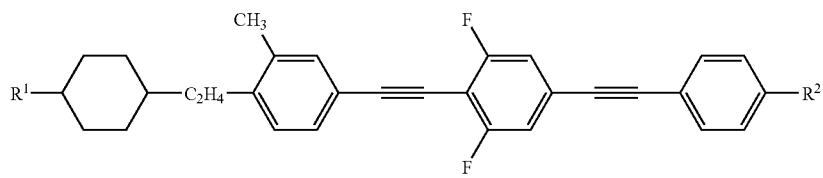
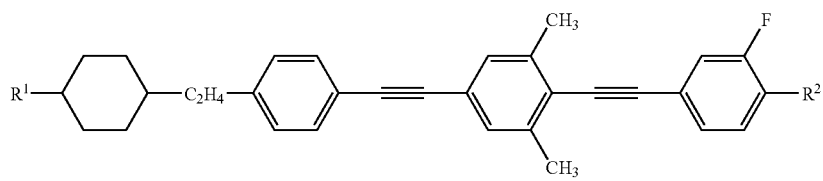
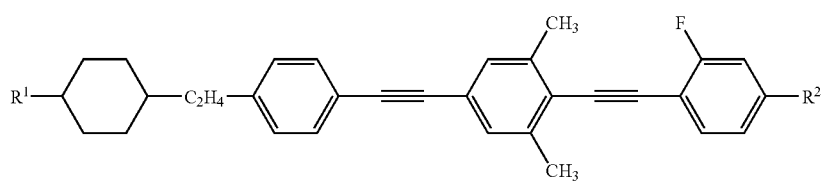
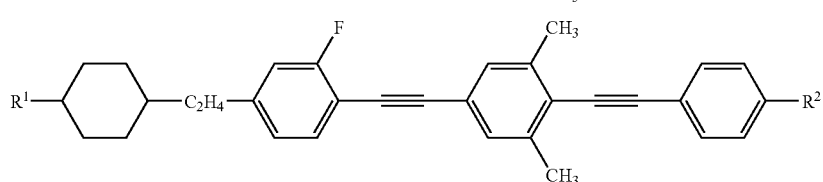
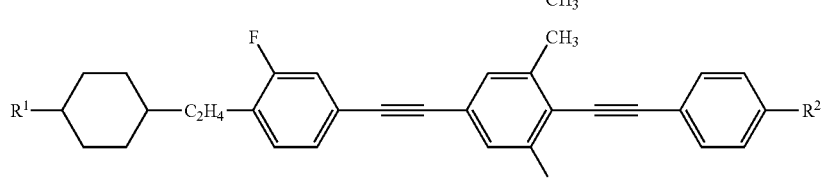
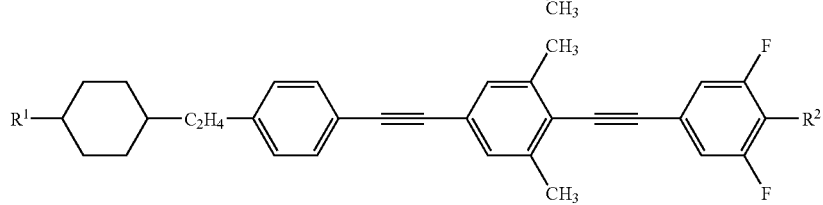

-continued
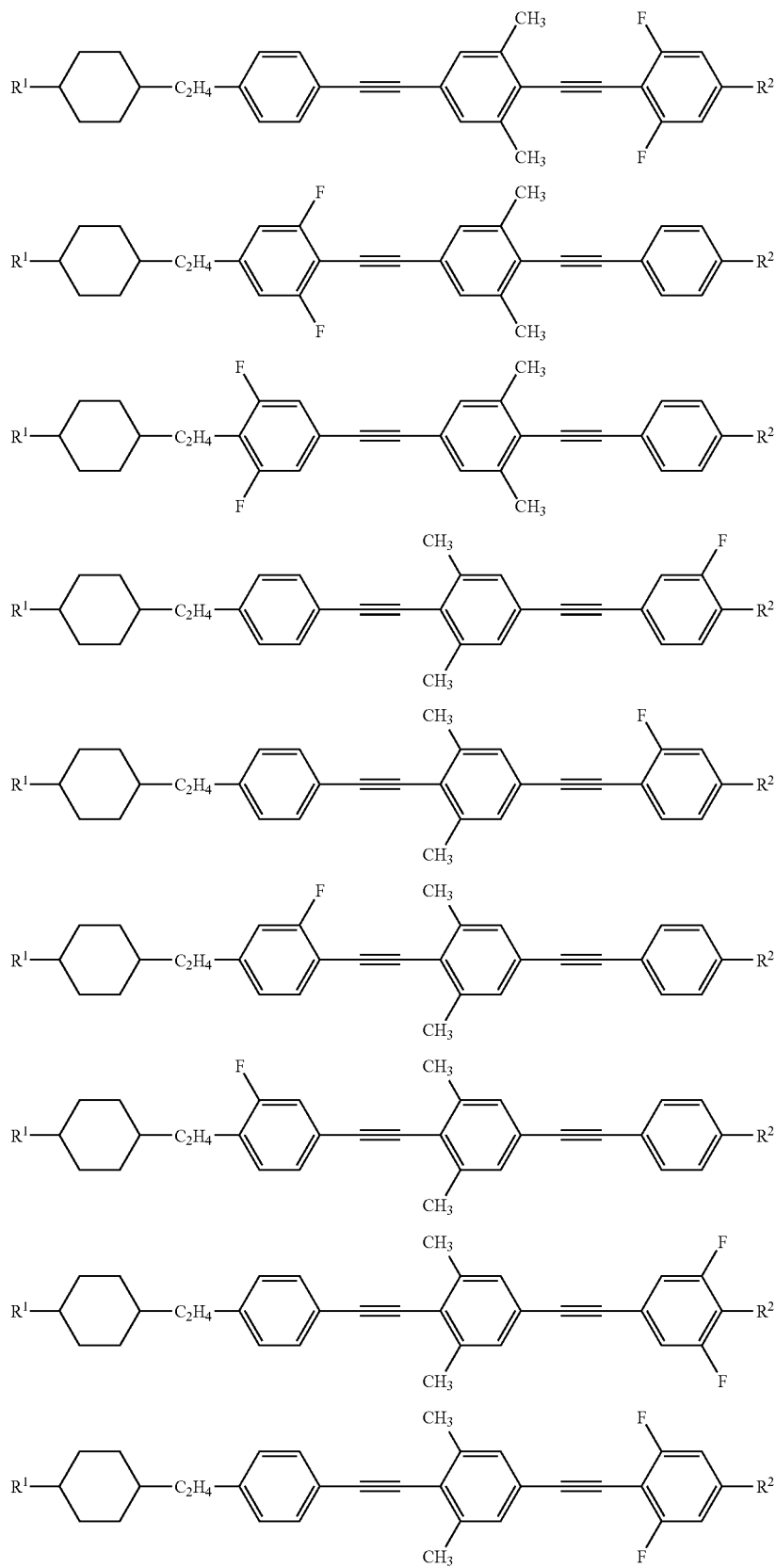

-continued
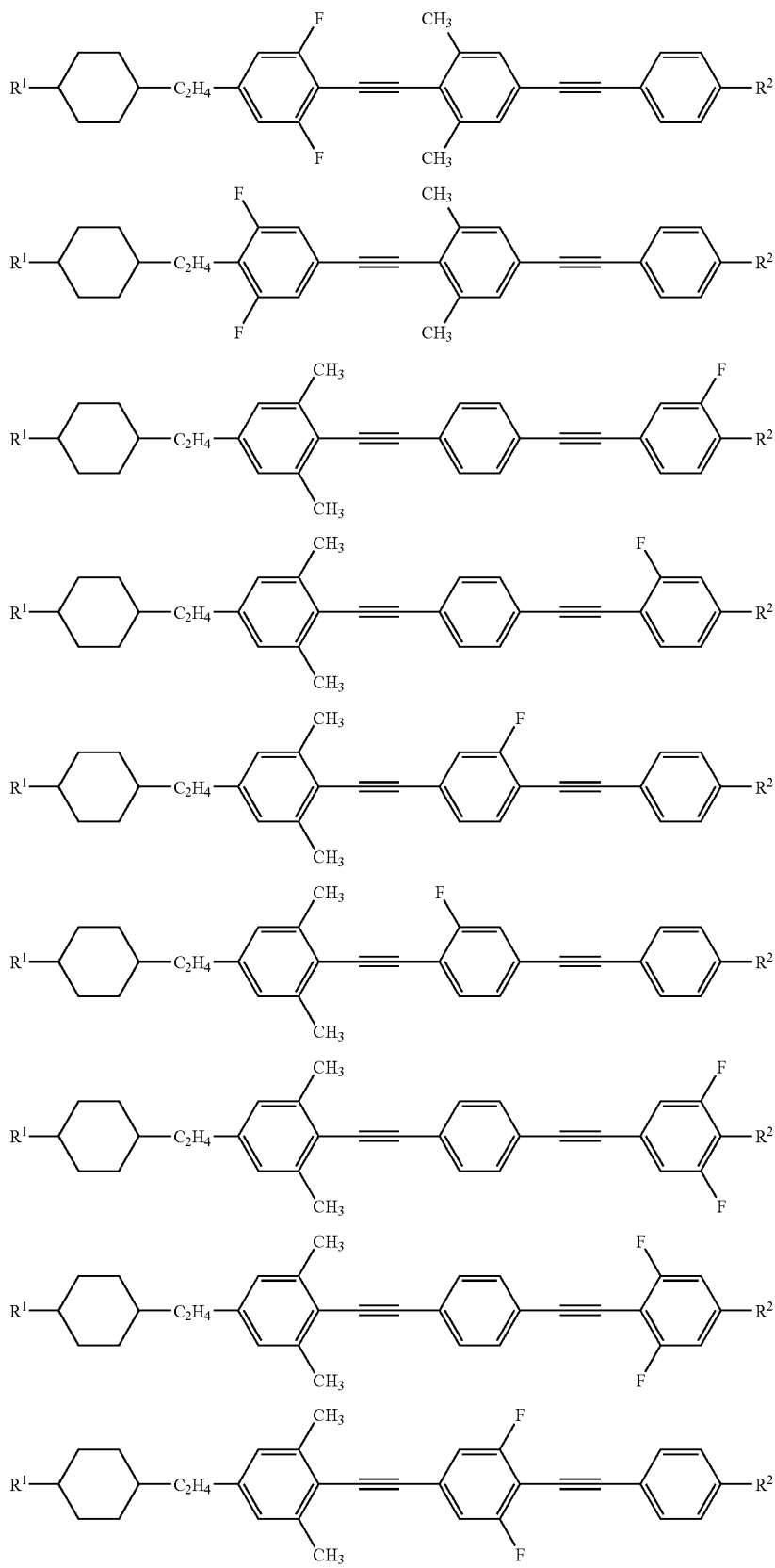

-continued
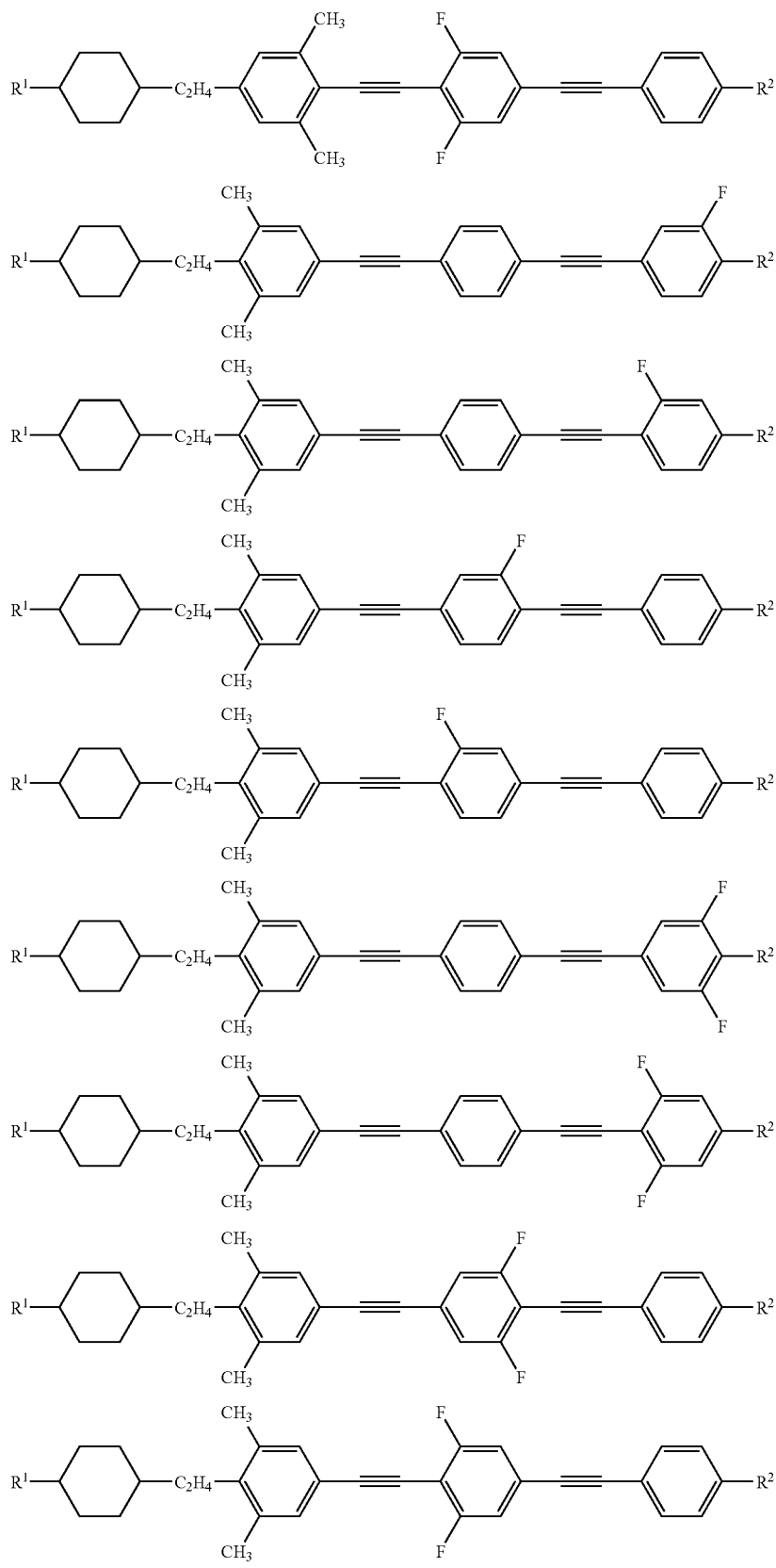

In the above formulae, $R^1$ and $R^2$ correspond to $R^{41}$ and $R^{42}$ in the formula (6), respectively, and may be the same as those listed as examples of $R^1$ and $R^2$ corresponding to $R^{31}$ and $R^{32}$ in the formula (5), except for —SF$_5$ and —NCS, but are not limited to these.

In the formula (7), Rings A, B, C, and D each independently stands for 1,4-phenylene, 1,4-cyclohexylene, 1,4-cyclohexenylene, 4,1-cyclohexenylene, 2,5-cyclohexenylene, 5,2-cyclohexenylene, 3,6-cyclohexenylene, 6,3-cyclohexenylene, 2,5-pyrimidinediyl, 5,2-pyrimidinediyl, 2,5-pyridinediyl, 5,2-pyridinediyl, 2,5-dioxanediyl, or 5,2-dioxanediyl, with at least one of the hydrogen atoms on Rings A, B, C, and D being optionally substituted with a fluorine atom. $R^{51}$ and $R^{52}$ each independently stands for a hydrogen atom, a fluorine atom, a fluoromethyl group, a difluoromethyl group, a trifluoromethyl group, a fluoromethoxy group, a difluoromethoxy group, a trifluoromethoxy group, a cyano group, an alkyl group having 1 to 12 carbon atoms, an alkenyl group having 3 to 12 carbon atoms, an alkynyl group having 3 to 12 carbon atoms, an alkoxy group having 1 to 12 carbon atoms, an alkenyloxy group having 3 to 12 carbon atoms, an alkynyloxy group having 3 to 12 carbon atoms, an alkoxyalkyl group having 2 to 16 carbon atoms, an alkoxyalkenyl group having 3 to 16 carbon atoms, or a group represented by the formula (7-1), (7-2), or (7-3). In the formulae (7-1) to (7-3), $m^7$ denotes an integer of 1 to 12, and $n^7$ denotes 0 or 1. These alkyl, alkenyl, and alkynyl groups may optionally have at least one methylene group substituted with an oxygen, sulfur, or silicon atom, and may either be straight or branched. $Z^1$, $Z^2$, and $Z^3$ each independently stands for —COO—, —OCO—, —OCH$_2$—, —CH$_2$O—, an alkylene group having 1 to 5 carbon atoms, an alkenylene group having 2 to 5 carbon atoms, an alkynylene group having 2 to 5 carbon atoms, or a single bond. b, c, and d each independently denotes 0 or 1, with b+c+d≧1.

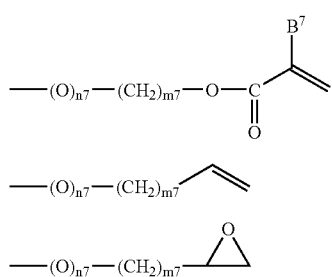

(7-1)

(7-2)

(7-3)

Examples of the compound represented by the formula (7) may include the compounds represented by the following formulae:

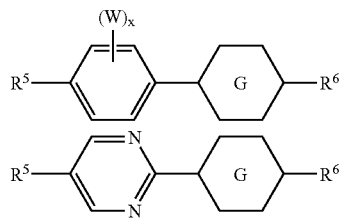

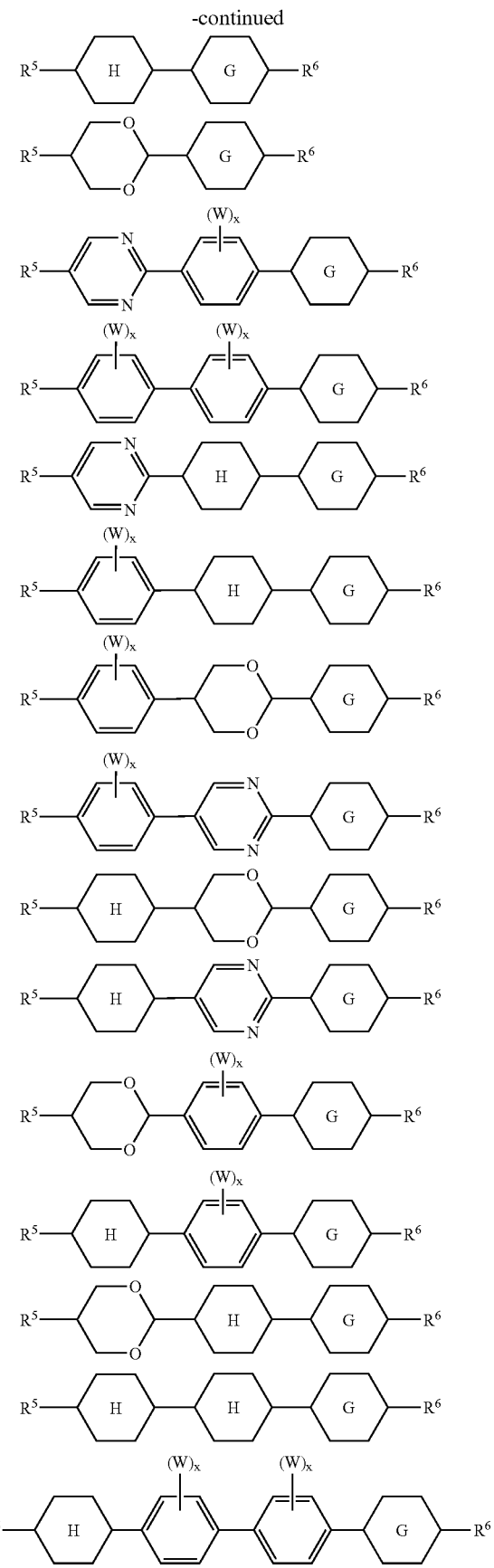

-continued
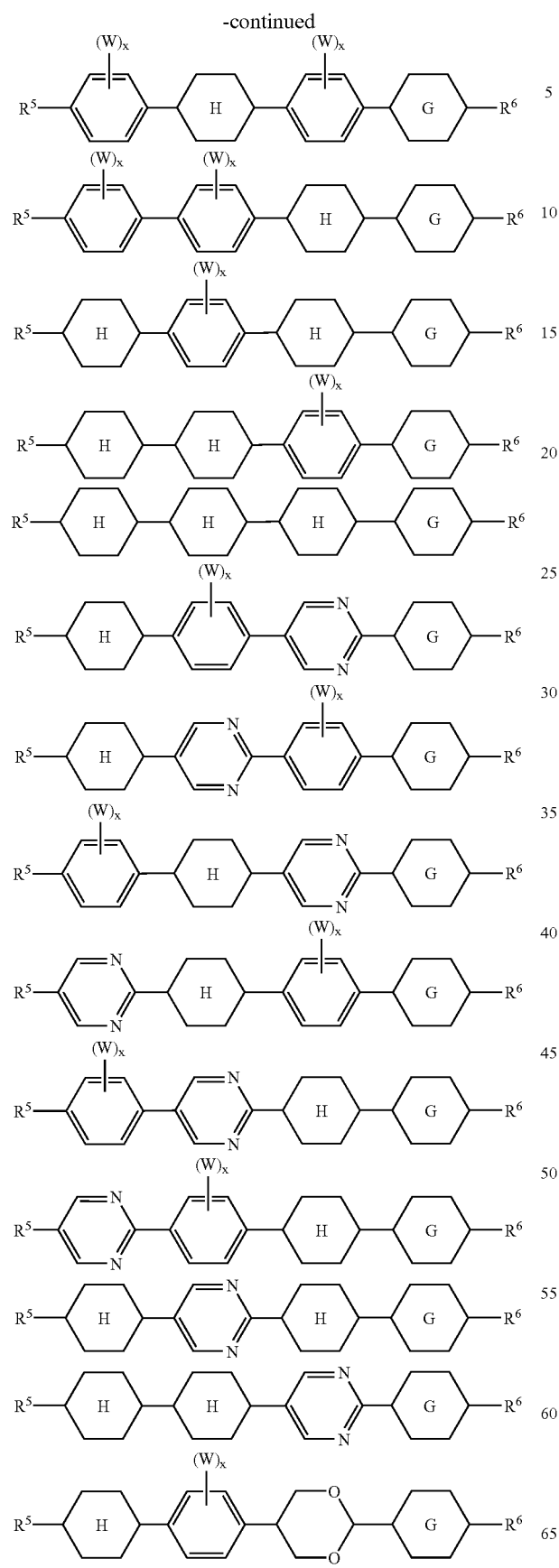
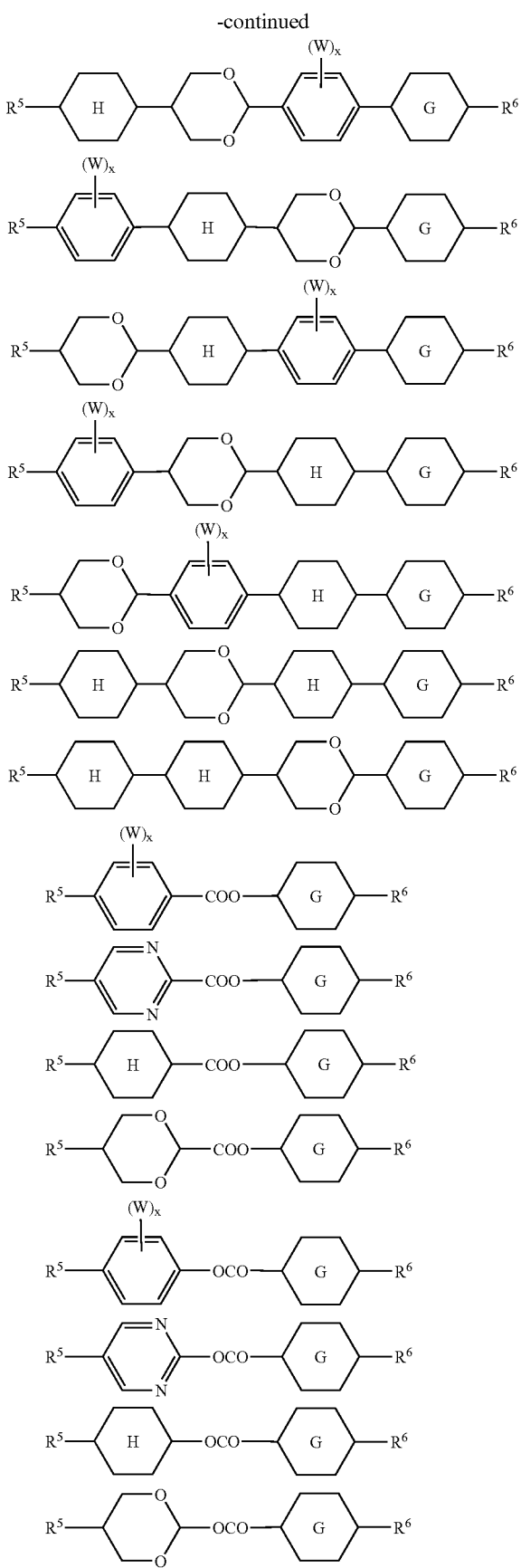

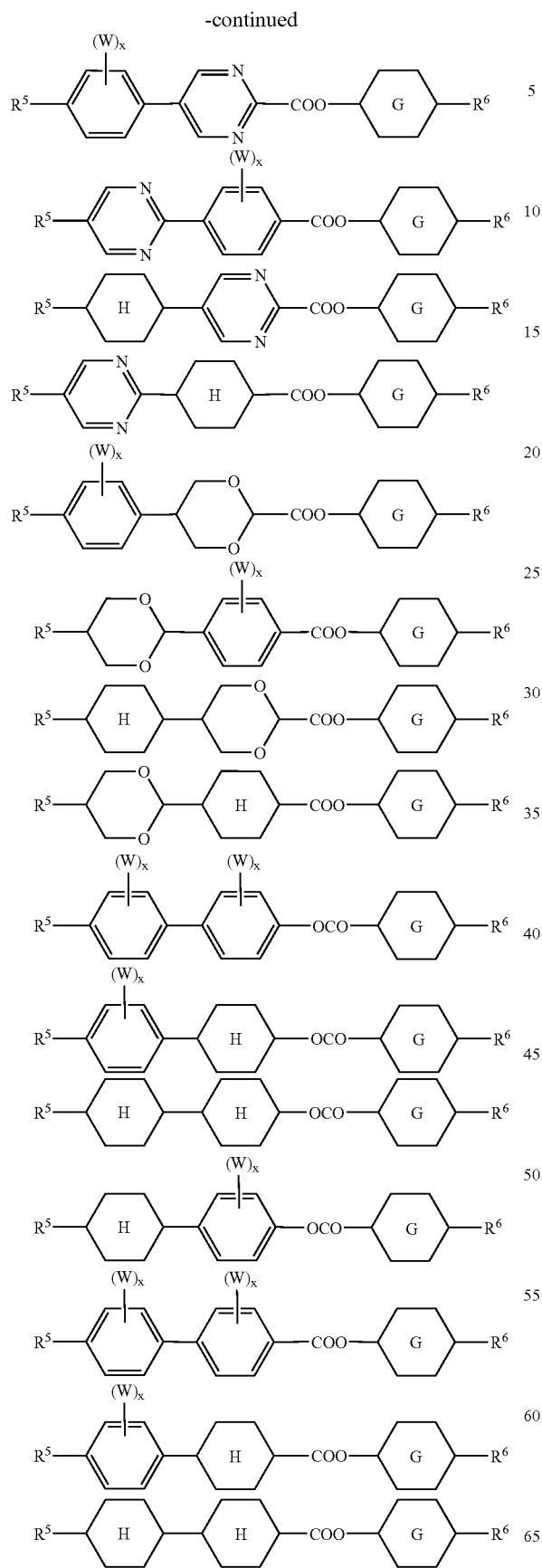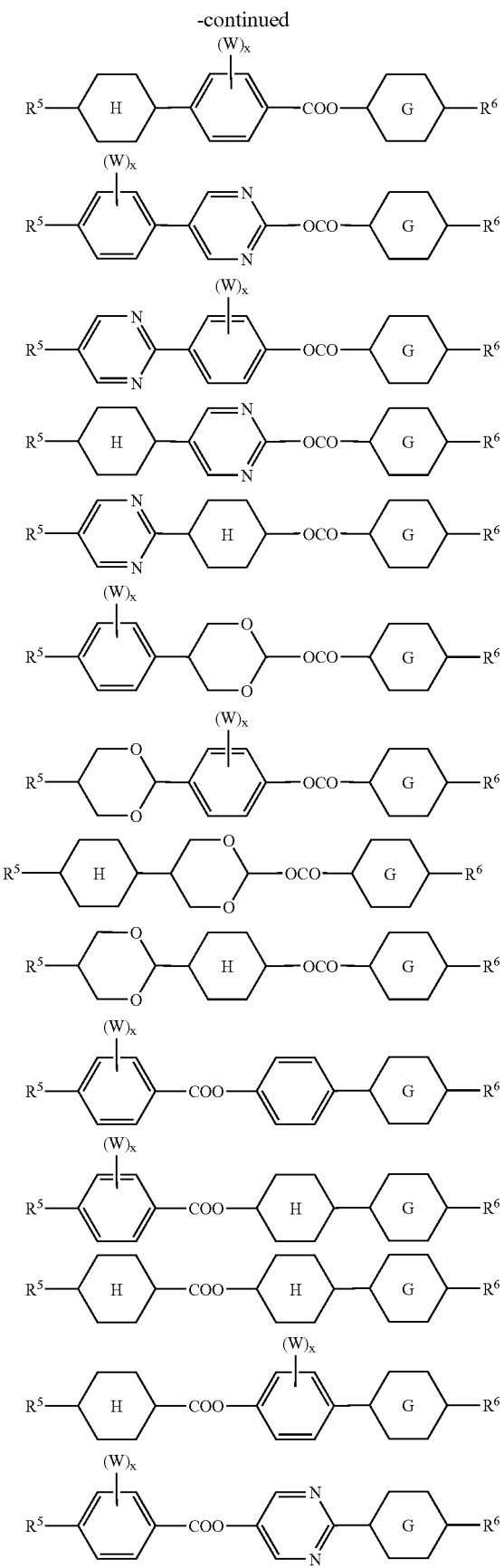

-continued
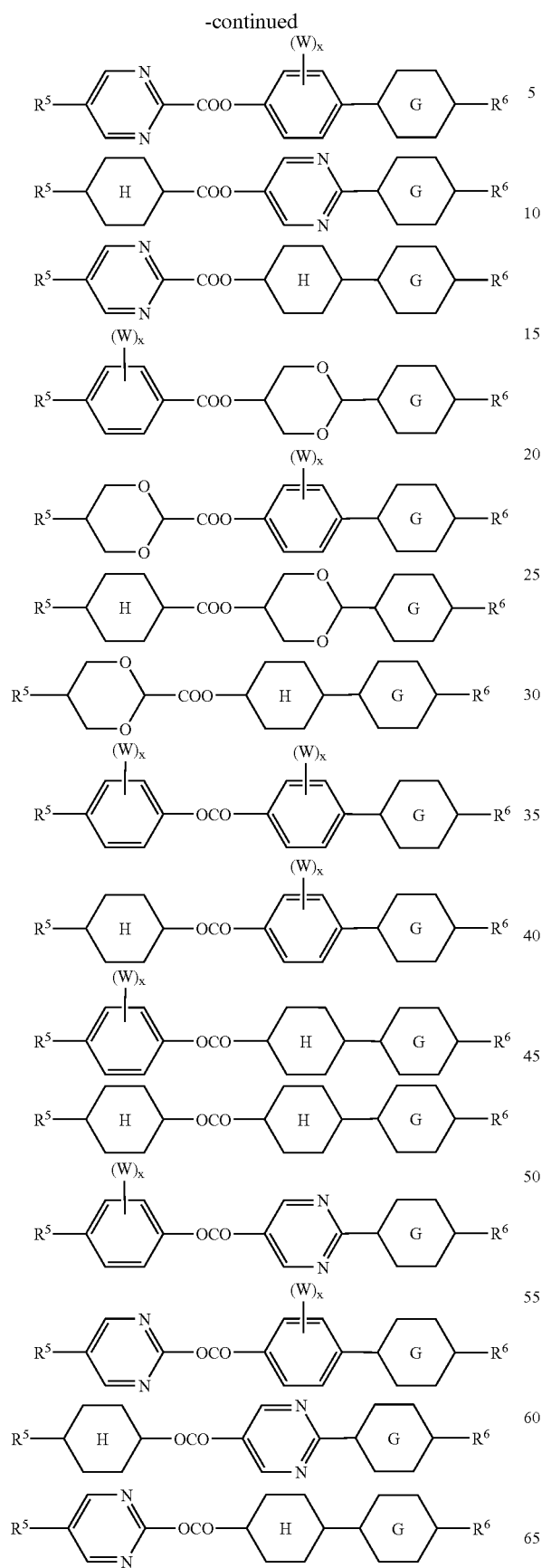
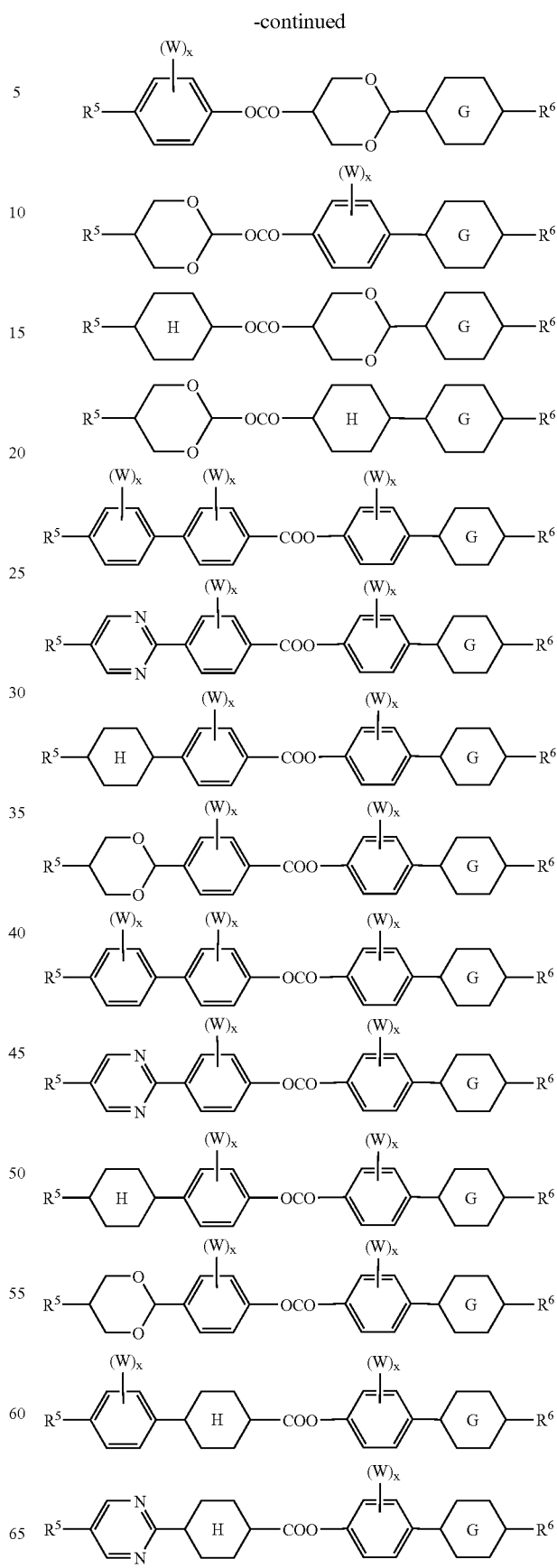

-continued
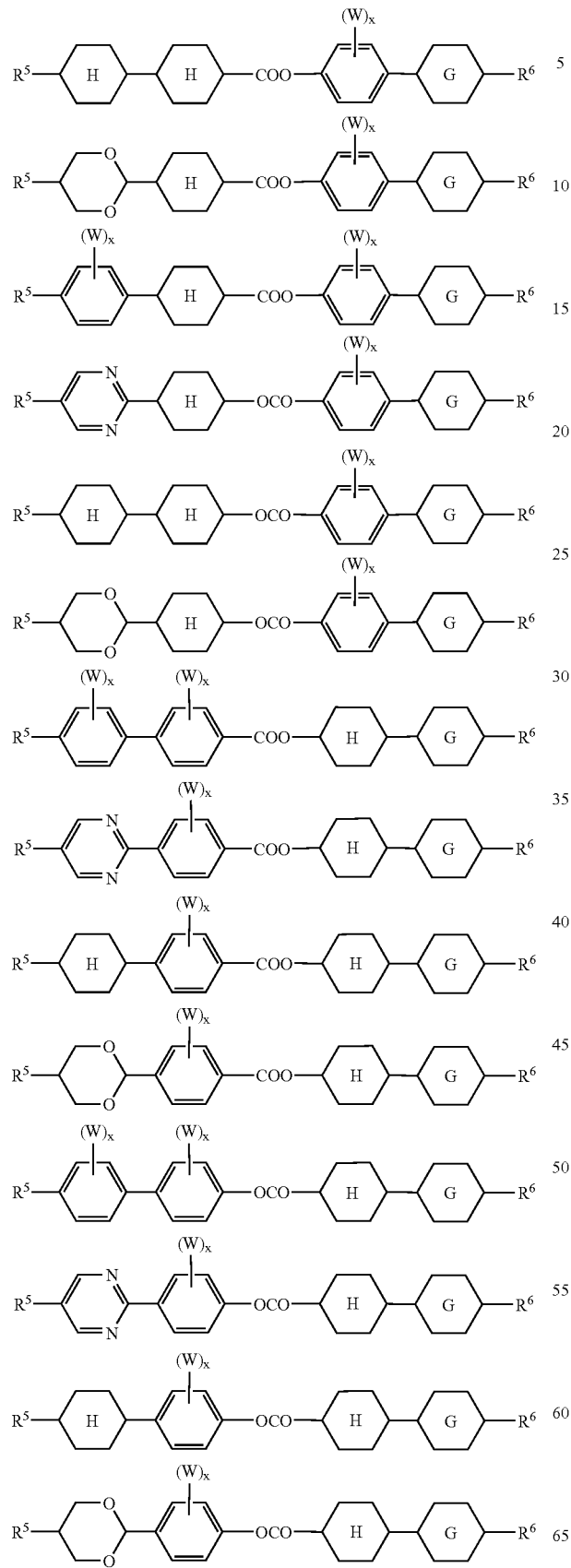
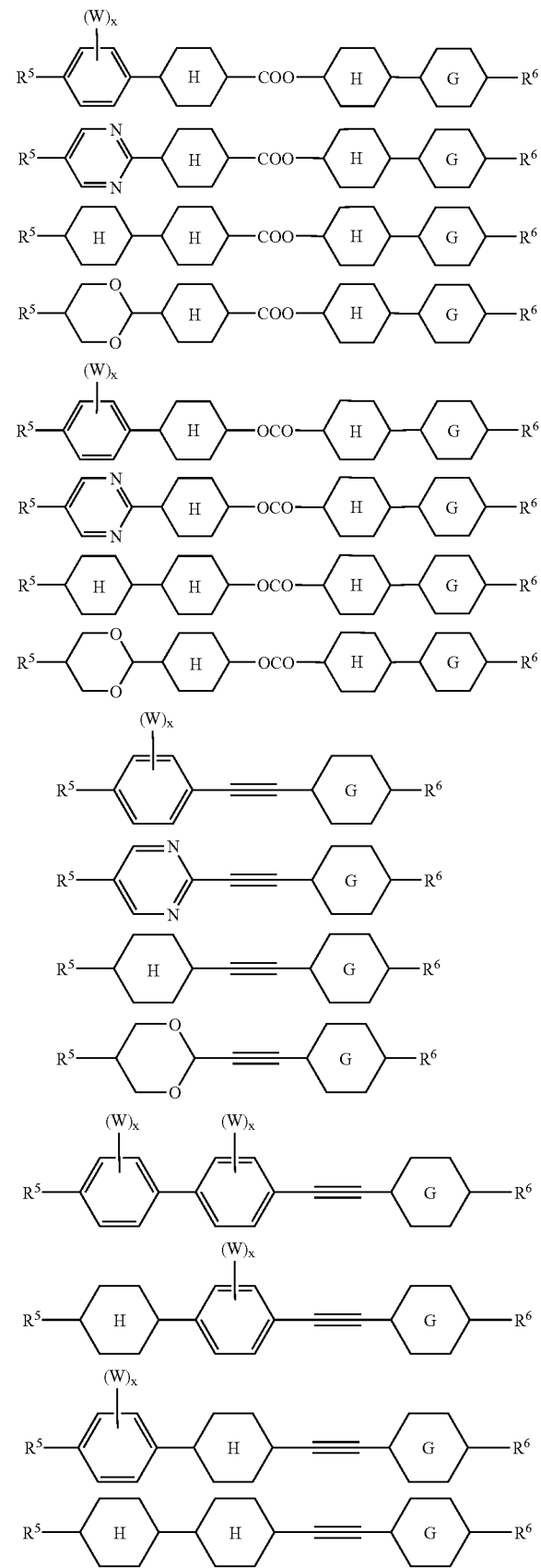

-continued
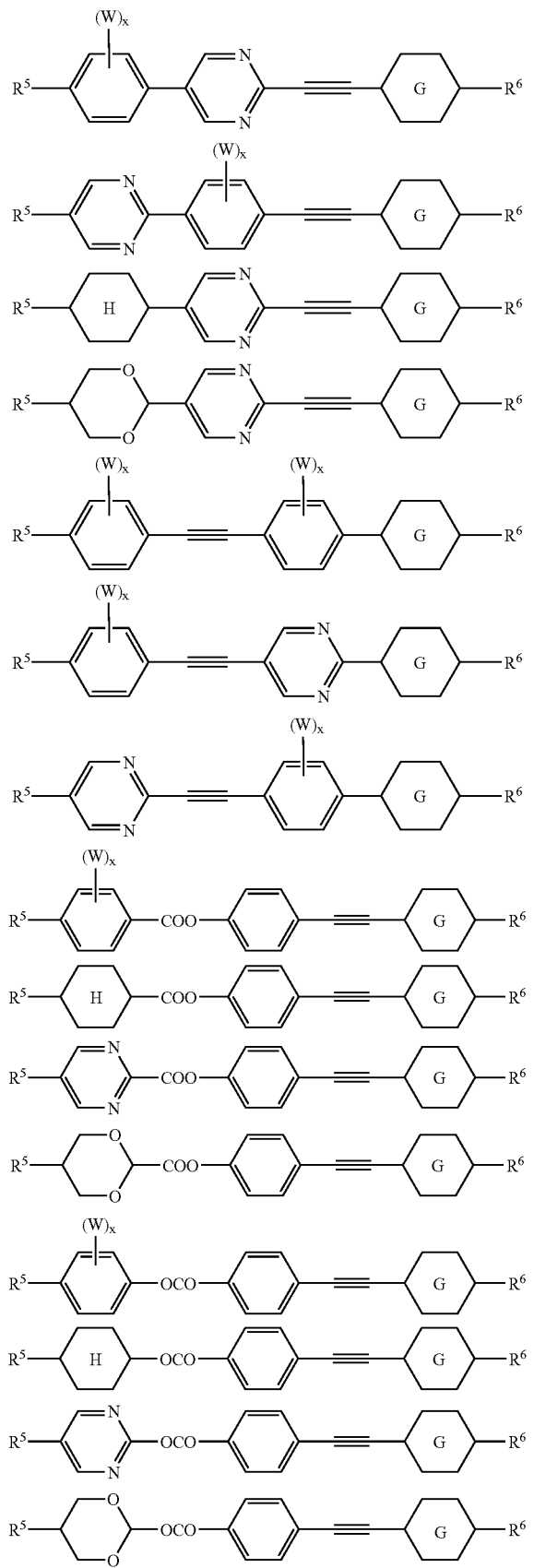
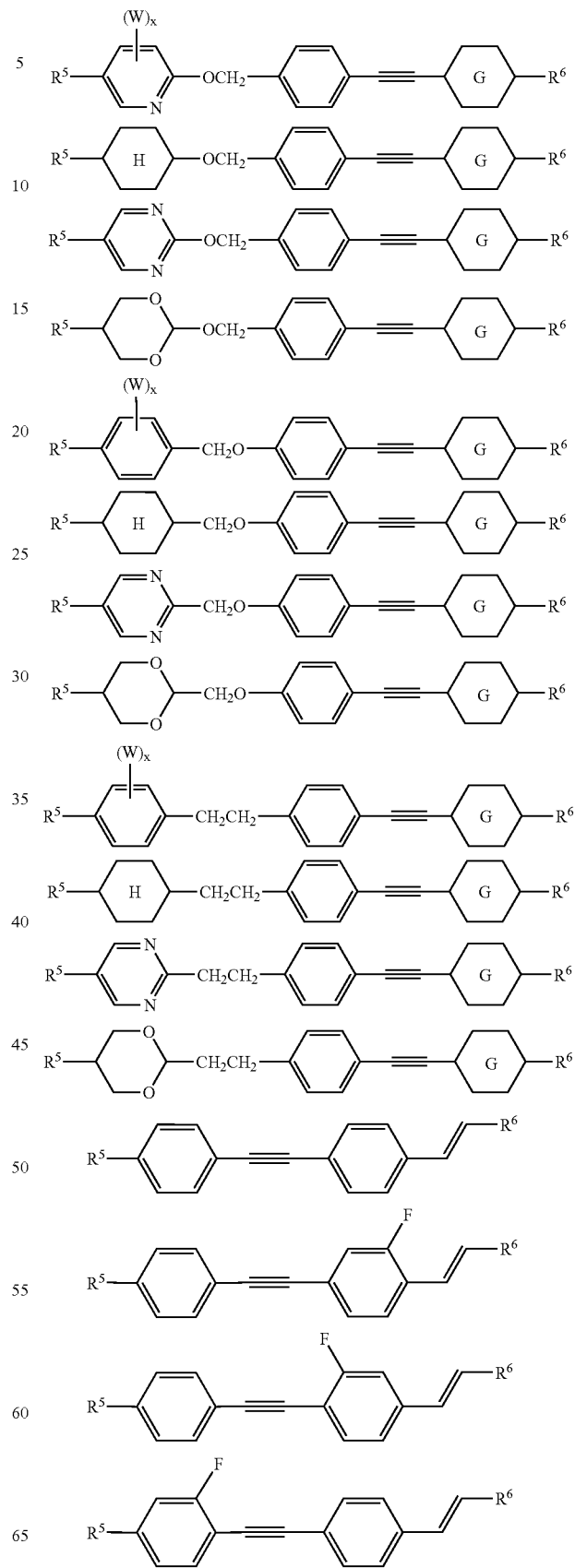

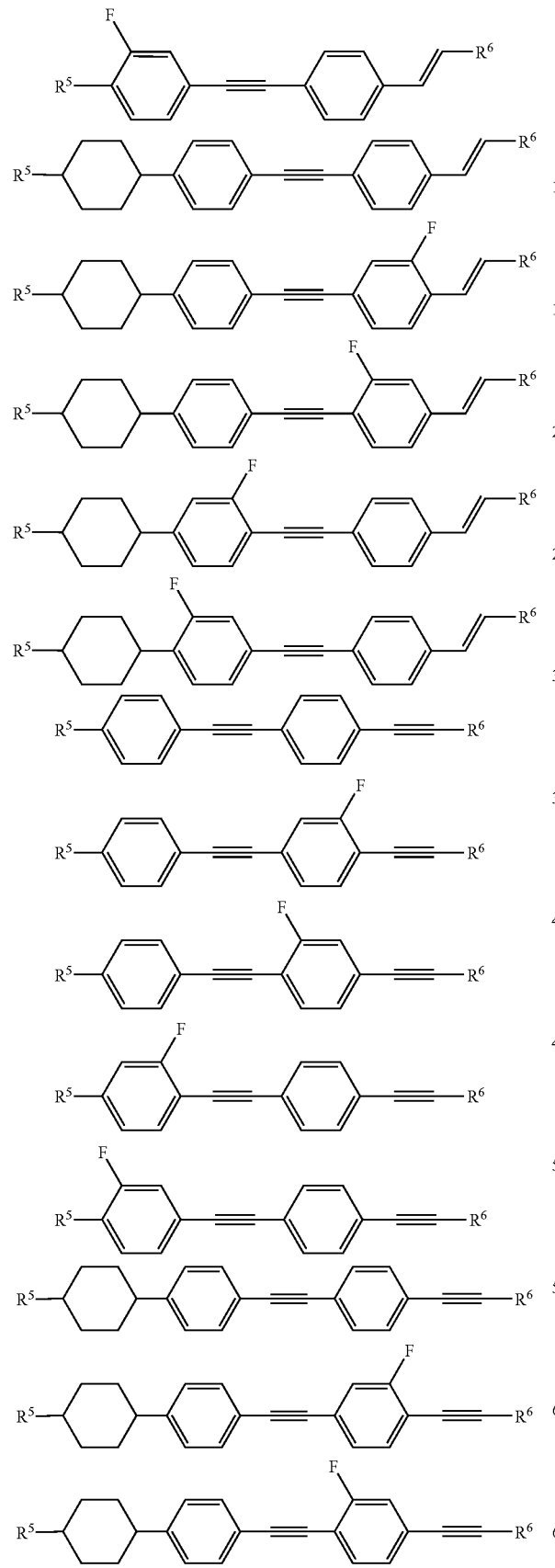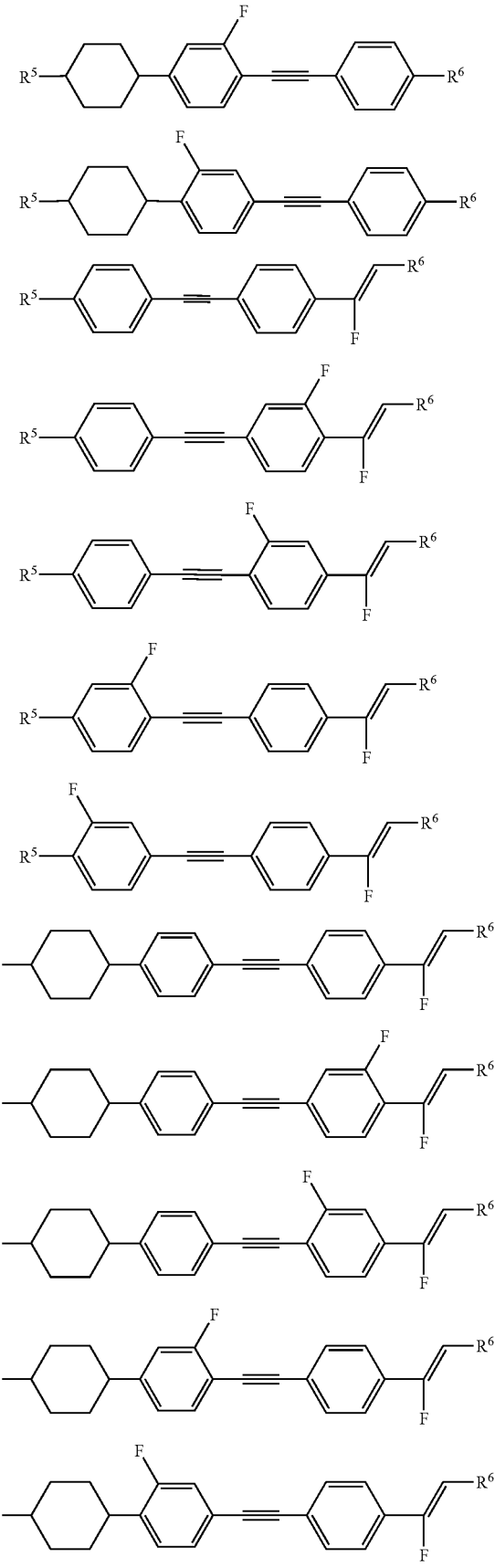

-continued

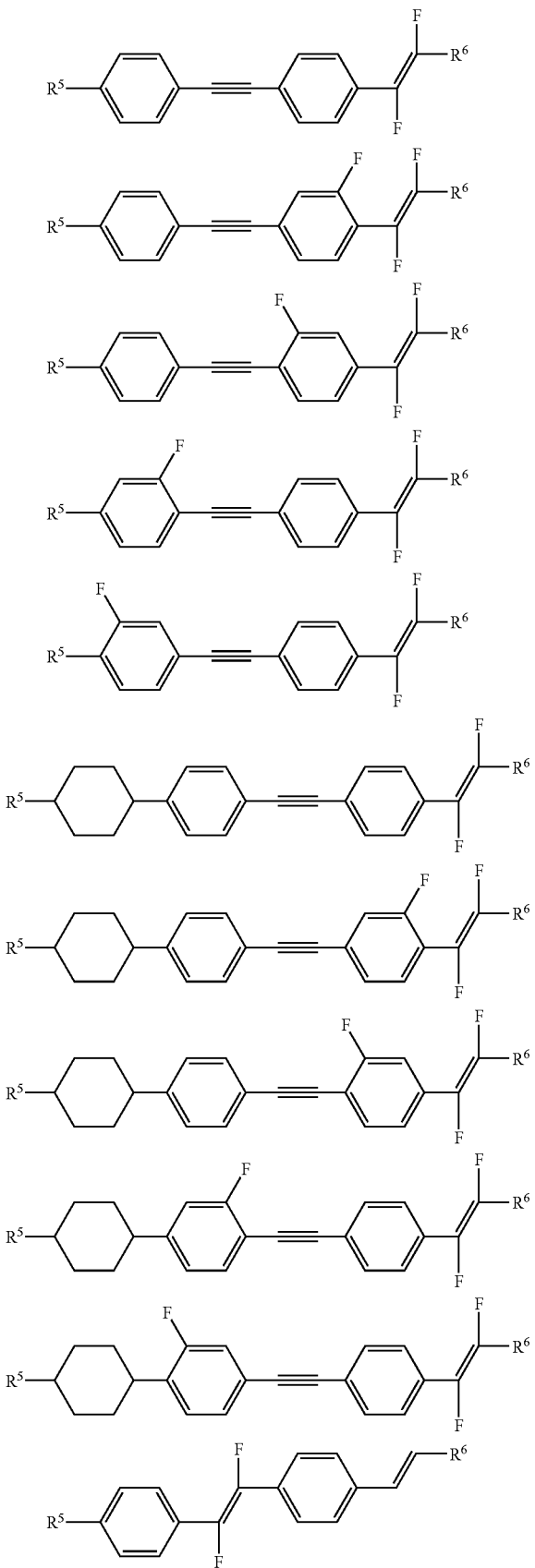

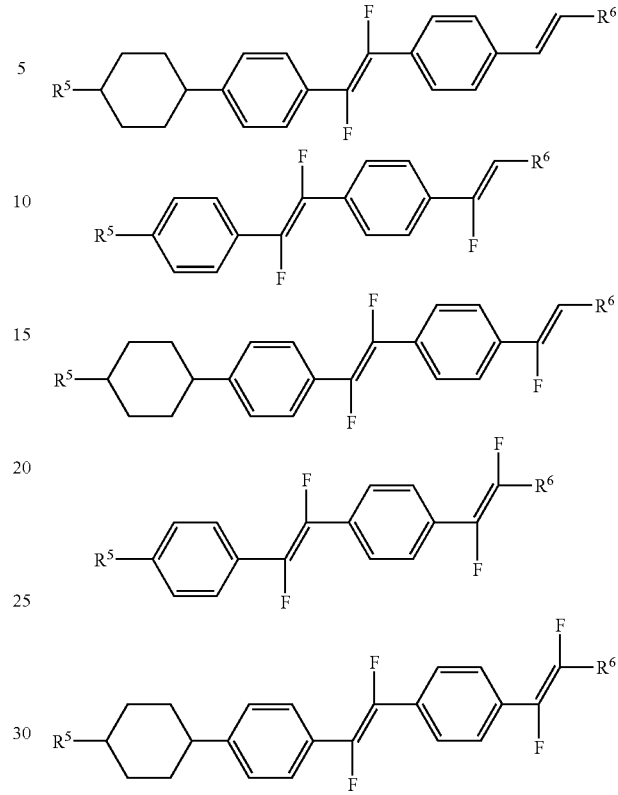

In the above formulae showing the examples of the compound represented by the formula (7), $R^5$ and $R^6$ correspond to $R^{51}$ and $R^{52}$ in the formula (7), respectively.

Examples of $R^5$ may include a hydrogen atom; or a methyl, ethyl, propyl, butyl, pentyl, hexyl, heptyl, octyl, nonyl, decyl, undecyl, dodecyl, ethenyl, propenyl, butenyl, pentenyl, hexenyl, heptenyl, octenyl, nonenyl, decenyl, undecenyl, dodecenyl, methoxy, ethoxy, propoxy, butoxy, pentyloxy, hexyloxy, heptyloxy, octyloxy, nonyloxy, decyloxy, undecyloxy, dodecyloxy, vinyloxy, propenyloxy, butenyloxy, pentenyloxy, hexenyloxy, heptenyloxy, octenyloxy, nonenyloxy, decenyloxy, propynyloxy, butynyloxy, pentynyloxy, hexynyloxy, heptynyloxy, octynyloxy, nonynyloxy, decynyloxy, undecynyloxy, dodecynyloxy, methoxymethyl, ethoxymethyl, propoxymethyl, butoxymethyl, pentyloxymethyl, hexyloxymethyl, heptyloxymethyl, octyloxymethyl, nonyloxymethyl, decyloxymethyl, methoxyethyl, ethoxyethyl, propoxyethyl, butoxyethyl, pentyloxyethyl, hexyloxyethyl, heptyloxyethyl, octyloxyethyl, nonyloxyethyl, decyloxyethyl, methoxypropyl, ethoxypropyl, propoxypropyl, butoxypropyl, pentyloxypropyl, hexyloxypropyl, heptyloxypropyl, octyloxypropyl, nonyloxypropyl, decyloxypropyl, methoxybutyl, ethoxybutyl, propoxybutyl, butoxybutyl, pentyloxybutyl, hexyloxybutyl, heptyloxybutyl, octyloxybutyl, nonyloxybutyl, decyloxybutyl, methoxypentyl, ethoxypentyl, propoxypentyl, butoxypentyl, pentyloxypentyl, hexyloxypentyl, heptyloxypentyl octyloxypentyl, nonyloxypentyl, or decyloxypentyl group optionally substituted with at least one fluorine atom. However, $R^5$ is not limited to the above examples.

Examples of $R^6$ may include a hydrogen atom; a fluorine atom; a fluoromethyl, difluoromethyl, trifluoromethyl, fluoromethoxy, difluoromethoxy, trifluoromethoxy, or cyano group; a methyl, ethyl, propyl, butyl, pentyl, hexyl, heptyl, octyl, nonyl, decyl, undecyl, dodecyl, ethenyl, propenyl, butenyl, pentenyl, hexenyl, heptenyl, octenyl, nonenyl, decenyl, undecenyl, dodecenyl, methoxy, ethoxy, propoxy, butoxy, pentyloxy, hexyloxy, heptyloxy, octyloxy, nonyloxy, decyloxy, undecyloxy, dodecyloxy, vinyloxy, propenyloxy, butenyloxy, pentenyloxy, hexenyloxy, heptenyloxy, octenyloxy, nonenyloxy, decenyloxy, propynyloxy, butynyloxy, pentynyloxy, hexynyloxy, heptynyloxy, octynyloxy, nonynyloxy, decynyloxy, undecynyloxy, dodecynyloxy, methoxymethyl, ethoxymethyl, propoxymethyl, butoxymethyl, pentyloxymethyl, hexyloxymethyl, heptyloxymethyl, octyloxymethyl, nonyloxymethyl, decyloxymethyl, methoxyethyl, ethoxyethyl, propoxyethyl, butoxyethyl, pentyloxyethyl, hexyloxyethyl, heptyloxyethyl, octyloxyethyl, nonyloxyethyl, decyloxyethyl, methoxypropyl, ethoxypropyl, propoxypropyl, butoxypropyl, pentyloxypropyl, hexyloxypropyl, heptyloxypropyl, octyloxypropyl, nonyloxypropyl, decyloxypropyl, methoxybutyl, ethoxybutyl, propoxybutyl, butoxybutyl, pentyloxybutyl, hexyloxybutyl, heptyloxybutyl, octyloxybutyl, nonyloxybutyl, decyloxybutyl, methoxypentyl, ethoxypentyl, propoxypentyl, butoxypentyl, pentyloxypentyl, hexyloxypentyl, heptyloxypentyl octyloxypentyl, nonyloxypentyl, or decyloxypentyl group optionally substituted with at least one fluorine atom; —OCH$_2$OCOCHCH$_2$, —OC$_2$H$_4$OCOCHCH$_2$, —OC$_3$H$_6$OCOCHCH$_2$, —OC$_4$H$_8$OCOCHCH$_2$, —OC$_5$H$_{10}$OOCOCHCH$_2$, —OC$_6$H$_{12}$OCOCHCH$_2$, —OC$_7$H$_{14}$OCOCHCH$_2$, —OC$_8$H$_{16}$OCOCHCH$_2$, —OC$_9$H$_{18}$OCOCHCH$_2$, —OC$_{10}$H$_{20}$OCOCHCH$_2$; —OCH$_2$OCOC(CH$_3$)CH$_2$, —OC$_2$H$_4$OCOC(CH$_3$)CH$_2$, —OC$_3$H$_6$OCOC(CH$_3$)CH$_2$, —OC$_4$H$_8$OCOC(CH$_3$)CH$_2$, —OC$_5$H$_{10}$OCOC(CH$_3$)CH$_2$, —OC$_6$H$_{12}$OCOC(CH$_3$)CH$_2$, —OC$_7$H$_{14}$OCOC(CH$_3$)CH$_2$, —OC$_8$H$_{16}$OCOC(CH$_3$)CH$_2$, —OC$_9$H$_{18}$OCOC(CH$_3$)CH$_2$, —OC$_{10}$H$_{20}$OCOC(CH$_3$)CH$_2$; —OCH$_2$CHCH$_2$, —OC$_2$H$_4$CHCH$_2$, —OC$_3$H$_6$CHCH$_2$, —OC$_4$H$_8$CHCH$_2$, —OC$_5$H$_{10}$CHCH$_2$, —OC$_6$H$_{12}$CHCH$_2$, —OC$_7$H$_{14}$CHCH$_2$, —OC$_8$H$_{16}$CHCH$_2$, —OC$_9$H$_{18}$CHCH$_2$, or —OC$_{10}$H$_{20}$CHCH$_2$. However, $R^6$ is not limited to these examples.

In the above formulae showing the examples of the compound represented by the formula (7), W stands for a hydrogen or fluorine atom, x denotes an integer of 0 to 3, Ring H stands for 1,4-cyclohexylene, and Ring G stands for 1,4-phenylene, 1,4-cyclohexylene, 1,4-cyclohexenylene, 4,1-cyclohexenylene, 2,5-cyclohexenylene, 5,2-cyclohexenylene, 3,6-cyclohexenylene, 6,3-cyclohexenylene, 2,5-pyrimidinediyl, 5,2-pyrimidinediyl, 2,5-pyridinediyl, 5,2-pyridinediyl, 2,5-dioxanediyl, or 5,2-dioxanediyl, optionally substituted with at least one fluorine atom. Among these, Ring G is preferably 1,4-cyclohexylene, 1,4-cyclohexenylene, 4,1-cyclohexenylene, 2,5-cyclohexenylene, 5,2-cyclohexenylene, 3,6-cyclohexenylene, or 6,3-cyclohexenylene.

In the liquid crystal composition of the present invention, a preferable content of the compound represented by the formula (1) or (2) is 1 to 99.9% by weight, preferably 5 to 99% by weight of the liquid crystal composition. The content of the compound represented by any of the formulae (4) to (7), if contained in the composition, may suitably be selected depending on the use of the composition. Further, a compound without a photopolymerizable functional group may also be contained, of which content may suitably be decided depending on the use of the composition, as long as the liquid crystallinity of the composition is not impaired. However, if a temperature-dependent change in the refractive index anisotropy of the composition is undesirable, the content of the compound without a photopolymerizable functional group is preferably be in the range of 0 to 50% by weight.

The liquid crystal composition of the present invention may contain a chiral compound for the purpose of producing a twisted oriented polymer. The chiral compound per se does not have to exhibit liquid crystallinity, nor does it have to have a polymerizable functional group. The chiral compound is not particularly limited, and may be selected from the following compounds. In the following formulae, the asterisk (*) indicates an asymmetric carbon. The content of the chiral compound in the composition may suitably be selected depending on the use of the liquid crystal composition, and not particularly limited.

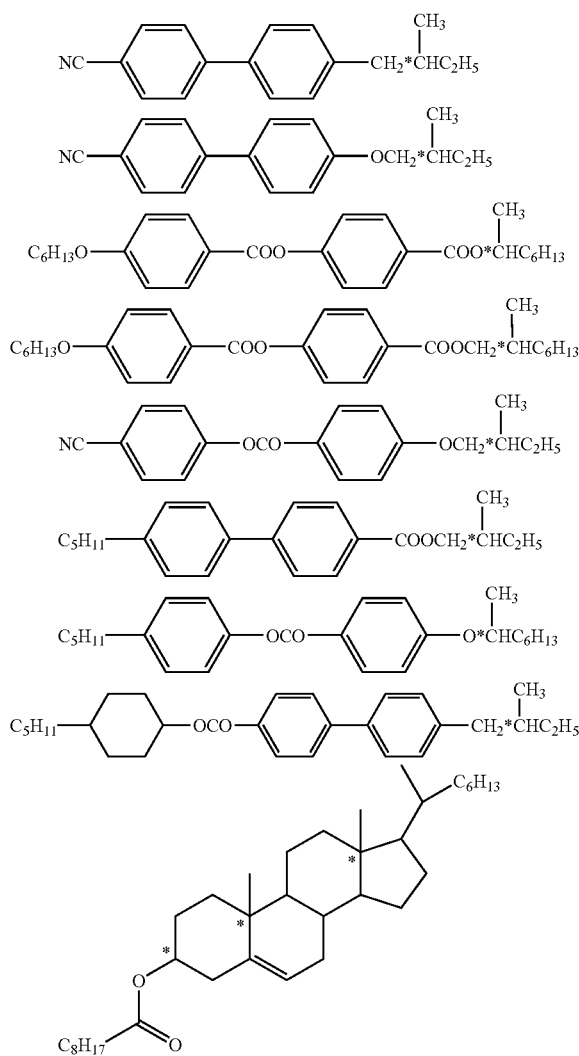

The liquid crystal composition of the present invention may contain a compound that has at least one photopolymerizable functional group and does not exhibit liquid crystallinity. Any such compounds may be used as long as the compounds are recognized in the art as polymerizable monomers or oligomers, and acrylate compounds, methacrylate compounds, and vinyl ether compounds are particularly preferred.

The liquid crystal composition of the present invention may further contain a thermal polymerization initiator or a photopolymerization initiator for the purpose of improving the polymerizability. Examples of the thermal polymerization initiator may include benzoyl peroxide and azobis (butyronitrile), and examples of the photopolymerization initiator may include benzoin ethers, benzophenones, acetophenones, and benzylketals. The amount of the polymerization initiator is preferably not more than 10% by weight, more preferably 0.5 to 1.5% by weight of the liquid crystal composition.

When the liquid crystal composition of the present invention is to be used for preparing, for example, polarizing films, printing inks, or paints, the composition may optionally contain pigments, coloring agents, or dyes depending on the use of the composition.

The liquid crystal composition of the present invention may contain at least one compound selected from the group consisting of the compounds of the present invention and polymers including homopolymers and copolymers of the present invention to be discussed later, and at least one monomer compound other than the compounds of the present invention selected from the group consisting of methacrylate esters, acrylate esters, epoxy, and vinyl ethers. Such liquid crystal composition of the present invention may further contain, for example, optional components that may be added as desired, such as the liquid crystalline compounds represented by the formulae (4) to (7).

The monomer compound mentioned above may be any compound usually recognized in the art as a polymerizable monomer, such as methacrylate esters, acrylate esters, epoxy, or vinyl ethers, but is not limited to these examples.

The content of each component of the liquid crystal composition of the present invention may suitably be selected depending on the use of the composition. It is preferred that the content of the at least one compound selected from the group consisting of the compounds and polymers of the present invention is 1 to 99% by weight, and the content of the monomer compound is 1 to 70% by weight.

The polymers of the present invention, including homopolymers and copolymers, are not particularly limited in molecular weight and the like properties, as long as they are polymers of one or more compounds represented by the formula (1), in particular polymers of one or more compounds represented by the formula (1) wherein at least one of $P^1$ and $P^2$ has an acrylate or methacrylate group on its terminal, polymers of one or more compounds represented by the formula (2), in particular polymers of one or more compounds represented by the formula (2) wherein at least one of $R^{11}$ and $R^{12}$ stands for a group represented by the formula (3), or polymers obtained by polymerization of the liquid crystal compositions mentioned above.

The polymers of the present invention may preferably be produced, for example, by photopolymerization by irradiation with energy beams such as ultraviolet rays or electron beams. A light source for effecting such photopolymerization may be those emitting either polarized or unpolarized light. When a polymerization initiator that absorbs light in the visible region is added to the liquid crystal material to be polymerized, irradiation may be performed with visible light. In this case, two laser beams may be caused to interfere with the visible light to thereby give spatially distributed intensity to the light beams. The irradiation temperature is preferably in the range for allowing maintenance of the liquid crystal state. When an optically anisotropic product is to be produced by photopolymerization, it is particularly preferred to effect the polymerization at a temperature as close to the room temperature as possible in order to avoid induction of unintended thermal polymerization.

The obtained polymers may further be subjected to a heat treatment for inhibition of initial change and steady maintenance of their characteristics. The heat treatment may preferably be carried out at approximately 50 to 200° C. for 30 seconds to 12 hours.

The optically anisotropic products of the present invention are not particularly limited as long as they have been produced using at least one material selected from the group consisting of the compounds, polymers, and liquid crystal compositions of the present invention. The optically anisotropic products may be prepared, for example, by polymerizing a liquid crystalline polymerizable component such as a compound or liquid crystal composition of the present invention, with liquid crystal molecules being aligned. More specifically, the products may be produced by polymerizing the polymerizable component carried on a substrate or held between substrates. The substrates used here may have been rubbed with a cloth on its surface, may have been provided with an organic thin film, for example, of polyimide formed on its surface, and rubbed with a cloth, or may have been provided with an alignment layer formed by obliquely evaporating $SiO_2$. It is convenient and preferred to use a substrate with an organic thin film formed thereon that has been rubbed with a cloth.

The substrate may be made of either an organic or inorganic material. Examples of the organic material may include polycarbonate, polyethylene terephthalate, polystyrene, polyvinyl chloride, polyalylate, triacetyl cellulose, and polysulfone. Examples of the inorganic material may include glass and silicone.

When the alignment of the liquid crystal molecules is controlled by an electric field, a substrate having an electrode layer may be used, on which layer the polyimide thin film is preferably formed. For alignment of the liquid crystal molecules, photo-alignment technique may also be used instead of the rubbing method. Alternatively, it is also possible to align the liquid crystal molecules by drawing following the polymerization of the material.

The optically anisotropic product may be produced by polymerization, preferably photopolymerization by irradiation with energy beams such as ultraviolet rays or electron beams. A light source for the photopolymerization may be a source of either polarized or unpolarized light. The temperature of the irradiation may be decided depending on the use of the product; it is sometimes preferred to effect the polymerization in a temperature range wherein the polymerizable components are maintained in the liquid crystal state, and in some other times in a temperature range wherein the polymerization components are in the isotropic phase.

The optically anisotropic products thus produced may be used as they are with the substrate, or only the polymer layer may be peeled off for use as an optically anisotropic product.

The optical or liquid crystal elements of the present invention are not particularly limited as long as they have been produced using at least one material selected from the group consisting of the compounds, polymers, and liquid crystal compositions of the present invention. Examples of the elements may include an element with a pair of electrode substrates holding at least one of the above materials therebetween, and an element having a structure similar to that of a conventional liquid crystal display device. The electrodes used for fabricating the optical or liquid crystal elements are not particularly limited in kind and shape, and any publicly known electrodes may be used. The optical or liquid crystal elements may be produced in accordance with a process for fabricating conventional elements, and other components may optionally be added as desired.

Dibenzothiophene compound (A-1) represented by the formula (A-1) above according to the present invention may be used for producing the compounds of the present invention or other liquid crystal materials. Dibenzothiophene compound (A-2) represented by the formula (A-2) above according to the present invention may be used for producing the dibenzothiophene compound (A-1). Dibenzothiophene oxide compound (A-3) represented by the formula (A-3) above according to the present invention may be used for producing the dibenzothiophene compound (A-2). Dibenzothiophene oxide compound (A-4) represented by the formula (A-4) according to the present invention may be used for producing the dibenzothiophene oxide compound (A-3). The dibenzothiophene oxide compound (A-4) may be prepared by oxidizing a dibenzothiophene compound (A-5) represented by the formula (A-5).

In the formulae (A-1) to (A-5), $A^1$ to $A^6$ each independently stands for a hydrogen atom, a fluorine atom, or an alkyl or alkoxy group having 1 to 10 carbon atoms optionally substituted with at least one fluorine atom, X stands for a halogen atom, and Y stands for a halogen atom or a hydroxyl group.

Examples of each of $A^1$ to $A^6$ may include a hydrogen atom; a fluorine atom; an alkyl group such as a methyl, ethyl, propyl, butyl, pentyl, hexyl, heptyl, octyl, nonyl, decyl, undecyl, or dodecyl group, or an alkyl group substituted with at least one fluorine atom, i.e. a fluoroalkyl group such as a trifluoromethyl or pentafluoroethyl group; or an alkoxy group such as a methoxy, ethoxy, propoxy, butoxy, pentyloxy, hexyloxy, octyloxy, nonyloxy, decyloxy, undecyloxy, or dodecyloxy group, or an alkoxy group substituted with at least one fluorine atom, i.e. a fluoroalkoxy group such as a methoxy group having 1 to 3 substituted fluorine atoms, or an ethoxy group having 1 to 5 substituted fluorine atoms.

Examples of the dibenzothiophene compound (A-1) of the present invention may include 7-chlorodibenzothiophene-3-ol, 7-bromodibenzothiophene-3-ol, 7-iododibenzothiophene-3-ol, 3,7-dichlorodibenzothiophene, 3-bromo-7-chlorodibenzothiophene, 3-chloro-7-iododibenzothiophene, 3,7-dibromodibenzothiophene, 3-bromo-7-iododibenzothiophene, 3,7-diiododibenzothiophene, 7-chloro-2-methyldibenzothiophene-3-ol, 7-bromo-2-methyldibenzothiophene-3-ol, 7-iodo-2-methyldibenzothiophene-3-ol, 3,7-dichloro-2-methyldibenzothiophene, 3-bromo-7-chloro-2-methyldibenzothiophene, 3-chloro-7-iodo-2-methyldibenzothiophene, 3,7-dibromo-2-methyldibenzothiophene, 3-bromo-7-iodo-2-methyldibenzothiophene, 3,7-diiodo-2-methyldibenzothiophene, 7-chloro-8-methyldibenzothiophene-3-ol, 7-bromo-8-methyldibenzothiophene-3-ol, 7-iodo-8-methyldibenzothiophene-3-ol, 3,7-dichloro-8-methyldibenzothiophene, 3-bromo-7-chloro-8-methyldibenzothiophene, 3-chloro-7-iodo-8-methyldibenzothiophene, 3,7-dibromo-8-methyldibenzothiophene, 3-bromo-7-iodo-8-methyldibenzothiophene, 3,7-diiodo-8-methyldibenzothiophene, 7-chloro-2,8-dimethyldibenzothiophene-3-ol, 7-bromo-2,8-dimethyldibenzothiophene-3-ol, 7-iodo-2,8-dimethyldibenzothiophene-3-ol, 3,7-dichloro-2,8-dimethyldibenzothiophene, 3-bromo-7-chloro-2,8-dimethyldibenzothiophene, 3-chloro-7-iodo-2,8-dimethyldibenzothiophene, 3,7-dibromo-2,8-dimethyldibenzothiophene, 3-bromo-7-iodo-2,8-dimethyldibenzothiophene, 3,7-diiodo-2,8-dimethyldibenzothiophene, 7-chloro-4-methyldibenzothiophene-3-ol, 7-bromo-4-methyldibenzothiophene-3-ol, 7-iodo-4-methyldibenzothiophene-3-ol, 3,7-dichloro-4-methyldibenzothiophene, 3-bromo-7-chloro-4-methyldibenzothiophene, 3-chloro-7-iodo-4-methyldibenzothiophene, 3,7-dibromo-4-methyldibenzothiophene, 3-bromo-7-iodo-4-methyldibenzothiophene, 3,7-diiodo-4-methyldibenzothiophene, 7-chloro-6-methyldibenzothiophene-3-ol, 7-bromo-6-methyldibenzothiophene-3-ol, 7-iodo-6-methyldibenzothiophene-3-ol, 3,7-dichloro-6-methyldibenzothiophene, 3-bromo-7-chloro-6-methyldibenzothiophene, 3-chloro-7-iodo-6-methyldibenzothiophene, 3,7-dibromo-6-methyldibenzothiophene, 3-bromo-7-iodo-6-methyldibenzothiophene, 3,7-diiodo-6-methyldibenzothiophene, 7-chloro-4,6-dimethyldibenzothiophene-3-ol, 7-bromo-4,6-dimethyldibenzothiophene-3-ol, 7-iodo-4,6-dimethyldibenzothiophene-3-ol, 3,7-dichloro-4,6-dimethyldibenzothiophene, 3-bromo-7-chloro-4,6-dimethyldibenzothiophene, 3-chloro-7-iodo-4,6-dimethyldibenzothiophene, 3,7-dibromo-4,6-dimethyldibenzothiophene, 3-bromo-7-iodo-4,6-dimethyldibenzothiophene, 3,7-diiodo-4,6-dimethyldibenzothiophene, 7-chloro-2,4-dimethyldibenzothiophene-3-ol, 7-bromo-2,4-dimethyldibenzothiophene-3-ol, 7-iodo-2,4-dimethyldibenzothiophene-3-ol, 3,7-dichloro-2,4-dimethyldibenzothiophene, 3-bromo-7-chloro-2,4-dimethyldibenzothiophene, 3-chloro-7-iodo-2,4-dimethyldibenzothiophene, 3,7-dibromo-2,4-dimethyldibenzothiophene, 7-chloro-2,6-dimethyldibenzothiophene-3-ol, 7-bromo-2,6-dimethyldibenzothiophene-3-ol, 7-iodo-2,6-dimethyldibenzothiophene-3-ol, 3,7-dichloro-2,6-dimethyldibenzothiophene, 3-bromo-7-chloro-2,6-dimethyldibenzothiophene, 3-chloro-7-iodo-2,6-dimethyldibenzothiophene, 3,7-dibromo-2,6-dimethyldibenzothiophene, 7-chloro-6,8-dimethyldibenzothiophene-3-ol, 7-bromo-6,8-dimethyldibenzothiophene-3-ol, 7-iodo-6,8-dimethyldibenzothiophene-3-ol, 3,7-dichloro-6,8-dimethyldibenzothiophene, 3-bromo-7-chloro-6,8-dimethyldibenzothiophene, 3-chloro-7-iodo-6,8-dimethyldibenzothiophene, 3,7-dibromo-6,8-dimethyldibenzothiophene, 7-chloro-4,8-dimethyldibenzothiophene-3-ol, 7-bromo-4,8-dimethyldibenzothiophene-3-ol, 7-iodo-4,8-dimethyldibenzothiophene-3-ol, 3,7-dichloro-4,8-dimethyldibenzothiophene, 3-bromo-7-chloro-4,8-dimethyldibenzothiophene, 3-chloro-7-iodo-4,8-dimethyldibenzothiophene, 3,7-dibromo-4,8-dimethyldibenzothiophene, 7-chloro-2,4,6,-trimethyldibenzothiophene-3-ol, 7-bromo-2,4,6-trimethyldibenzothiophene-3-ol, 7-iodo-2,4,6-trimethyldibenzothiophene-3-ol, 3,7-dichloro-2,4,6-trimethyldibenzothiophene, 3-bromo-7-chloro-2,4,6-trimethyldibenzothiophene, 3-chloro-7-iodo-2,4,6-trimethyldibenzothiophene, 3,7-dibromo-2,4,6,-trimethyldibenzothiophene, 7-chloro-2,4,8-trimethyldibenzothiophene-3-ol, 7-bromo-2,4,8-trimethyldibenzothiophene-3-ol, 7-iodo-2,4,8-trimethyldibenzothiophene-3-ol, 3,7-dichloro-2,4,8-trimethyldibenzothiophene, 3-bromo-7-chloro-2,4,8-trimethyldibenzothiophene, 3-chloro-7-iodo-2,4,8-trimethyldibenzothiophene, 3,7-dibromo-2,4,8-trimethyldibenzothiophene, 7-chloro-2,6,8-trimethyldibenzothiophene-3-ol, 7-bromo-2,6,8-trimethyldibenzothiophene-3-ol, 7-iodo-2,6,8-trimethyldibenzothiophene-3-ol, 3,7-dichloro-2,6,8,- trimethyldibenzothiophene, 3-bromo-7-chloro-2,6,8-trimethyldibenzothiophene, 3-chloro-7-iodo-2,6,8-trimethyldibenzothiophene, 3,7-dibromo-2,6,8-trimethyldibenzothiophene, 7-chloro-4,6,8-trimethyldibenzothiophene-3-ol, 7-bromo-4,6,8-trimethyldibenzothiophene-3-ol, 7-iodo-4,6,8-trimethyldibenzothiophene-3-ol, 3,7-dichloro-4,6,8-trimethyldibenzothiophene, 3-bromo-7-chloro-4,6,8-trimethyldibenzothiophene, 3-chloro-7-iodo-4,6,8-trimethyldibenzothiophene, 3,7-dibromo-4,6,8,-trimethyldibenzothiophene, 7-chloro-2,4,6,8-tetramethyldibenzothiophene-3-ol, 7-bromo-2,4,6,8-tetramethyldibenzothiophene-3-ol, 7-iodo-2,4,6,8-tetramethyldibenzothiophene-3-ol, 3,7-dichloro-2,4,6,8-tetramethyldibenzothiophene, 3-bromo-7-chloro-2,4,6,8-tetramethyldibenzothiophene, 3-chloro-7-iodo-2,4,6,8-tetramethyldibenzothiophene, 3,7-dibromo-2,4,6,8-tetramethyldibenzothiophene, 7-chloro-2-ethyldibenzothiophene-3-ol, 7-bromo-2-ethyldibenzothiophene-3-ol, 7-iodo-2-ethyldibenzothiophene-3-ol, 3,7-dichloro-2-ethyldibenzothiophene, 3-bromo-7-chloro-2-ethyldibenzothiophene, 3-chloro-7-iodo-2-ethyldibenzothiophene, 3,7-dibromo-2-ethyldibenzothiophene, 3-bromo-7-iodo-2-ethyldibenzothiophene, 3,7-diiodo-2-ethyldibenzothiophene, 7-chloro-8-ethyldibenzothiophene-3-ol, 7-bromo-8-ethyldibenzothiophene-3-ol, 7-iodo-8-ethyldibenzothiophene-3-ol, 3,7-dichloro-8-ethyldibenzothiophene, 3-bromo-7-chloro-8-ethyldibenzothiophene, 3-chloro-7-iodo-8-ethyldibenzothiophene, 3,7-dibromo-8-ethyldibenzothiophene, 3-bromo-7-iodo-8-ethyldibenzothiophene, 3,7-diiodo-8-ethyldibenzothiophene, 7-chloro-2,8-diethyldibenzothiophene-3-ol, 7-bromo-2,8-diethyldibenzothiophene-3-ol, 7-iodo-2,8-diethyldibenzothiophene-3-ol, 3,7-dichloro-2,8-diethyldibenzothiophene, 3-bromo-7-chloro-2,8-diethyldibenzothiophene, 3-chloro-7-iodo-2,8-diethyldibenzothiophene, 3,7-dibromo-2,8-diethyldibenzothiophene, 3-bromo-7-iodo-2,8-diethyldibenzothiophene, 3,7-diiodo-2,8-diethyldibenzothiophene, 7-chloro-4-ethyldibenzothiophene-3-ol, 7-bromo-4-ethyldibenzothiophene-3-ol, 7-iodo-4-ethyldibenzothiophene-3-ol, 3,7-dichloro-4-ethyldibenzothiophene, 3-bromo-7-chloro-4-ethyldibenzothiophene, 3-chloro-7-iodo-4-ethyldibenzothiophene, 3,7-dibromo-4-ethyldibenzothiophene, 3-bromo-7-iodo-4-ethyldibenzothiophene, 3,7-diiodo-4-ethyldibenzothiophene, 7-chloro-6-ethyldibenzothiophene-3-ol, 7-bromo-6-ethyldibenzothiophene-3-ol, 7-iodo-6-ethyldibenzothiophene-3-ol, 3,7-dichloro-6-ethyldibenzothiophene, 3-bromo-7-chloro-6-ethyldibenzothiophene, 3-chloro-7-iodo-6-ethyldibenzothiophene, 3,7-dibromo-6-ethyldibenzothiophene, 3-bromo-7-iodo-6-ethyldibenzothiophene, 3,7-diiodo-6-ethyldibenzothiophene, 7-chloro-4,6-diethyldibenzothiophene-3-ol, 7-bromo-4,6-diethyldibenzothiophene-3-ol, 7-iodo-4,6-diethyldibenzothiophene-3-ol, 3,7-dichloro-4,6-diethyldibenzothiophene, 3-bromo-7-chloro-4,6-diethyldibenzothiophene, 3-chloro-7-iodo-4,6-diethyldibenzothiophene, 3,7-dibromo-4,6-diethyldibenzothiophene, 3-bromo-7-iodo-4,6-diethyldibenzothiophene, 3,7-diiodo-4,6-diethyldibenzothiophene, 7-chloro-2,4-diethyldibenzothiophene-3-ol, 7-bromo-2,4-diethyldibenzothiophene-3-ol, 7-iodo-2,4-diethyldibenzothiophene-3-ol, 3,7-dichloro-2,4-diethyldibenzothiophene, 3-bromo-7-chloro-2,4-diethyldibenzothiophene, 3-chloro-7-iodo-2,4-diethyldibenzothiophene, 3,7-dibromo-2,4-diethyldibenzothiophene, 7-chloro-2,6-diethyldibenzothiophene-3-ol, 7-bromo-2,6-diethyldibenzothiophene-3-ol, 7-iodo-2,6-diethyldibenzothiophene-3-ol, 3,7-dichloro-2,6-diethyldibenzothiophene, 3-bromo-7-chloro-2,6-diethyldibenzothiophene, 3-chloro-7-iodo-2,6-diethyldibenzothiophene, 3,7-dibromo-2,6-diethyldibenzothiophene, 7-chloro-6,8-diethyldibenzothiophene-3-ol, 7-bromo-6,8-diethyldibenzothiophene-3-ol, 7-iodo-6,8-diethyldibenzothiophene-3-ol, 3,7-dichloro-6,8-diethyldibenzothiophene, 3-bromo-7-chloro-6,8-diethyldibenzothiophene, 3-chloro-7-iodo-6,8-diethyldibenzothiophene, 3,7-dibromo-6,8-diethyldibenzothiophene, 7-chloro-4,8-diethyldibenzothiophene-3-ol, 7-bromo-4,8-diethyldibenzothiophene-3-ol, 7-iodo-4,8-diethyldibenzothiophene-3-ol, 3,7-dichloro-4,8-diethyldibenzothiophene, 3-bromo-7-chloro-4,8-diethyldibenzothiophene, 3-chloro-7-iodo-4,8-diethyldibenzothiophene, 3,7-dibromo-4,8-diethyldibenzothiophene, 7-chloro-2,4,6-triethyldibenzothiophene-3-ol, 7-bromo-2,4,6-triethyldibenzothiophene-3-ol, 7-iodo-2,4,6-triethyldibenzothiophene-3-ol, 3,7-dichloro-2,4,6-triethyldibenzothiophene, 3-bromo-7-chloro-2,4,6-triethyldibenzothiophene, 3-chloro-7-iodo-2,4,6-triethyldibenzothiophene, 3,7-dibromo-2,4,6-triethyldibenzothiophene, 7-chloro-2,4,8-triethyldibenzothiophene-3-ol, 7-bromo-2,4,8-triethyldibenzothiophene-3-ol, 7-iodo-2,4,8-triethyldibenzothiophene-3-ol, 3,7-dichloro-2,4,8-triethyldibenzothiophene, 3-bromo-7-chloro-2,4,8-triethyldibenzothiophene, 3-chloro-7-iodo-2,4,8-triethyldibenzothiophene, 3,7-dibromo-2,4,8-triethyldibenzothiophene, 7-chloro-2,6,8-triethyldibenzothiophene-3-ol, 7-bromo-2,6,8-triethyldibenzothiophene-3-ol, 7-iodo-2,6,8-triethyldibenzothiophene-3-ol, 3,7-dichloro-2,6,8-triethyldibenzothiophene, 3-bromo-7-chloro-2,6,8-triethyldibenzothiophene, 3-chloro-7-iodo-2,6,8-triethyldibenzothiophene, 3,7-dibromo-2,6,8-triethyldibenzothiophene, 7-chloro-4,6,8-triethyldibenzothiophene-3-ol, 7-bromo-4,6,8-triethyldibenzothiophene-3-ol, 7-iodo-4,6,8-triethyldibenzothiophene-3-ol, 3,7-dichloro-4,6,8-triethyldibenzothiophene, 3-bromo-7-chloro-4,6,8-triethyldibenzothiophene, 3-chloro-7-iodo-4,6,8-triethyldibenzothiophene, 3,7-dibromo-4,6,8-triethyldibenzothiophene, 7-chloro-2,4,6,8-tetraethyldibenzothiophene-3-ol, 7-bromo-2,4,6,8-tetraethyldibenzothiophene-3-ol, 7-iodo-2,4,6,8-tetraethyldibenzothiophene-3-ol, 3,7-dichloro-2,4,6,8-tetraethyldibenzothiophene, 3-bromo-7-chloro-2,4,6,8-tetraethyldibenzothiophene, 3-chloro-7-iodo-2,4,6,8-tetraethyldibenzothiophene, 3,7-dibromo-2,4,6,8-tetraethyldibenzothiophene, 7-chloro-2-trifluoromethyldibenzothiophene-3-ol, 7-bromo-2-trifluoromethyldibenzothiophene-3-ol, 7-iodo-2- trifluoromethyldibenzothiophene-3-ol, 3,7-dichloro-2-trifluoromethyldibenzothiophene, 3-bromo-7-chloro-2-trifluoromethyldibenzothiophene, 3-chloro-7-iodo-2-trifluoromethyldibenzothiophene, 3,7-dibromo-2-trifluoromethyldibenzothiophene, 3-bromo-7-iodo-2-trifluoromethyldibenzothiophene, 3,7-diiodo-2-trifluoromethyldibenzothiophene, 7-dhloro-8-trifluoromethyldibenzothiophene-3-ol, 7-bromo-8-trifluoromethyldibenzothiophene-3-ol, 7-iodo-8-trifluoromethyldibenzothiophene-3-ol, 3,7-dichloro-8-trifluoromethyldibenzothiophene, 3-bromo-7-chloro-8-trifluoromethyldibenzothiophene, 3-chloro-7-iodo-8-trifluoromethyldibenzothiophene, 3,7-dibromo-8-trifluoromethyldibenzothiophene, 3-bromo-7-iodo-8-trifluoromethyldibenzothiophene, 3,7-diiodo-8-trifluoromethyldibenzothiophene, 7-chloro-2,8-bis(trifluoromethyl)dibenzothiophene-3-ol, 7-bromo-2,8-bis(trifluoromethyl)dibenzothiophene-3-ol, 7-iodo-2,8-bis(trifluoromethyl)dibenzothiophene-3-ol, 3,7-dichloro-2,8-bis(trifluoromethyl)dibenzothiophene, 3-bromo-7-chloro-2,8-bis(trifluoromethyl)dibenzothiophene, 3-chloro-7-iodo-2,8-bis(trifluoromethyl)dibenzothiophene, 3,7-dibromo-2,8-bis(trifluoromethyl)dibenzothiophene, 3-bromo-7-iodo-2,8-bis(trifluoromethyl)dibenzothiophene, 3,7-diiodo-2,8-bis(trifluoromethyl)dibenzothiophene, 7-chloro-4-trifluoromethyldibenzothiophene-3-ol, 7-bromo-4-trifluoromethyldibenzothiophene-3-ol, 7-iodo-4-trifluoromethyldibenzothiophene-3-ol, 3,7-dichloro-4-trifluoromethyldibenzothiophene, 3-bromo-7-chloro-4-trifluoromethyldibenzothiophene, 3-chloro-7-iodo-4-trifluoromethyldibenzothiophene, 3,7-dibromo-4-trifluoromethyldibenzothiophene, 3-bromo-7-iodo-4-trifluoromethyldibenzothiophene, 3,7-diiodo-4-trifluoromethyldibenzothiophene, 7-chloro-6-trifluoromethyldibenzothiophene-3-ol, 7-bromo-6-trifluoromethyldibenzothiophene-3-ol, 7-iodo-6-trifluoromethyldibenzothiophene-3-ol, 3,7-dichloro-6-trifluoromethyldibenzothiophene, 3-bromo-7-chloro-6-trifluoromethyldibenzothiophene, 3-chloro-7-iodo-6-trifluoromethyldibenzothiophene, 3,7-dibromo-6-trifluoromethyldibenzotiophene, 3-bromo-7-iodo-6-trifluoromethyldibenzothiophene, 3,7-diiodo-6-trifluoromethyldibenzothiophene, 7-chloro-4,6-bis(trifluoromethyl)dibenzothiophene-3-ol, 7-bromo-4,6-bis(trifluoromethyl)dibenzothiophene-3-ol, 7-iodo-4,6-bis(trifluoromethyl)dibenzothiophene-3-ol, 3,7-dichloro-4,6-bis(trifluoromethyl)dibenzothiophene, 3-bromo-7-chloro-4,6-bis(trifluoromethyl)dibenzothiophene, 3-chloro-7-iodo-4,6-bis(trifluoromethyl)dibenzothiophene, 3,7-dibromo-4,6-bis(trifluoromethyl)dibenzothiophene, 3-bromo-7-iodo-4,6-bis(trifluoromethyl)dibenzothiophene, 3,7-diiodo-4,6-bis(trifluoromethyl)dibenzothiophene, 7-chloro-2,4-bis(trifluoromethyl)dibenzothiophene-3-ol, 7-bromo-2,4-bis(trifluoromethyl)dibenzothiophene-3-ol, 7-iode-2,4-bis(trifluoromethyl)dibenzothiophene-3-ol, 3,7-dichloro-2,4-bis(trifluoromethyl)dibenzothiophene, 3-bromo-7-chloro-2,4-bis(trifluoromethyl)dibenzothiophene, 3-chloro-7-iodo-2,4-bis(trifluoromethyl)dibenzothiophene, 3,7-dibromo-2,4-bis(trifluoromethyl)dibenzothiophene, 7-chloro-2,6-bis(trifluoromethyl)dibenzothiophene-3-ol, 7-bromo-2,6-bis(trifluoromethyl)dibenzothiophene-3-ol, 7-iodo-2,6-bis(trifluoromethyl)dibenzothiophene-3-ol, 3,7-dichloro-2,6-bis(trifluoromethyl)dibenzothiophene, 3-bromo-7-chloro-2,6-bis(trifluoromethyl)dibenzothiophene, 3-chloro-7-iodo-2,6-bis(trifluoromethyl)dibenzothiophene, 3,7-dibromo-2,6-bis(trifluoromethyl)dibenzothiophene, 7-chloro-6,8-bis(trifluoromethyl)dibenzothiophene-3-ol, 7-bromo-6,8-bis(trifluoromethyl)dibenzothiophene-3-ol, 7-iodo-6,8-bis(trifluoromethyl)dibenzothiophene-3-ol, 3,7-dichloro-6,8-bis(trifluoromethyl)dibenzothiophene, 3-bromo-7-chloro-6,8-bis(trifluoromethyl)dibenzothiophene, 3-chloro-7-iodo-6,8-bis(trifluoromethyl)dibenzothiophene, 3,7-dibromo-6,8-bis(trifluoromethyl)dibenzothiophene, 7-chloro-4,8-bis(trifluoromethyl)dibenzothiophene-3-ol, 7-bromo-4,8-bis(trifluoromethyl)dibenzothiophene-3-ol, 7-iodo-4,8-bis(trifluoromethyl)dibenzothiophene-3-ol, 3,7-dichloro-4,8-bis(trifluoromethyl)dibenzothiophene, 3-bromo-7-chloro-4,8-bis(trifluoromethyl)dibenzothiophene, 3-chloro-7-iodo-4,8-bis(trifluoromethyl)dibenzothiophene, 3,7-dibromo-4,8-bis(trifluoromethyl)dibenzothiophene, 7-chloro-2,4,6-tris(trifluoromethyl)dibenzothiophene-3-ol, 7-bromo-2,4,6-tris(trifluoromethyl)dibenzothiophene-3-ol, 7-iodo-2,4,6-tris(trifluoromethyl)dibenzothiophene-3-ol, 3,7-dichloro-2,4,6-tris(trifluoromethyl)dibenzothiophene, 3-bromo-7-chloro-2,4,6-tris(trifluoromethyl)dibenzothiophene, 3-chloro-7-iodo-2,4,6-tris(trifluoromethyl)dibenzothiophene, 3,7-dibromo-2,4,6-tris(trifluoromethyl)dibenzothiophene, 7-chloro-2,4,8-tris(trifluoromethyl)dibenzothiophene-3-ol, 7-bromo-2,4,8-tris(trifluoromethyl)dibenzothiophene-3-ol, 7-iodo-2,4,8-tris(trifluoromethyl)dibenzothiophene-3-ol, 3,7-dichloro-2,4,8-tris(trifluoromethyl)dibenzothiophene, 3-bromo-7-chloro-2,4,8-tris(trifluoromethyl)dibenzothiophene, 3-chloro-7-iodo-2,4,8-tris(trifluoromethyl)dibenzothiophene, 3,7-dibromo-2,4,8-tris(trifluoromethyl)dibenzothiophene, 7-chloro-2,6,8-tris(trifluoromethyl)dibenzothiophene-3-ol, 7-bromo-2,6,8-tris(trifluoromethyl)dibenzothiophene-3-ol, 7-iodo-2,6,8-tris(trifluoromethyl)dibenzothiophene-3-ol, 3,7-dichloro-2,6,8-tris(trifluoromethyl)dibenzothiophene, 3-bromo-7-chloro-2,6,8-tris(trifluoromethyl)dibenzothiophene, 3-chloro-7-iodo-2,6,8-tris(trifluoromethyl)dibenzothiophene, 3,7-dibromo-2,6,8-tris(trifluoromethyl)dibenzothiophene, 7-chloro-4,6,8-tris(trifluoromethyl)dibenzothiophene-3-ol, 7-bromo-4,6,8-tris(trifluoromethyl)dibenzothiophene-3-ol, 7-iodo-4,6,8-tris(trifluoromethyl)dibenzothiophene-3-ol, 3,7-dichloro-4,6,8-tris(trifluoromethyl)dibenzothiophene, 3-bromo-7-chloro-4,6,8-tris(trifluoromethyl)dibenzothiophene, 3-chloro-7-iodo-4,6,8-tris(trifluoromethyl)dibenzothiophene, 3,7-dibromo-4,6,8-tris(trifluoromethyl)dibenzothiophene, 7-chloro-2,4,6,8-tetrakis(trifluoromethyl)dibenzothiophene-3-ol, 7-bromo-2,4,6,8-tetrakis(trifluoromethyl)dibenzothiophene-3-ol, 7-iodo-2,4,6,8-tetrakis(trifluoromethyl)dibenzothiophene-3-ol, 3,7-dichloro-2,4,6,8-tetrakis(trifluoromethyl)dibenzothiophene, 3-bromo-7-chloro-2,4,6,8-tetrakis(trifluoromethyl)dibenzothiophene, 3-chloro-7-iodo-2,4,6,8-tetrakis(trifluoromethyl)dibenzothiophene, and 3,7-dibromo-2,4,6,8-tetrakis(trifluoromethyl)dibenzothiophene.

The dibenzothiophene compound (A-1) of the present invention may be prepared by diazotizing a dibenzothiophene compound (A-2) to obtain a diazonium salt, and decomposing the diazonium salt in the presence of an anion Y corresponding to Y in the formula (A-1).

The diazotization of a dibenzothiophene compound (A-2) and decomposition of the resulting diazonium salt in the presence of an anion Y may be carried out through publicly known techniques, such as those described in Org. Synth. C.V. 1, 404, Org. Synth. C.V. 3, 130, or Chem. Ber. 1951, 84, 557.

A diazotizing reagent used in the above method may be, for example, nitric acid, nitrosylsulfuric acid, or sodium nitrite. The amount of the diazotizing reagent is not particularly limited, and usually about 1 to 100 times, preferably about 1 to 10 times the amount of the dibenzothiophene compound (A-2) in mole.

The diazotization of the dibenzothiophene compound (A-2) is usually carried out in an inert gas atmosphere, such as of argon or nitrogen.

The reaction may be proceeded either without or in a solvent. The solvent may be, for example, a halogenated hydrocarbon such as dichloromethane, chloroform, or 1,2-dichloroethane; an aliphatic hydrocarbon such as hexane, heptane, octane, or nonane; an aromatic hydrocarbon such as benzene, toluene, xylene, or chlorobenzene; an ether solvent such as diethyl ether or tetrahydrofuran; an organic acid such as acetic acid or methanesulfonic acid; a mineral acid such as nitric acid or sulfuric acid; water; or mixtures thereof.

The reaction temperature for the diazotization is not particularly limited, and is usually −50 to 100° C., preferably −30 to 50° C.

The diazotization results a diazonium salt, which is used in the following diazo decomposition process usually in the form of an as-obtained reaction mixture, due to its poor stability. The diazonium salt may, however, readily be separated from the reaction mixture, if necessary, through ordinary processes including distillation, recrystallization, column chromatography, or the like.

The generated diazonium salt is then decomposed in the presence of an anion Y, which may be donated by, for example, water, copper (I) chloride, copper (I) bromide, hydrogen chloride, or hydrogen bromide. The amount of the donor of the anion Y used in the reaction is not particularly limited, but is usually 1 to 100 times, preferably 1 to 10 times the amount of dibenzothiophene compound (A-2) in mole.

The decomposition of the diazonium salt in the presence of an anion Y may usually be carried out in an inert gas atmosphere, such as of argon or nitrogen. The reaction may be proceeded either without or in a solvent, which may preferably be selected from those mentioned above for use in diazotization of the dibenzothiophene compound (A-2).

The reaction temperature for the decomposition is not particularly limited, and is usually about −50 to 200° C., preferably about −30 to 150° C.

The dibenzothiophene compound (A-1) thus formed may readily be separated from the reaction mixture through ordinary processes, if necessary, including extraction with an organic solvent, washing with water, distillation, recrystallization, column chromatography, or the like.

In the formula (A-2) representing the dibenzothiophene compound (A-2) of the present invention used in manufacture of the dibenzothiophene compound (A-1), $A^1$ to $A^6$ and X mean the same as those in the formula (A-1). Specific examples of the dibenzothiophene compound (A-2) may include compounds having $A^1$ to $A^6$ and X corresponding to those in the dibenzothiophene compound (A-1).

The dibenzothiophene compound (A-2) may be prepared by reducing a dibenzothiophene oxide compound (A-3). In the reaction, the two functional groups, sulfoxide and nitro groups, are reduced either one by one or simultaneously.

The reduction of a dibenzothiophene oxide compound (A-3) may be carried out, for example, by a conventional technique such as disclosed in J. Am. Chem. Soc. 1952, 74, 1165.

For reducing the dibenzothiophene oxide compound (A-3), a reducing agent may be used, which may be, for example, tin (II) chloride or iron. The amount of the reducing agent is not particularly limited, and is usually about 1 to 100 times, preferably about 1 to 10 times the amount of the dibenzothiophene oxide compound (A-3) in mole.

The reduction of a dibenzothiophene oxide compound (A-3) may usually be carried out in an inert gas atmosphere, such as of argon or nitrogen. The reaction may be proceeded either without or in a solvent, which may preferably be selected from those mentioned above for use in diazotization of the dibenzothiophene compound (A-2).

The reaction temperature for the reduction is not particularly limited, and is usually about −50 to 200° C., preferably about −30 to 150° C.

The dibenzothiophene compound (A-2) resulting from the reduction may readily be separated from the reaction mixture, if necessary, through ordinary processes including extraction with an organic solvent, washing with water, distillation, recrystallization, column chromatography, or the like.

In the formula (A-3) representing the dibenzothiophene oxide compound (A-3) of the present invention used in manufacture of the dibenzothiophene compound (A-2), $A^1$ to $A^6$ and X mean the same as those in the formula (A-1). Specific examples of the dibenzothiophene oxide compound (A-3) may include compounds having $A^1$ to $A^6$ and X corresponding to those in the dibenzothiophene compound (A-1).

The dibenzothiophene oxide compound (A-3) of the present invention may be prepared by nitrating a dibenzothiophene oxide compound (A-4), which may be carried out, for example, by a conventional technique such as disclosed in J. Am. Chem. Soc. 1952, 74, 1165.

For nitrating the dibenzothiophene oxide compound (A-4), a nitrating agent may be used, which may be selected from, for example, nitrates or nitrites of sodium, potassium, or silver; alkyl nitrates such as butyl or amyl nitrate; or nitric acid.

The amount of the nitrating agent is not particularly limited, and is usually about 1 to 100 times, preferably about 1 to 10 times the amount of the dibenzothiophene oxide compound (A-4) in mole.

The nitration of a dibenzothiophene oxide compound (A-4) may usually be carried out in an inert gas atmosphere, such as of argon or nitrogen. The reaction may be proceeded either without or in a solvent, which may preferably be selected from those mentioned above for use in diazotization of the dibenzothiophene compound (A-2).

The reaction temperature for the nitration is not particularly limited, and is usually about −50 to 200° C., preferably −30 to 150° C.

The dibenzothiophene oxide compound (A-3) resulting from the nitration may readily be separated from the reaction mixture, if necessary, through ordinary processes including extraction with an organic solvent, washing with water, distillation, recrystallization, column chromatography, or the like.

In the formula (A-4) representing the dibenzothiophene oxide compound (A-4) of the present invention used in manufacture of the dibenzothiophene oxide compound (A-3), $A^1$ to $A^6$ and X mean the same as those in the formula (A-1). Specific examples of the dibenzothiophene oxide compound (A-4) may include compounds having $A^1$ to $A^6$ and X corresponding to those in the dibenzothiophene compound (A-1).

The dibenzothiophene oxide compound (A-4) of the present invention may be prepared by oxidizing a dibenzothiophene compound (A-5), which may be carried out, for example, by a conventional technique such as disclosed in J. Am. Chem. Soc. 1948, 70, 1748.

For oxidation of the dibenzothiophene compound (A-5), an oxidizing agent may be used, which may be selected from, for example, organic peroxides such as m-chloroperbenzoic acid; perhalides such as sodium periodate; a mixture of chlorine and water; or hydrogen peroxide.

The amount of the oxidizing agent is not particularly limited, and is usually about 1 to 100 times, preferably about 1 to 10 times the amount of the dibenzothiophene compound (A-5) in mole.

The oxidation of dibenzothiophene compound (A-5) may usually be carried out in an inert gas atmosphere, such as of argon or nitrogen. The reaction may be proceeded either without or in a solvent, which may preferably be selected from those mentioned above for use in diazotization of the dibenzothiophene compound (A-2).

The reaction temperature for the oxidation is not particularly limited, and is usually about −50 to 200° C., preferably −30 to 150° C.

The dibenzothiophene oxide compound (A-4) resulting from the oxidation may readily be separated from the reaction mixture, if necessary, through ordinary processes including extraction with an organic solvent, washing with water, distillation, recrystallization, column chromatography, or the like.

EXAMPLES

The present invention will now be explained in detail with reference to Examples, but the present invention is not limited thereto.

A series of reactions to be discussed in Examples 1-1 to 1-4 below may be expressed as follows:

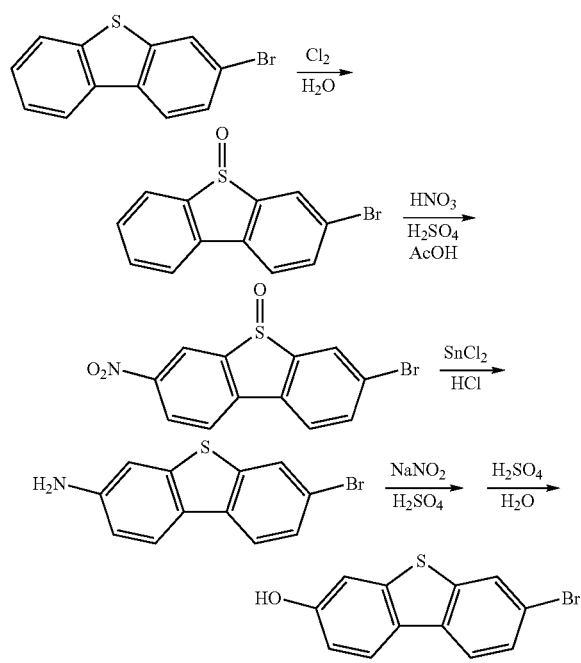

Example 1-1

According to the process disclosed in J. Am. Chem. Soc., 1951, 73, 5887, 3-bromodibenzothiophene was synthesized. A flask equipped with a stirrer and a thermometer was charged with 44.1 g of the thus synthesized 3-bromodibenzothiophene and 441 g of carbon tetrachloride in a nitrogen atmosphere, and cooled to −5° C. The mixture was bubbled with a chlorine gas under stirring at −7° C. to −12° C. for 5 hours. The reaction mass was poured into 1000 g of ice water, and stirred at or below 5° C. for 40 minutes. The reactant was filtered and washed with carbon tetrachloride. The resulting crystals were dried to obtain 27.91 g of 3-bromodibenzothiophene-5-oxide. The product was subjected to elemental analysis, the results of which are as follows:

Elemental Analysis: $C_{12}H_7BrOS$ (Theoretical(%): C=51.63; H=2.53; Observed(%): C=51.59; H=2.58).

Example 1-2

A flask equipped with a stirrer and a thermometer was charged with 69.8 g of glacial acetic acid and 27.9 g of 3-bromodibenzothiophene-5-oxide prepared in Example 1-1 in a nitrogen atmosphere, and cooled to 10° C. 239.8 g of concentrated sulfuric acid was added dropwise, and the resulting mixture was cooled to −2° C. Then 72.0 g of 70 wt % nitric acid was added dropwise at −2 to 8° C., and the resulting mixture was stirred at or below 5° C. for 2 hours. The reaction mass was poured into 1200 g of ice water to terminate the reaction, and stirred further. The reactant was filtered, washed with water, and dried. The resulting dry cake was washed with ethanol to obtain 31.9 g of 3-bromo-7-nitrodibenzothiophene-5-oxide. The product was subjected to elemental analysis, the results of which are as follows:

Elemental Analysis: $C_{12}H_6BrNO_3S$ (Theoretical (%): C=44.46; H=1.87; Observed(%): C=44.42; H=1.84).

Example 1-3

A flask equipped with a stirrer and a thermometer was charged with 26.98 g of the intermediate 3-bromo-7-nitrodibenzothiophene-5-oxide prepared in Example 1-2 and 269.8 g of glacial acetic acid in a nitrogen atmosphere. 112.7 g of $SnCl_2.2H_2O$ dissolved in 158 g of concentrated hydrochloric acid was added dropwise at 14 to 18° C. over 1 hour, and stirred overnight at room temperature. The resulting reactant was filtered, washed with 1:1 glacial acetic acid/ concentrated hydrochloric acid, and neutralized with 1100 g of a 7 wt % aqueous solution of sodium hydroxide. The reactant was extracted with ethyl acetate, washed with water, concentrated, and purified by silica gel chromatography using 1:1 hexane/chloroform mixed with 0.1 wt % triethylamine as an eluting solvent, to thereby obtain 17.31 g of objective 7-bromodibenzothiophene-3-yl-amine. The product was subjected to elemental analysis, the results of which are as follows:

Elemental Analysis: $C_{12}H_8BrNS$ (Theoretical(%): C=51.81; H=2.90; Observed(%): C=51.77; H=2.92).

Example 1-4

A flask equipped with a stirrer and a thermometer was charged with 209.3 g of concentrated sulfuric acid and 8.93 g of $NaNO_2$ in a nitrogen atmosphere, and cooled to 2° C. Then 24.0 g of the intermediate 7-bromodibenzothiophene-3-yl-amine prepared in Example 1-3 was added, and stirred at 2 to 4° C. for 3 hours. The resulting mixture together with 99.8 g of water was poured into 348.7 g of 65 wt % sulfuric acid preheated to 80° C., stirred at 80 to 85° C. for 5 hours, and cooled to room temperature. The reactant was filtered, extracted six times with 300 ml of ethyl acetate, and vacuum concentrated. The concentrate was purified by silica gel chromatography using chloroform as an eluting solvent to obtain 7.11 g of objective 7-bromodibenzothiophene-3-ol.

The $^1$H-NMR spectrum data and the results of elemental analysis of the product are shown below:

$^1$H-NMR(CDCl$_3$, δ): 4.98(s,1H),6.95–7.00(m,1H), 7.25–7.27 (m,1H),7.50–7.54(m,1H),7.84–7.88(m,1H), 7.91–7.93(m,1H), 7.93–7.97(m,1H) Elemental Analysis: C$_{12}$H$_7$BrOS (Theoretical(%): C=51.63; H=2.53; Observed (%): C=51.58, H=2.55).

Production Example 2-1

A flask equipped with a stirrer and a thermometer was charged with 27.64 g of a starting material RDBT-1 and 276.4 g of carbon tetrachloride in a nitrogen atmosphere, and cooled to 2° C. The mixture was bubbled with a chlorine gas under stirring for 5 hours. The reaction mass was poured into 400 g of ice water, and stirred for 50 minutes. The reactant was filtered and washed with water. The filtrate was concentrated, and repulped with 1:1 toluene/hexane, to thereby obtain 18.53 g of IMDBT-1.

A flask equipped with a stirrer and a thermometer was charged with 164.5 g of glacial acetic acid in a nitrogen atmosphere, and cooled to 5° C. Then 549.3 g of sulfuric acid was added dropwise, and heated to 23 to 25° C. 65.8 g of an intermediate IMDBT-1 was added and dissolved, and cooled to 5 to 9° C. 236.6 g of 70 wt % nitric acid was added dropwise, and stirred for 2 hours. The reaction mass was poured into 2745 g of ice water to terminate the reaction, and stirred further. The reactant was filtered, washed with water, and dried. The dry cake thus obtained was repulped with ethanol to obtain 69 g of IMDBT-2.

A flask equipped with a stirrer and a thermometer was charged with 69.0 g of the intermediate IMDBT-2 prepared above and 690.0 g of glacial acetic acid in a nitrogen atmosphere, to which 320.1 g of SnCl$_2$ dissolved in 439.5 g of concentrated hydrochloric acid was added dropwise at 24 to 33° C., and stirred overnight at room temperature. The reactant was filtered, washed with 1:1 glacial acetic acid/ concentrated hydrochloric acid, and neutralized with 600 g of a 10% aqueous solution of sodium hydroxide. The reactant was extracted with ethyl acetate, washed with water, concentrated, and purified by silica gel chromatography using chloroform as an eluting solvent, to thereby obtain 48.0 g of IMDBT-3.

A flask equipped with a stirrer and a thermometer was charged with 182.8 g of 98 wt % sulfuric acid and 18.28 g of NaNO$_2$ in a nitrogen atmosphere, and cooled to 2° C. Then 48.0 g of the intermediate IMDBT-3 prepared above dissolved in 576 g of glacial acetic acid was added dropwise, and stirred at 5 to 8° C. for 100 minutes. The mixture was cooled to –5° C., mixed with 500 ml of ether, and stirred at –5° C. for 25 minutes. The reactant was filtered and washed with ether. The resulting wet cake was introduced into a vessel charged at room temperature with 1037 g of a 48% aqueous solution of HBr and 51.84 g of CuBr, stirred at 25 to 64° C. for 30 minutes, refluxed at 64° C. for 2 hours, filtered, and washed with water. The resulting wet case was dried, and subjected to silica gel chromatography using hexane as an eluting solvent, to thereby obtain 41.8 g of IMDBT-4.

A flask equipped with a stirrer and a thermometer was charged with 10.53 g of the intermediate IMDBT-4 prepared above, 0.21 g of dichlorobis (triphenylphosphine)palladium, 0.21 g of triphenylphosphine, 0.11 g of copper iodide, and 40.5 g of triethylamine in a nitrogen atmosphere, and heated to 76° C. Then 5.05 g of 2-methyl-3-butyne-2-ol dissolved in 2.5 g of ethyl acetate was added dropwise, and stirred for 2 hours. The reactant was filtered, and washed with ethyl acetate. The filtrate was concentrated, and purified by silica gel chromatography using 5:1 hexane/ethyl acetate mixed with 0.1 wt % triethylamine as an eluting solvent, to thereby obtain 9.75 g of IMDBT-5.

A flask equipped with a stirrer and a thermometer was charged with 9.75 g of the intermediate IMDBT-5 prepared above, 48.8 g of toluene, and 0.4 g of KOH in a nitrogen atmosphere, heated to 95° C., and stirred for 3 hours. After the termination of the reaction, the reactant was concentrated, and purified by silica gel chromatography using hexane mixed with 0.1 wt % triethylamine as an eluting solvent, to thereby obtain 6.60 g of objective IMDBT-6. The $^1$H-NMR spectrum data of the resulting IMDBT-6, as well as the formulae of the series of reactions are shown below.

$^1$H-NMR(CDCl$_3$, δ): 3.15(s,1H),7.43–7.46(m,2H), 7.53–7.56 (m,1H),7.81–7.84(m,1H),7.97–8.11(m,3H)

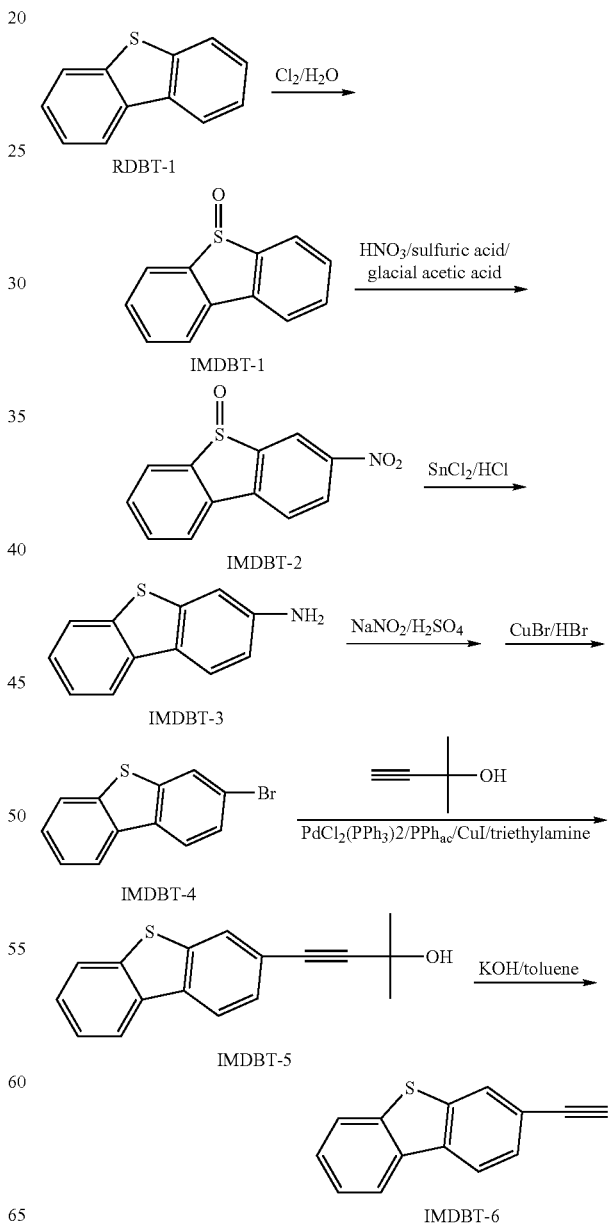

Production Example 2-2

A flask equipped with a stirrer and a thermometer was charged with 18.95 g of IMDBT-4 prepared in Production Example 2-1, 0.387 g of dichlorobis(triphenylphosphine) palladium, 0.38 g of triphenylphosphine, 0.19 g of copper (I) iodide, and 72.9 g of triethylamine in a nitrogen atmosphere, and heated to 76° C. Then 17.41 g of IM-2 dissolved in 9.1 g of ethyl acetate was added dropwise, stirred at 76 to 80° C. for 5 hours, and allowed to cool to room temperature. The reactant was filtered and washed with ethyl acetate, and the filtrate was concentrated. The resulting solid was mixed with 129.6 g of methanol, 0.32 g of p-toluenesulfonic acid, and 129.6 g of THF, and stirred at 23 to 40° C. for 2.5 hours. After the termination of the reaction, the reaction mixture was neutralized with 2 g of triethylamine, and concentrated. The concentrate was purified by silica gel chromatography using 10:1 hexane/ethyl acetate mixed with 0.1 wt % triethylamine as an eluting solvent, to thereby obtain 14.1 g of intermediate IMDBT-7.

A flask equipped with a stirrer and a thermometer was charged with the thus obtained 14.1 g of the intermediate IMDBT-7 in a nitrogen atmosphere. 70.5 g of toluene, 28.1 g of pyridine, and 0.28 g of 4-pyrrolidinopyridine were added, and cooled to −2° C. While stirring the mixture at the same temperature, 18.17 g of trifluoromethanesulfonic acid anhydride was added dropwise, and stirred at 0 to 2° C. for 1.5 hours. After the termination of the reaction, the mixture was mixed with water, and extracted with ethyl acetate. The resulting organic phase was concentrated, and subjected to silica gel chromatography using 20:1 hexane/chloroform as an eluting solvent, to thereby obtain 18.64 g of intermediate IMDBT-8.

The $^1$H-NMR spectrum data of the resulting IMDBT-8, as well as the formulae of the series of reactions above are shown below.

$^1$H-NMR(CDCl$_3$, δ): 1.29(t,3H,J=7.5 Hz),2.75 (q,2H, J=7.5 Hz), 7.20–7.26 (m,1H),7.40–7.60 (m,5H),7.81–7.89 (m,1H), 8.01–8.18 (m,3H)

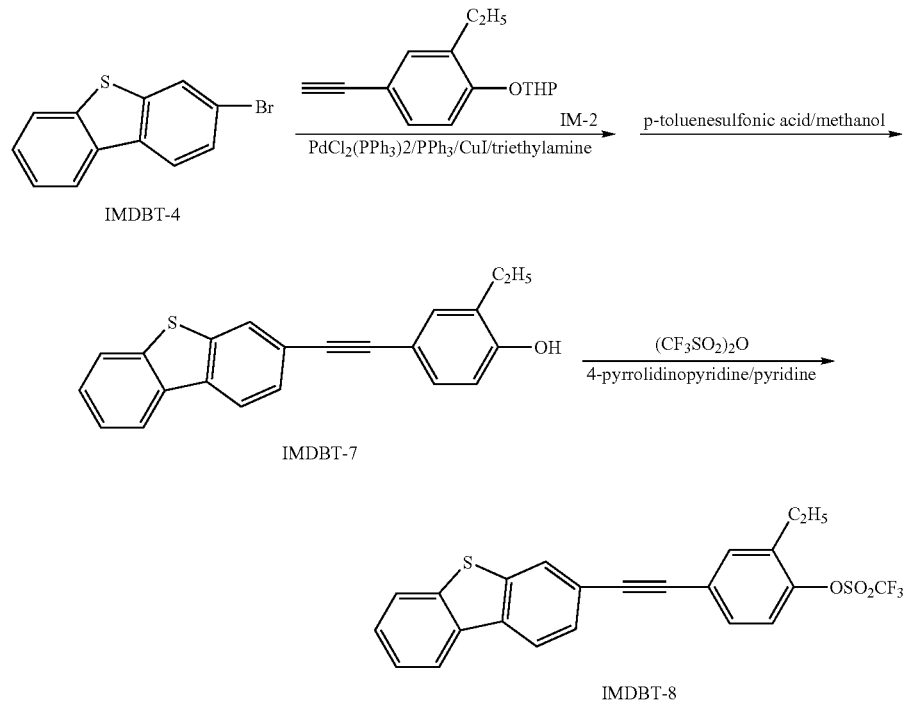

Example 2-1

A flask equipped with a stirrer and a thermometer was charged with 5.53 g of IMDBT-8 prepared in Production Example 2-2, 0.11 g of dichlorobis(triphenylphosphine) palladium, 3.64 g of triethylamine, and 33.2 g of DMF in a nitrogen atmosphere, and heated to 65° C. Then 4.50 g of IMDBT-6 prepared in Production Example 2-1 dissolved in 6.8 g of DMF was added dropwise, stirred at 63 to 68° C. for 7 hours, and allowed to cool to room temperature. The reactant was filtered and washed with ethyl acetate. The wet cake 1 obtained on the filter was preserved. Next, the filtrate was washed with water and concentrated. The resulting solid was subjected to silica gel chromatography using chloroform mixed with 0.1 wt % triethylamine as an eluting solvent, repulped with ethyl acetate, mixed with the wet cake 1 preserved on the filter, subjected to silica gel chromatography using 5:1 hexane/chloroform mixed with 0.1 wt % triethylamine as an eluting solvent, and recrystallized from chloroform, to thereby obtain 2.86 g of objective DBT1116.

The $^1$H-NMR spectrum data of the obtained compound DBT1116, as well as the formulae of the reaction in this Example are shown below.

$^1$H-NMR(CDCl$_3$, δ): 1.38(t,3H,J=7.5 Hz),2.95(q,2H), 7.37–7.58(m,7H),7.58–7.69(m,2H),7.83–7.90(m,2H), 8.02–8.08 (m,2H),8.11–8.20(m,4H)

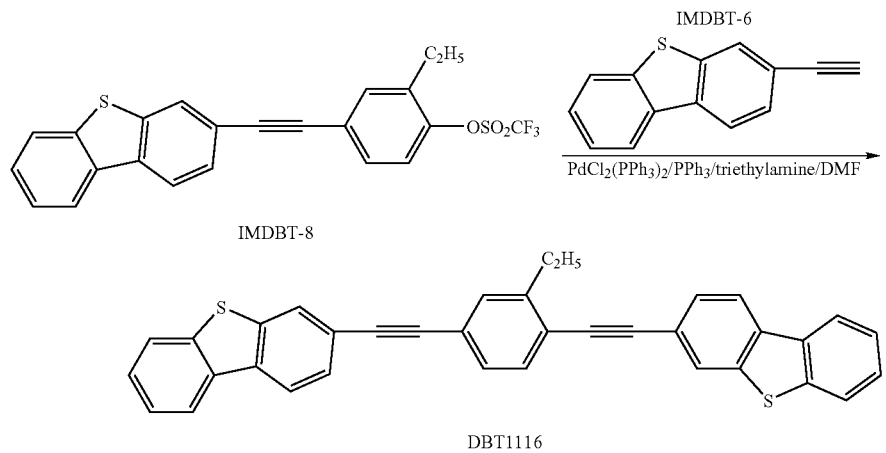

The obtained DBT1116 was theoretically divided into the following parts, and the difference ΔE in energy of HOMO of the parts and the polarizability anisotropy Δα were calculated by the method of molecular orbitals. The results are as follows:

$\Delta E = E_{DBT1116\text{-}1} - E_{DBT1116\text{-}2} = 0.77$ (eV)

Δα=753 (atomic units)

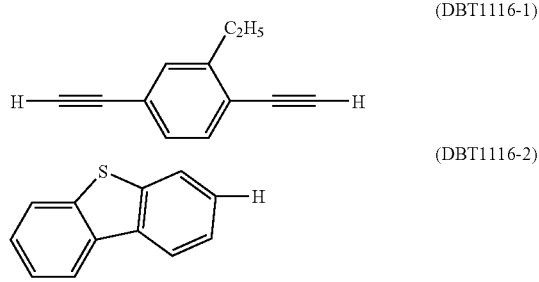

The phase sequence of the compound DBT1116 was evaluated with polarization microscope to find that the compound was in the crystalline phase below 227° C., and in the nematic phase from 227° C. When the compound was further heated to 300° C., it was still in the nematic phase. It was thus demonstrated that this compound was a liquid crystalline compound. Upon visual observation in its nematic and liquid phases, this compound was transparent and colorless.

5 wt % of the compound DBT1116 was added to a nematic composition MJ931381 (manufactured by Merck Japan Co.), and the refractive index anisotropy Δn was determined, from which Δn of the compound was extrapolated based on the concentration. It was determined that the Δn of the compound was 0.63, which is an extremely large value. Δn was measured with an Abbe refractometer at 20° C. and at the wavelength of 589 nm.

Example 2-2

A flask equipped with a stirrer and a thermometer was charged with 5.53 g of IMDBT-8 prepared in Production Example 2-2, 0.17 g of dichlorobis(triphenylphosphine) palladium, 3.64 g of triethylamine, and 33.2 g of DMF in a nitrogen atmosphere, and heated to 65° C. Then 3.84 g of IM-1 dissolved in 4.3 g of DMF were added dropwise, stirred at 64 to 68° C. for 10 hours, and allowed to cool to room temperature. The reactant was filtered and washed with ethyl acetate. The residue left on the filter was concentrated, and the resulting solid was subjected to silica gel chromatography using chloroform mixed with 0.1 wt % triethylamine as an eluting solvent, repulped with ethyl acetate, and purified by silica gel chromatography using 10:1 hexane/chloroform mixed with 0.1 wt % triethylamine as an eluting solvent, to thereby obtain 4.18 g of objective DBT1115. The $^1$H-NMR spectrum data of the obtained compound DBT1115, as well as the formulae of the reaction above are shown below.

$^1$H-NMR(CDCl$_3$, δ): 0.94(t,3H,J=7.5 Hz),1.33(t,3H, J=7.5 Hz), 1.38–1.49(m,4H),1.75–1.85(m,2H),2.90(q,2H, J=7.5 Hz), 3.97(t,2H, J=7.5 Hz),6.86–6.90(m,2H),7.37–7.63 (m,8H), 7.85–8.37(m,4H)

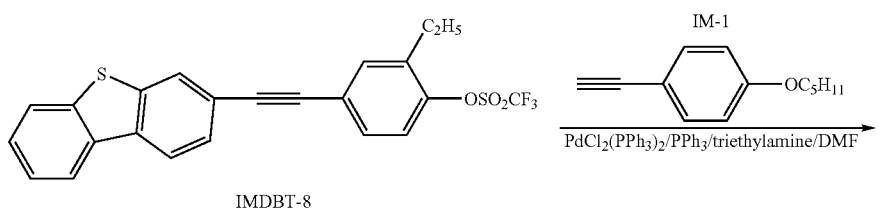

-continued

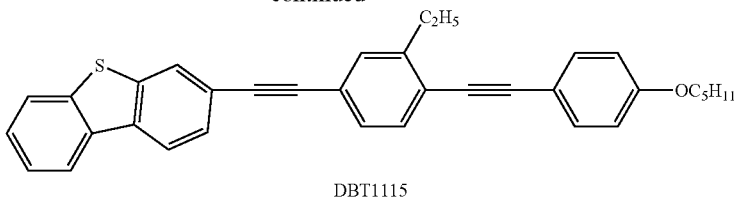

DBT1115

The obtained DBT1115 was theoretically divided into the following parts, and the difference ΔE in energy of HOMO of the parts and the polarizability anisotropy Δα were calculated by the method of molecular orbitals. The results are as follows:

$\Delta E = E_{DBT1115-1} - (E_{DBT1115-2} + E_{DBT1115-3})/2 = 0.39$ (eV)

Δα=652 (atomic units)

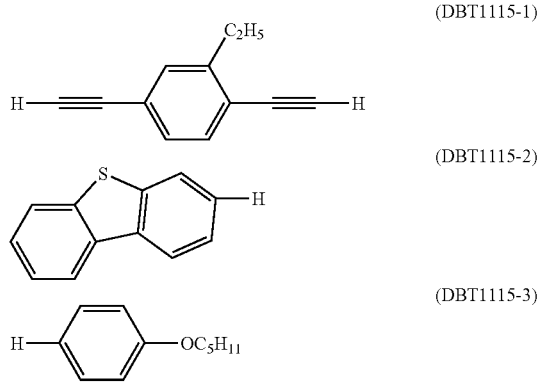

(DBT1115-1)

(DBT1115-2)

(DBT1115-3)

The phase sequence of the compound DBT1115 was evaluated with polarization microscope to find that the compound was in the crystalline phase below 134° C., in the nematic phase in the range of 134 to 253° C., and in the isotropic phase above 253° C. It was thus demonstrated that this compound was a liquid crystalline compound. Upon visual observation in its nematic and liquid phases, this compound was transparent and colorless.

10 wt % of the compound DBT1115 was added to a nematic composition MJ931381 (manufactured by Merck Japan Co.), and the refractive index anisotropy Δn was determined, from which Δn of the compound was extrapolated based on the concentration. It was determined that the Δn of the compound was 0.53, which is an extremely large value. Δn was measured with an Abbe refractometer at 20° C. and at the wavelength of 589 nm.

Production Example 2-3

A flask equipped with a stirrer and a thermometer was charged with 44.1 g of a starting material IMDBT-4 prepared in Production Example 2-1 and 441 g of carbon tetrachloride in a nitrogen atmosphere, and cooled to −5° C. The mixture was bubbled with a chlorine gas under stirring at −7° C. to −12° C. for 5 hours. The reaction mass was poured into 1000 g of ice water, and stirred at or below 5° C. for 40 minutes. The reactant was filtered and washed with carbon tetrachloride. The resulting crystals were dried to obtain 27.91 g of IMDBT-9.

A flask equipped with a stirrer and a thermometer was charged with 69.8 g of glacial acetic acid and 27.9 g of IMDBT-9 prepared above in a nitrogen atmosphere, and cooled to 10° C. Then 239.8 g of concentrated sulfuric acid was added dropwise, and cooled to −2° C. 72.0 g of 70 wt % nitric acid was added dropwise at −2 to 8° C., and stirred at or below 5° C. for 2 hours. The resulting mixture was poured into 1200 g of ice water to terminate the reaction, and stirred further. The reactant was filtered, washed with water, and dried. The dry cake thus obtained was washed with ethanol to obtain 31.9 g of IMDBT-10.

A flask equipped with a stirrer and a thermometer was charged with 26.98 g of the intermediate IMDBT-10 prepared above and 269.8 g of glacial acetic acid in a nitrogen atmosphere. 112.7 g of $SnCl_2 \cdot 2 H_2O$ dissolved in 158 g of concentrated hydrochloric acid was added dropwise at 14 to 18° C. over 1 hour, and stirred overnight at room temperature. The reactant was filtered, washed with 1:1 glacial acetic acid/concentrated hydrochloric acid, and neutralized with 1100 g of a 7 wt % aqueous solution of sodium hydroxide. The reactant was extracted with ethyl acetate, washed with water, concentrated, and purified by silica gel chromatography using 1:1 hexane/chloroform mixed with 0.1 wt % triethylamine as an eluting solvent, to thereby obtain 17.31 g of IMDBT-11.

A flask equipped with a stirrer and a thermometer was charged with 209.3 g of concentrated sulfuric acid and 8.93 g of $NaNO_2$ in a nitrogen atmosphere, and cooled to 2° C. Then 24.0 g of the intermediate IMDBT-11 prepared above was added, and stirred at 2 to 4° C. for 3 hours. The resulting mixture together with 99.8 g of water was poured into 348.7 g of 65 wt % sulfuric acid preheated to 80° C., stirred at 80 to 85° C. for 5 hours, and cooled to room temperature. The reactant was filtered, extracted six times with 300 ml of ethyl acetate, and vacuum concentrated. The concentrate was purified by silica gel chromatography using chloroform as an eluting solvent to obtain 7.11 g of IMDBT-12. The $^1$H-NMR spectrum data of the resulting IMDBT-12 are shown below.

$^1$H-NMR(CDCl$_3$, δ): 4.98(s,1H),6.95–7.00(m,1H), 7.25–7.27(m,1H), 7.50–7.54(m,1H),7.84–7.88(m,1H), 7.91–7.93(m,1H), 7.93–7.97(m,1H)

A flask equipped with a stirrer and a thermometer was charged with 3.16 g of the intermediate IMDBT-12 prepared above, 3.91 g of potassium carbonate, 5.60 g of 1-iodopentane, and 16.8 g of methylethylketone in a nitrogen atmosphere, and heated to 80 to 85° C. The mixture was stirred at the same temperature for 4 hours, and cooled to room temperature. Inorganic salt was filtered out, and the filtrate was washed with 100 ml of ethyl acetate. The filtrate and the used washing liquid were vacuum concentrated. The concentrate was purified by silica gel chromatography using hexane as an eluting solvent to obtain 3.31 g of IMDBT-13. The $^1$H-NMR spectrum data of the resulting IMDBT-13 are shown below.

$^1$H-NMR(CDCl$_3$, δ): 0.95(t,3H,J=6 Hz),1.39–1.51(m, 4H), 1.84(tt,2H,J=6 Hz,6 Hz),4.05(t,2H,J=6 Hz),7.03–7.06 (m,1H), 7.26–7.29(m,2H),7.50–7.53(m,1H),7.85–7.98(m, 3H)

A flask equipped with a stirrer and a thermometer was charged with 3.30 g of IMDBT-13 prepared above, 0.03 g of dichlorobis(triphenylphosphine)palladium, 0.06 g of triphenylphosphine, 0.03 g of copper iodide, and 18.9 ml of triethylamine in a nitrogen atmosphere, and heated to 60° C. 3.30 g of IM-2 dissolved in 2 g of triethylamine was added dropwise at 60 to 65° C. over 1 hour, stirred at 70° C. for 7 hours, and cooled to room temperature. The inorganic salts were filtered out, and the filtrate was washed with 100 ml of ethylacetate and vacuum concentrated. The concentrate was mixed with 20 ml of methanol and 0.10 g of p-toluene-sulfonic acid, stirred at room temperature for 4 hours, and neutralized with 1.3 ml of triethylamine to terminate the reaction. The reaction liquid was concentrated, and the concentrate was purified by silica gel chromatography using 10:1 hexane/ethyl acetate mixed with 0.1 wt % triethylamine as an eluting solvent, to thereby obtain 4.30 g of IMDBT-14.

A flask equipped with a stirrer and a thermometer was charged with 3.92 g of the intermediate IMDBT-14 prepared above, 0.4 g of 4-pyrrolidinopyridine, 15.1 ml of pyridine, and 37.8 ml of dichloromethane in a nitrogen atmosphere, and ice cooled. Then 3.5 g of trifluoromethanesulfonic acid anhydride dissolved in 10 ml of dichloromethane was added dropwise at 1 to 3° C. over 1 hour, and stirred at the same temperature for 4 hours. After the termination of the reaction, 200 ml of ethyl acetate and 50 ml of water were added for extraction, and the resulting organic phase was separated, washed with water, and vacuum concentrated. The concentrate was purified by silica gel chromatography using 10:1 hexane/ethyl acetate mixed with 0.1 wt % triethylamine as an eluting solvent to obtain 4.10 g of IMDBT-15. The $^1$H-NMR spectrum data of the resulting IMDBT-15 as well as the reaction formulae of the series of reactions above are shown below.

$^1$H-NMR(CDCl$_3$, δ): 0.95(t,3H,J=6 Hz),1.30(t,3H,J=6 Hz), 1.40–1.54(m,4H),1.85(tt,2H,J=6 Hz,6 Hz),2.76(q,2H, J=6 Hz), 4.06(t,2H,J=6 Hz),7.05–7.08(m,1H),7.23–7.32(m, 2H),7.43–7.58(m,3H),7.97–8.02(m,3H)

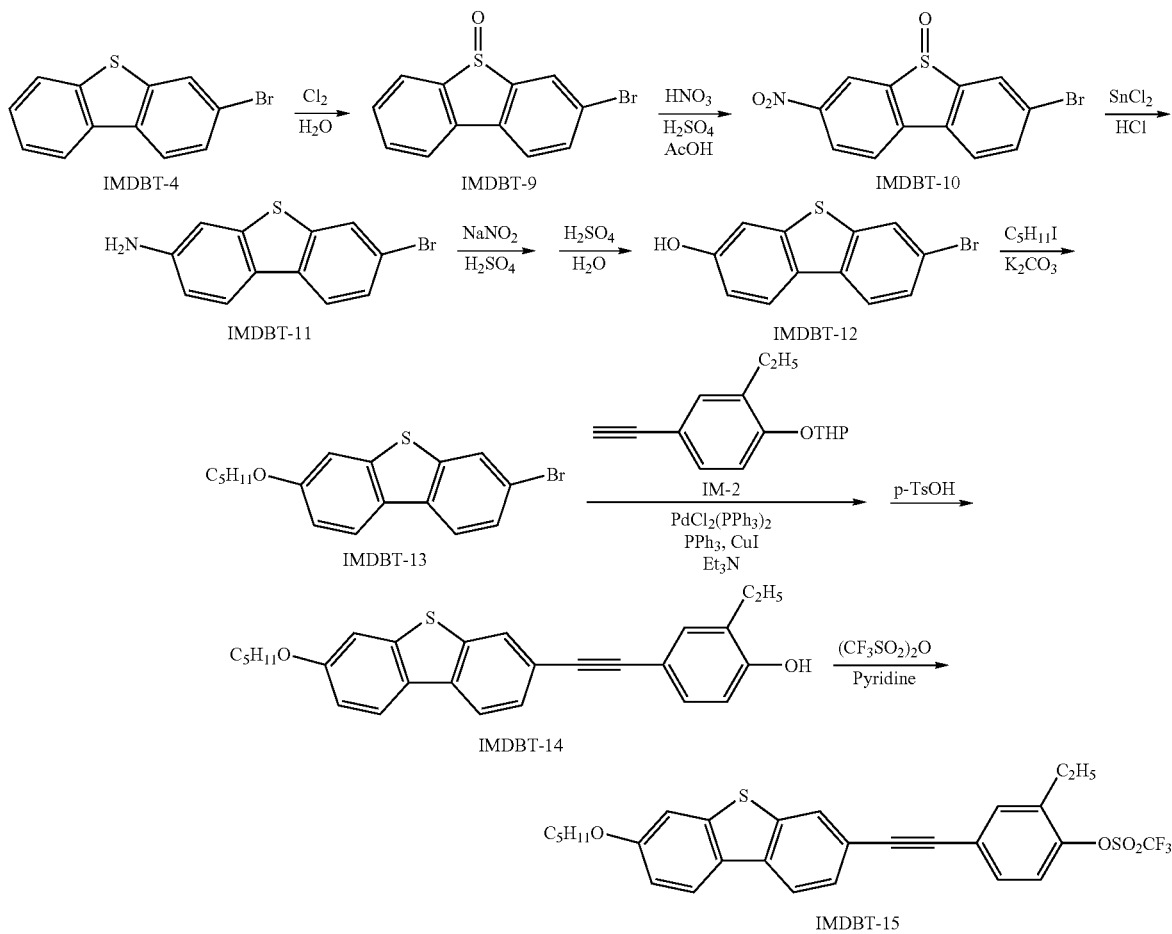

Production Example 2-4

A flask equipped with a stirrer and a thermometer was charged with 5.2 g of the intermediate IMDBT-12 prepared in Production Example 2-3, 0.007 g of p-toluenesulfonic acid, and 150 ml of chloroform in a nitrogen atmosphere, and ice cooled. Then 4.8 g of dihydropyran was added dropwise at 1° C., stirred at the same temperature for 6 hours, and neutralized with 3 ml of triethylamine to terminate the reaction. The reaction liquid was concentrated, and the concentrate was purified by silica gel chromatography using 13:1 hexane/ethyl acetate mixed with 0.1 wt % triethylamine as an eluting solvent, to thereby obtain 6.42 g of IMDBT-16.

A flask equipped with a stirrer and a thermometer was charged with 3.5 ml of 1-hexyne and 5 ml of tetrahydrofuran in a nitrogen atmosphere, and further 36 ml of 1M catecholborane/tetrahydrofuran solution was added. The mixture was heated to 68° C., and stirred at the same temperature for 8 hours. After the termination of the reaction, the reaction mass was concentrated in a nitrogen atmosphere, and passed to the next step as it was without isolating IMDBT-17 generated therein.

A flask equipped with a stirrer and a thermometer was charged with the concentrate containing IMDBT-17, 5.0 g of the intermediate IMDBT-16, 1.6 g of tetrakis(triphenylphosphine)palladium, 26 ml of toluene, and 40 ml of ethanol in a nitrogen atmosphere, and 11 ml of 2M sodium carbonate aqueous solution was added dropwise at room temperature over 20 minutes. The mixture was heated to 73° C., refluxed at the same temperature for 4 hours, stirred, cooled to room temperature, and mixed with ethyl acetate and water for extraction. The resulting organic phase was washed four times with water, vacuum concentrated, and the concentrate was passed to the next step as it was without isolating IMDBT-18 generated therein.

A flask equipped with a stirrer and a thermometer was charged with the concentrate containing IMDBT-18, 41 ml of methanol, and 0.5 g of p-toluenesulfonic acid in a nitrogen atmosphere, and stirred at room temperature for 3 hours. Then the reaction mixture was neutralized with 2 ml of triethylamine to terminate the reaction, concentrated, and purified by silica gel chromatography using 8:1 hexane/ethyl acetate mixed with 0.1 wt % triethylamine as an eluting solvent, to thereby obtain 3.5 g of IMDBT-19.

A flask equipped with a stirrer and a thermometer was charged with 3.8 g of the intermediate IMDBT-19, 0.6 g of 4-pyrrolidinopyridine, 22 ml of pyridine, and 54 ml of dichloromethane in a nitrogen atmosphere, and ice cooled. Then 2.6 ml of trifluoromethanesulfonic acid anhydride dissolved in 8 ml of dichloromethane was added dropwise at 1 to 3° C. over 1 hour, and stirred at the same temperature for 4 hours. After the termination of the reaction, 80 ml of dichloromethane and 50 ml of water were added for extraction, and the resulting organic phase was separated, washed with water, and vacuum concentrated. The concentrate was purified by silica gel chromatography using 5:1 hexane/ethyl acetate mixed with 0.1 wt % triethylamine as an eluting solvent, to obtain 4.4 g of IMDBT-20. The $^1$H-NMR spectrum data of the resulting IMDBT-20 are shown below.

$^1$H-NMR(CDCl$_3$, δ): 0.95(t,3H,J=6 Hz),1.36–1.52(m,4H, J=6 Hz), 2.29(dt,2H,Jd=6 Hz,Jt=6 Hz),6.35(dt,1H,Jd=15 Hz,Jt=6 Hz), 6.50(d,1H,J=15 Hz),7.31–7.35(m,1H), 7.47–7.50(m,1H),7.72–7.78(m,2H), 8.00–8.11(m,2H)

A flask equipped with a stirrer and a thermometer was charged with 3.0 g of the intermediate IMDBT-20, 0.2 g of dichlorobis(triphenylphosphine)palladium, 1.5 ml of triethylamine, and 29 ml of dimethylformamide in a nitrogen atmosphere, and heated to 45° C. Then 2 ml of trimethylsilylacetylene was added dropwise, and stirred at the same temperature for 4 hours. The mixture was cooled to room temperature, and mixed with 50 ml of diethyl ether and 20 ml of water for extraction. The resulting organic phase was separated, washed with water, and vacuum concentrated. The concentrate was subjected to silica gel chromatography using 20:1 hexane/ethyl acetate mixed with 0.1 wt % triethylamine as an eluting solvent, to obtain 2.60 g of IMDBT-21.

A flask equipped with a stirrer and a thermometer was charged with 2.60 g of the intermediate IMDBT-21, 0.3 g of potassium carbonate, 70 ml of methanol, and 35 ml of tetrahydrofuran in a nitrogen atmosphere, and stirred at room temperature for 2 hours. Then ethyl acetate was added, the inorganic substances were filtered out, and the filtrate was washed with ethyl acetate. The filtrate and the used washing liquid were vacuum concentrated, and purified by silica gel chromatography using 20:1 hexane/ethyl acetate mixed with 0.1 wt % triethylamine as an eluting solvent to obtain 1.57 g of the objective IMDBT-22. The $^1$H-NMR spectrum data of the resulting IMDBT-22, as well as the reaction formulae of the series of reactions above are shown below.

$^1$H-NMR(CDCl$_3$, δ): 0.94(t,3H,J=6 Hz),1.35–1.53(m, 4H), 2.26(dt,2H,Jd=6 Hz,Jt=6 Hz),3.17(s,1H),6.34(dt,1H, Jd=15 Hz, Jt=6 Hz),6.49(d,1H,J=15 Hz),7.43–7.46(m,1H), 7.51–7.55 (m,1H),7.76–7.77(m,1H),7.94–8.11(m,3H)

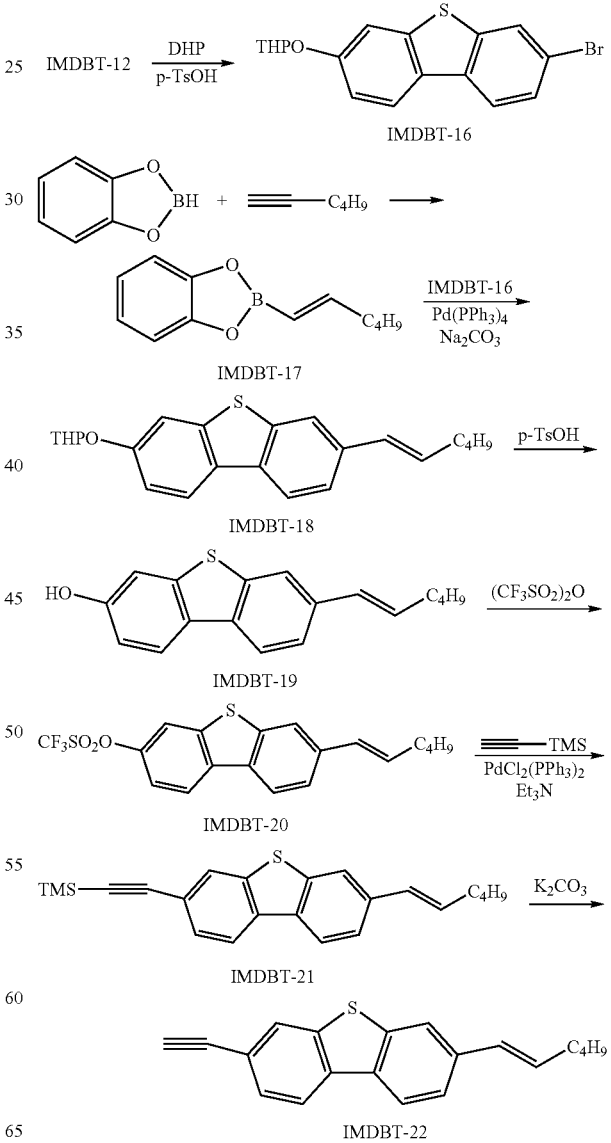

Example 2-3

A flask equipped with a stirrer and a thermometer was charged with 1.90 g of IMDBT-15 prepared in Production Example 2-3, 0.07 g of dichlorobis(triphenylphosphine) palladium, 0.7 ml of triethylamine, and 14 ml of dimethylformamide in a nitrogen atmosphere, and heated to 60° C. Then 1.60 g of IMDBT-22 prepared in Production Example 2-4 dissolved in 4 ml of dimethylformamide was added dropwise at the same temperature over 8 hours, and stirred at 60° C. for 2 hours. After the termination of the reaction, 20 ml of diethyl ether and 10 ml of water were added for extraction, and the resulting organic phase was washed twice with 10 ml of water, and concentrated. The concentrate was purified by silica gel chromatography using 10:1 hexane/chloroform mixed with 0.1 wt % triethylamine as an eluting solvent, to obtain 120 mg of the objective compound DBT1125. The $^1$H-NMR spectrum data of the resulting DBT1125, as well as the reaction formulae of the reaction above are shown below.

$^1$H-NMR(CDCl$_3$, δ): 0.95(t,3H,J=6 Hz),0.96(t,3H,J=6 Hz), 1.34–1.48(m,11H),1.85(tt,2H,J=6 Hz,6 Hz),2.26(dt, 2H,Jd=6 Hz,Jt=6 Hz),2.93(q,2H,J=6 Hz),4.06(t,2H,J=6 Hz), 6.34(dt,1H,Jd=15 Hz,Jt=6 Hz),6.51(d,1H,J=15 Hz), 7.05–7.09(m,1H),7.31–7.61 (m,7H),7.79–7.80(m,1H), 7.98–8.09(m,6H)

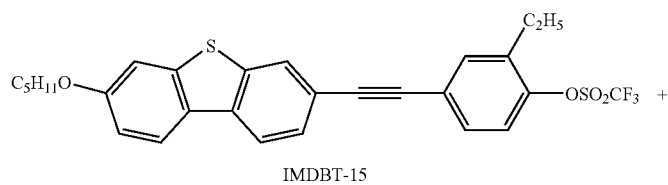

IMDBT-15

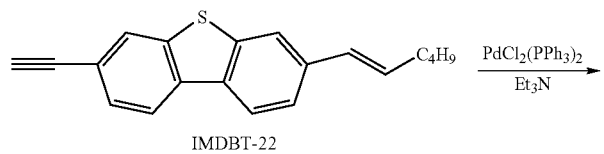

IMDBT-22

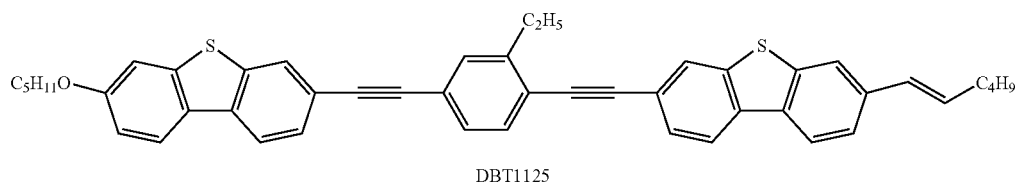

DBT1125

The phase sequence of the compound DBT1125 was evaluated in the same manner as in Example 2-1, to find that the compound was in the crystalline phase below 226° C., and in the liquid crystalline phase from 226° C. When the compound was further heated to 300° C., no phase transition was observed. It was thus demonstrated that this compound was a liquid crystalline compound.

5 wt % of the compound DBT1125 was added to a nematic composition MJ931381 (manufactured by Merck Japan Co.) and the refractive index anisotropy Δn was determined, from which Δn of the compound was extrapolated based on the concentration. It was determined that the Δn of the compound was 0.63, which is an extremely large value. An was measured with an Abbe refractometer at 20° C. and at the wavelength of 589 nm.

The obtained DBT1125 was theoretically divided into the following parts, and the difference ΔE in energy of HOMO of the parts and the polarizability anisotropy Δα were calculated by the method of molecular orbitals. The results are as follows:

$$\Delta E = E_{DBT1125\text{-}1} - (E_{DBT1125\text{-}2} + E_{DBT1125\text{-}3})/2 = 0.78 \text{ (eV)}$$

$$\Delta\alpha = 950 \text{ (atomic units)}$$

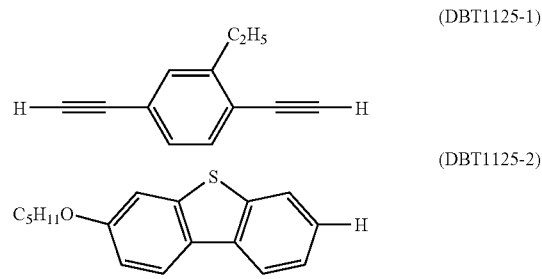

(DBT1125-1)

(DBT1125-2)

-continued

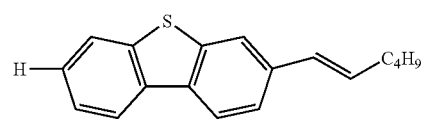

(DBT1125-3)

Example 2-4

Liquid crystal composition M-1 was prepared by mixing 6.9 wt % of DBT1115 prepared in Example 2-1, 2.6 wt % of DBT1116 prepared in Example 2-2, 30 wt %, 21.4 wt %, and 7.1 wt % of the compounds represented by the formulae (5-1), (5-2), and (5-3), respectively, as compounds represented by the formula (5), 8.2 wt % and 5.8 wt % of the compounds represented by the formulae (6-1) and (6-2), respectively, as compounds represented by the formula (6), and 13.7 wt % and 4.3 wt % of the compounds represented by the formulae (7-1) and (7-2), respectively, as a compound represented by the formula (7).

The phase sequence of the composition M-1 was evaluated in the same manner as in Example 2-1 to find that the composition was in the nematic phase in the temperature range of 7 to 195° C. The refractive index anisotropy of the composition M-1 was measured, using a glass cell with the tip angle of 1.6 degree pretreated for parallel alignment and filled with M-1, in accordance with the Hollow Prism Method described in *Handbook of Liquid Crystals*, Vol. 2A, p129 (ed. by D. Demus et al., Wiley-VCH Verlag GmbH), using helium-neon laser as a light source. It was found that the refractive index anisotropy of the composition M-1 was 0.43 (20° C., 632.8 nm), which is an extremely large value.

Example 2-5

Liquid crystal composition M-2 was prepared by mixing 2.2 wt % of DBT1115 prepared in Example 2-1, 5.9 wt % of DBT1116 prepared in Example 2-2, 20.2 wt %, 6.5 wt %, 21.9 wt %, and 13.5 wt % of the compounds represented by the formulae (5-1), (5-3), (5-4), and (5-5), respectively, as compounds represented by the formula (5), 8.3 wt % and 6.0 wt % of the compounds represented by the formulae (6-1) and (6-2), respectively, as compounds represented by the formula (6), and 12.0 wt % and 3.6 wt % of the compounds represented by the formulae (7-1) and (7-2), respectively, as compounds represented by the formula (7).

The phase sequence of the composition M-2 was evaluated to find that the composition was in the nematic phase at room temperature, and underwent transition from a nematic to isotropic phase at 175° C. The refractive index anisotropy of the composition M-2 was measured in the same manner as in Example 2-4, to find that the refractive index anisotropy of M-2 was 0.46 at 632.8 nm and 0.51 at 543.5 nm, which are extremely large values.

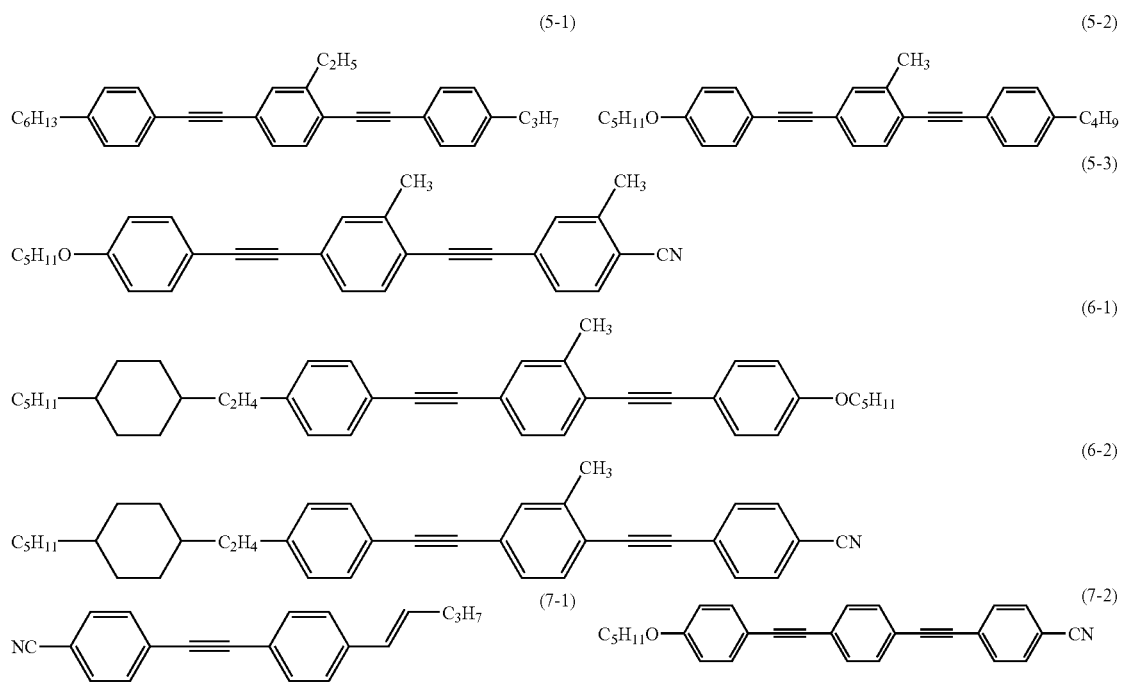

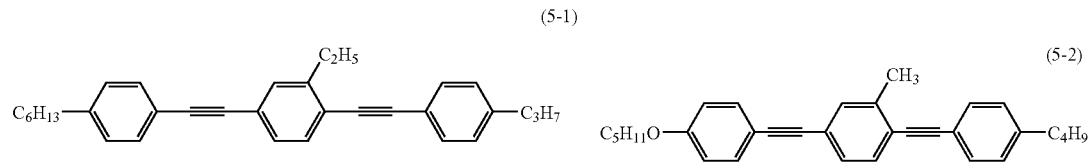

-continued

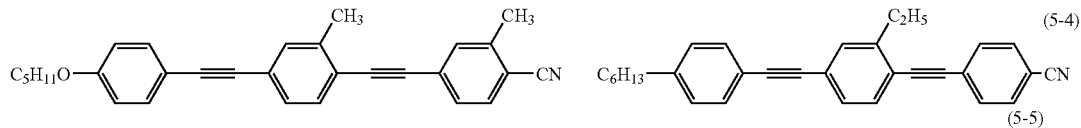

(5-3)
(5-4)
(5-5)

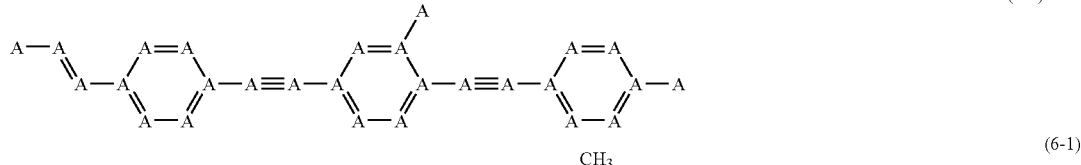

(6-1)
(6-2)

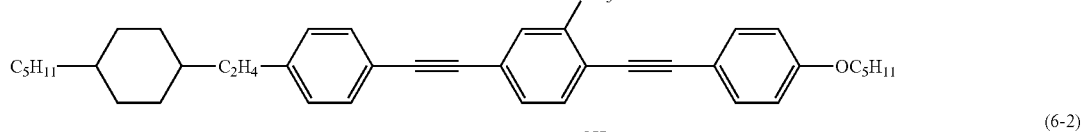

(7-1)
(7-2)

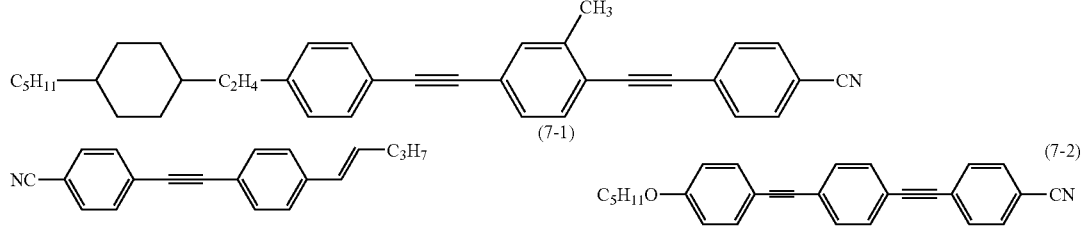

Production Example 3-1

A flask equipped with a stirrer and a thermometer was charged with 44.1 g of a starting material IMDBT-4 and 441 g of carbon tetrachloride in a nitrogen atmosphere, and cooled to −5° C. The mixture was then bubbled with a chlorine gas under stirring at −7° C. to −12° C. for 5 hours. The reaction mass was poured into 1000 g of ice water, and stirred at or below 5° C. for 40 minutes. The reactant was separated by filtration, washed with carbon tetrachloride, and the resulting crystals were dried to obtain 27.91 g of IMDBT-9.

A flask equipped with a stirrer and a thermometer was charged with 69.8 g of glacial acetic acid and 27.9 g of IMDBT-9 prepared above in a nitrogen atmosphere, and cooled to 10° C. Then 239.8 g of concentrated sulfuric acid was added dropwise, and cooled to −2° C. 72.0 g of 70 wt % nitric acid was then added dropwise at −2 to 8° C., and stirred at or below 5° C. for 2 hours. The reaction mass was poured into 1200 g of ice water to terminate the reaction, and stirred further. The reactant was separated by filtration, washed with water, and dried. The resulting dry cake was washed with ethanol to obtain 31.9 g of IMDBT-10.

A flask equipped with a stirrer and a thermometer was charged with 26.98 g of IMDBT-10 and 269.8 g of glacial acetic acid in a nitrogen atmosphere. 112.7 g of $SnCl_2·2 H_2O$ dissolved in 158 g of concentrated hydrochloric acid was added dropwise at 14 to 18° C. over 1 hour, and stirred overnight at room temperature. The reactant was filtered, washed with 1:1 glacial acetic acid/concentrated hydrochloric acid, and neutralized with 1100 g of a 7 wt % aqueous solution of sodium hydroxide. The reactant was extracted with ethyl acetate, washed with water, concentrated, and purified by silica gel chromatography using 1:1 hexane/chloroform mixed with 0.1 wt % triethylamine as an eluting solvent, to thereby obtain 17.31 g of IMDBT-11.

A flask equipped with a stirrer and a thermometer was charged with 209.3 g of concentrated sulfuric acid and 8.93 g of $NaNO_2$ in a nitrogen atmosphere, and cooled to 2° C. Then 24.0 g of IMDBT-11 prepared above was added, and stirred at 2 to 4° C. for 3 hours. The resulting mixture together with 99.8 g of water was poured into 348.7 g of 65 wt % sulfuric acid preheated to 80° C., stirred at 80 to 85° C. for 5 hours, and cooled to room temperature. The reactant was filtered, extracted six times with 300 ml of ethyl acetate, and vacuum concentrated. The concentrate was purified by silica gel chromatography using chloroform as an eluting solvent to obtain 7.11 g of IMDBT-12. The $^1$H-NMR spectrum data of the resulting IMDBT-12 are shown below.

$^1$H-NMR (CDCl$_3$, δ): 4.98(s,1H),6.95–7.00(m,1H), 7.25–7.27 (m,1H),7.50–7.54(m,1H),7.84–7.88(m,1H), 7.91–7.93 (m,1H),7.93–7.97(m,1H)

A flask equipped with a stirrer and a thermometer was charged with 1.34 g of IMDBT-12, 1.66 g of potassium carbonate, 2.51 g of 8-bromo-octanol, and 13.4 g of methylethylketone in a nitrogen atmosphere, heated to 80 to 85°αC., stirred at the same temperature for 5 hours, and cooled to room temperature. The solvent was evaporated under reduced pressure, and the residue was purified by silica gel chromatography using 10:1 hexane/ethyl acetate as an eluting solvent, to thereby obtain 1.57 g of IMDBT-23.

A flask equipped with a stirrer and a thermometer was charged with 2.85 g of IMDBT-23, 1.21 g of triethylamine, and 28.5 g of tetrahydrofuran in a nitrogen atmosphere, and cooled to 0 to 5° C. 0.94 g of acetyl chloride dissolved in 2.0 g of tetrahydrofuran was added dropwise at the same temperature, and stirred for 30 minutes. After the termination of the reaction, 100 ml of ethyl acetate and 50 ml of water were added for extraction, and the resulting organic phase was separated, washed with water, and vacuum concentrated. The concentrate was purified by silica gel chromatography using 20:1 hexane/ethyl acetate as an eluting solvent, to obtain 2.07 g of IMDBT-24.

A flask equipped with a stirrer and a thermometer was charged with 1.63 g of IMDBT-24, 0.08 g of dichlorobis(triphenylphosphine)palladium, 0.04 g of triphenylphosphine, 0.04 g of copper iodide, 3.67 g of triethylamine, and 16.3 g of dimethylformamide in a nitrogen atmosphere, and heated to 60° C. Then 1.25 g of IM-2 dissolved in 1.2 g of dimethylformamide was added dropwise, stirred at 60 to 65° C. for 14 hours, and cooled to room temperature. 100 ml of ethyl acetate and 100 ml of water were added for extraction, and the resulting organic phase was separated, washed with water, and vacuum concentrated. The concentrate was mixed with 16.7 g of tetrahydrofuran, 16.7 g of methanol, and 0.10 g of p-toluenesulfonic acid, stirred at room temperature for 3 hours, and neutralized with 2 ml of triethylamine to terminate the reaction. The reaction liquid was concentrated, and mixed with 200 ml of ethyl acetate and 100 ml of water for extraction. The resulting organic phase was separated, washed with water, and vacuum concentrated. The concentrate was purified by silica gel chromatography using 5:1 hexane/ethyl acetate mixed with 0.1 wt % triethylamine as an eluting solvent, to thereby obtain 0.94 g of IMDBT-25.

A flask equipped with a stirrer and a thermometer was charged with 2.06 g of IMDBT-25, 0.04 g of 4-pyrrolidinopyridine, 4.12 g of pyridine, and 20.6 g of toluene in a nitrogen atmosphere, and cooled to −2° C. Then 2.26 g of trifluoromethanesulfonic acid anhydride dissolved in 4.5 g of toluene was added dropwise at −2 to 0° C., heated to room temperature, and stirred overnight. 100 ml of ethyl acetate and 50 ml of water were added for extraction, and the resulting organic phase was separated, washed with water, and vacuum concentrated. The concentrate was purified by silica gel chromatography using 1:1 hexane/chloroform as an eluting solvent to obtain 2.51 g of IMDBT-26. The reaction formulae of the series of reactions above are as follows:

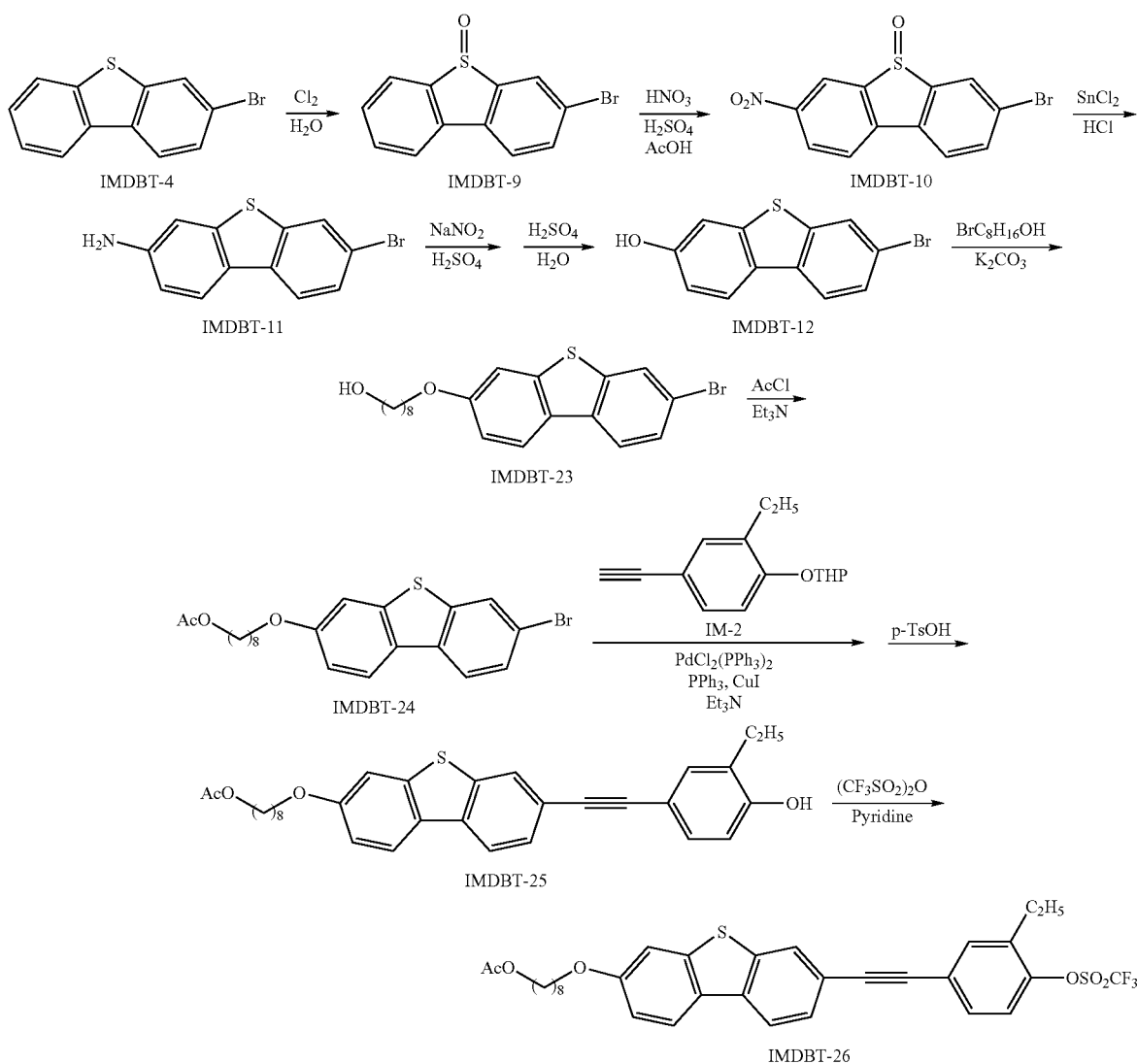

Production Example 3-2

A flask equipped with a stirrer and a thermometer was charged with 2.55 g of IMDBT-12 prepared in Production Example 3-1, 3.16 g of potassium carbonate, 4.14 g of 6-bromohexanol, and 12.8 g of methylethylketone in a nitrogen atmosphere, and heated to 80 to 85° C. The mixture was stirred at the same temperature for 3 hours, cooled to room temperature, and the solvent was evaporated under reduced pressure. The residue was purified by silica gel chromatography using 5:1 hexane/ethyl acetate as an eluting solvent, and recrystallized from ethyl acetate solvent, to thereby obtain 2.20 g of IMDBT-27.

A flask equipped with a stirrer and a thermometer was charged with 2.20 g of IMDBT-27, 0.01 g of p-toluenesulfonic acid, and 66.0 g of chloroform in a nitrogen atmosphere, and cooled to 0 to 5° C. 1.96 g of dihydropyran dissolved in 6.0 g of chloroform was added dropwise at the same temperature, stirred at the same temperature for 1 hour, and neutralized with 0.5 ml of triethylamine to terminate the reaction. The solvent was evaporated under reduced pressure, and the residue was purified by silica gel chromatography using chloroform mixed with 0.1 wt % triethylamine as an eluting solvent, to thereby obtain 2.53 g of IMDBT-28.

A flask equipped with a stirrer and a thermometer was charged with 3.56 g of IMDBT-28, 0.18 g of dichlorobis (triphenylphosphine)palladium, 0.18 g of triphenylphosphine, 0.09 g of copper iodide, 7.77 g of triethylamine, and 35.6 g of dimethylformamide in a nitrogen atmosphere, and heated to 60° C. 1.54 g of trimethylsilylacetylene dissolved in 3.1 g of dimethylformamide was added dropwise, stirred at 60 to 65° C. for 3 hours, and cooled to room temperature. 100 ml of ethyl acetate and 50 ml of water were added for extraction, and the resulting organic phase was separated, washed with water, and vacuum concentrated. 4.37 g of the concentrate was mixed with 26.2 g of tetrahydrofuran, 26.2 g of methanol, and 0.15 g of potassium carbonate, and stirred overnight at room temperature. The reaction liquid was concentrated, and purified by silica gel chromatography using 1:1 hexane/chloroform mixed with 0.1 wt % triethylamine as an eluting solvent, to thereby obtain 2.48 g of IMDBT-29.

A flask equipped with a stirrer and a thermometer was charged with 1.32 g of IMDBT-26 prepared in Production Example 3-1, 0.03 g of dichlorobis(triphenylphosphine) palladium, 0.31 g of triethylamine, and 13.2 g of dimethylformamide in a nitrogen atmosphere, and heated to 60° C. Then 1.32 g of IMDBT-29 dissolved in 4.0 g of dimethylformamide was added dropwise, and stirred at 60 to 65° C. for 10 hours. 100 ml of ethyl acetate and 50 ml of water were added at 50 to 55° C. for extraction, and the resulting organic phase was separated, washed with water, and vacuum concentrated. The concentrate was subjected to silica gel chromatography using 2:3 hexane/chloroform mixed with 0.1 wt % triethylamine as an eluting solvent, and then purified by silica gel chromatography using 2:1 hexane/chloroform mixed with 0.1 wt % triethylamine as an eluting solvent, to thereby obtain 1.10 g of IMDBT-30.

A flask equipped with a stirrer and a thermometer was charged with 2.20 g of IMDBT-30, 0.16 g of p-toluenesulfonic acid, 66.0 g of tetrahydrofuran, 63.0 g of methanol, and 240 g of chloroform in a nitrogen atmosphere, and stirred at room temperature overnight. The mixture was neutralized with 2.0 g of triethylamine to terminate the reaction, vacuum concentrated, subjected to silica gel chromatography using chloroform mixed with 0.1 wt % triethylamine as an eluting solvent, and vacuum concentrated. 1.70 g of the concentrate was introduced into a flask equipped with a stirrer and a thermometer in a nitrogen atmosphere, and dissolved in 204 g of tetrahydrofuran. Then 0.17 g of LiAlH$_4$ was added at room temperature, stirred at room temperature for 3 hours, mixed with 20 g of 5 wt % sodium hydroxide to terminate the reaction, and vacuum concentrated. The concentrate was purified by silica gel chromatography using 5:1 chloroform/ethyl acetate mixed with 0.1 wt % triethylamine to obtain 1.10 g of IMDBT-31. The reaction formulae of the series of reactions above are as follows:

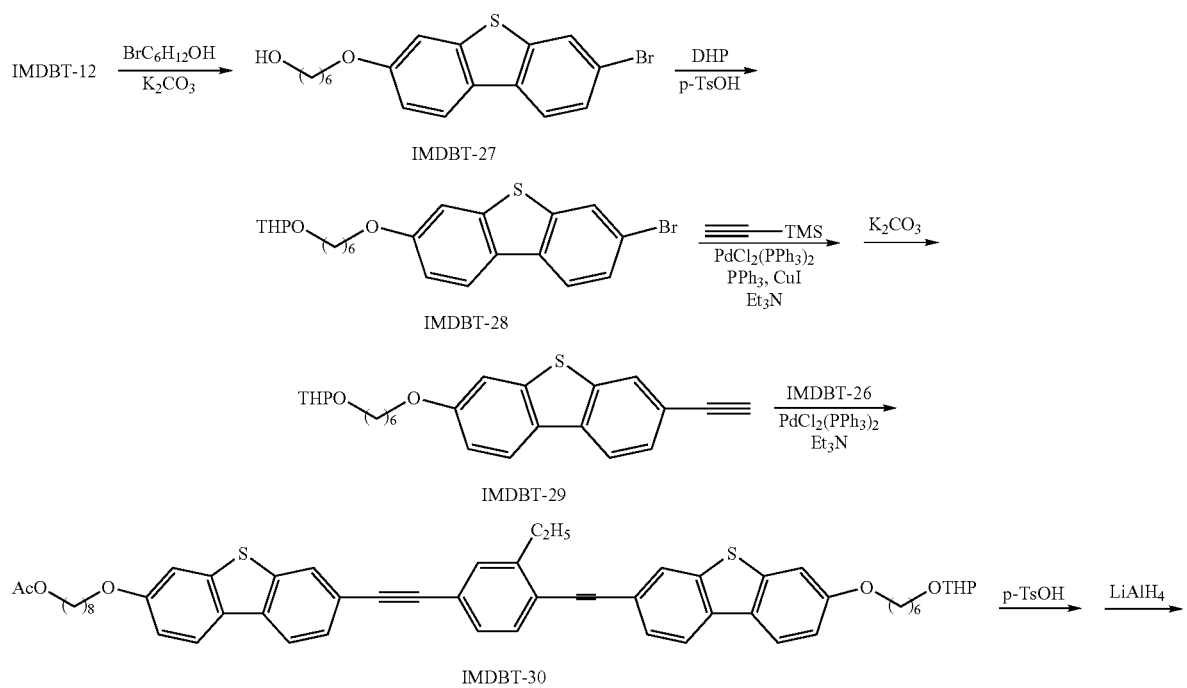

-continued

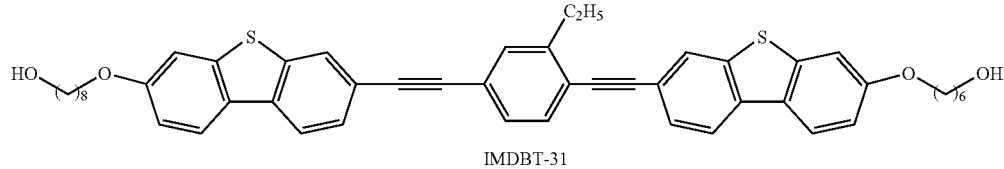

IMDBT-31

Example 3-1

A flask equipped with a stirrer and a thermometer was charged with 0.50 g of IMDBT-31 prepared in Production Example 3-2, 20 g of 1-methyl-2-pyrolidone, and 0.65 g of triethylamine in a nitrogen atmosphere, and stirred at room temperature. Then 0.34 g of acrylic acid chloride dissolved in 10 g of chloroform was added dropwise, and stirred at room temperature for 4 hours. When the starting materials were confirmed by TLC to have been disappeared, 100 ml of ethyl acetate and 100 ml of water were added for extraction. The organic phase was concentrated, and the resulting solid was purified by silica gel chromatography using 2:1 hexane/chloroform mixed with 0.1 wt % triethylamine as an eluting solvent, to thereby obtain 0.39 g of the objective compound DBT1124. The $^1$H-NMR spectrum data of the resulting DBT1124, as well as the formulae of the reaction above are shown below.

$^1$H-NMR(CDCl$_3$, δ): 1.17–1.82(m,23H),2.86(q,2H,J=7.5 Hz), 3.96(t,2H,J=6.5 Hz),3.97(t,2H,J=6.4 Hz),4.08(t,2H, J=6.8 Hz), 4.10(t,2H,J=6.7 Hz),5.73(d,2H,J=9.4 Hz),6.05 (dd,2H, J=17.2 Hz,9.4 Hz),6.33(d,2H,J=17.2 Hz),6.94–6.98 (m,2H), 7.28–7.62(m,7H),7.87–7.93(m,6H)

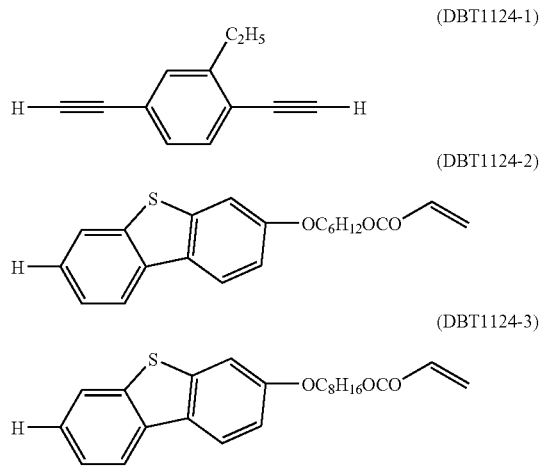

The phase sequence of the compound DBT1124 was evaluated with polarization microscope to find that the compound was in the crystalline phase below 124° C., in the nematic phase from 124° C. to at least 300° C., and in the isotropic phase above 253° C. It was thus demonstrated that this compound is a crystalline compound.

10 wt % of the compound DBT1124 was added to a nematic composition MJ931381 (manufactured by Merck Japan Co.) and the refractive index anisotropy Δn was determined, from which Δn of the compound was extrapolated based on the concentration. It was determined that the

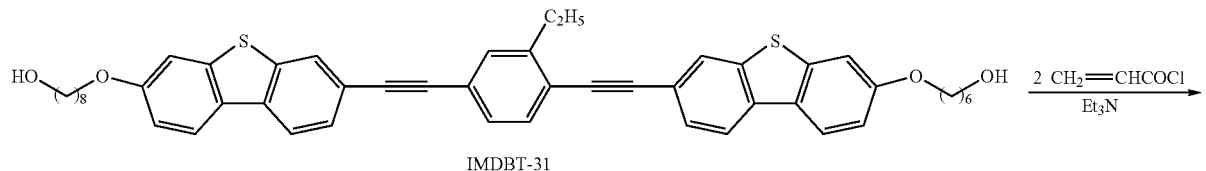

IMDBT-31

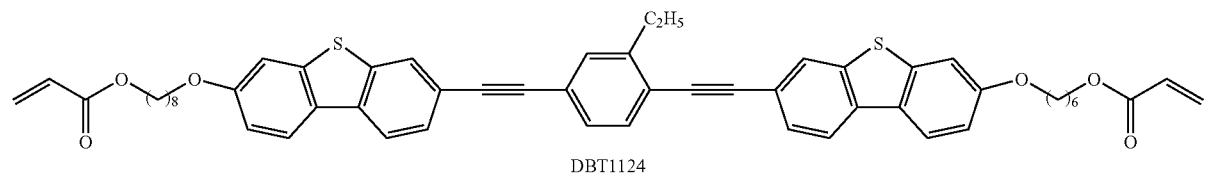

DBT1124

The obtained DBT1124 was theoretically divided into the following parts, and the difference ΔE in energy of HOMO of the parts and the polarizability anisotropy Δα were calculated by the method of molecular orbitals. The results are as follows:

$$\Delta E = |E_{DBT1124\text{-}1} - (E_{DBT1124\text{-}2} + E_{DBT1124\text{-}3})/2| = 0.74 \text{ (eV)}$$

$$\Delta \alpha = 976 \text{ (atomic units)}$$

Δn of the compound was 0.41, which is an extremely large value. Δn was measured with an Abbe refractometer at 20° C. and at the wavelength of 589 nm.

Example 3-2. It was found that the refractive index anisotropy was 0.384 (632.8 nm) at 20° C., which is an extremely large value.

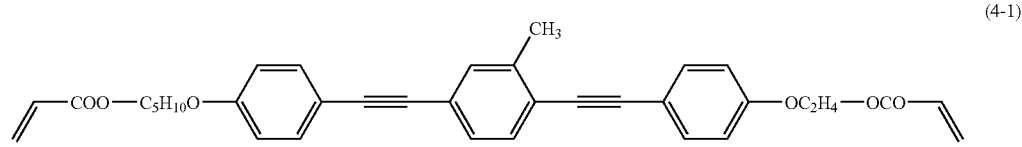

(4-1)

Example 3-2

DBT1124 prepared in Example 3-1 was mixed with 3 wt % of a photopolymerization initiator (trade name "IRGACURE 651" manufactured by CIBA GEIGY AG), and the resulting mixture was injected into a transparent glass cell having a cell gap of about 8 μm. The transparent glass cell had been fabricated by forming polyimide thin films on the surfaces of two glass substrates, rubbing the surfaces, and arranging the two substrates with the directions of rubbing being parallel to each other. The glass cell was irradiated with a light from a high-pressure mercury lamp at 1600 mJ/cm² at 125° C. to polymerize the liquid crystalline monomer in the cell. Through polarization microscopic observation of the cell, it was confirmed that an optically anisotropic product had been obtained wherein the nematic alignment had been uniformly fixed.

Next, the same liquid crystalline material containing the photopolymerization initiator was injected into a cell composed of two glass substrates that had been treated for alignment in the same manner as above and arranged in the form of a wedge of about 1.6 degree, and polymerized under the same conditions as above. The cell thus fabricated was measured for the refractive index anisotropy using helium-neon laser in accordance with the method described in *Handbook of Liquid Crystals*, Vol. 2A, p129 (ed. by D. Demus, J. Goodby, G. W. Dray, H. W. Spiess, and V. Vill, WILEY-VCH-Verlag). It was found that the refractive index anisotropy was 0.35 at 20° C., which is an extremely large value.

Example 3-3

Liquid crystal composition M-3 was prepared by mixing 65.7 wt % of DBT1124 prepared in Example 3-1 and 34.3 wt % of the compound represented by the formula (4-1) as a compound represented by the formula (4). The obtained liquid crystal composition M-3 was mixed with 3 wt % of a photopolymerization initiator (trade name "IRGACURE 651" manufactured by CIBA GEIGY AG), and the resulting mixture was injected into a transparent glass cell in the same manner as in Example 3-2, and polymerized. Through polarization microscopic observation of the cell, it was confirmed that an optically anisotropic product had been obtained wherein the nematic alignment had been uniformly fixed.

Further, the refractive index anisotropy of the same liquid crystalline material was measured in the same manner as in Example 3-2. It was found that the refractive index anisotropy was 0.384 (632.8 nm) at 20° C., which is an extremely large value.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dibenzothiophene oxide compound represented by the formula (A-3):

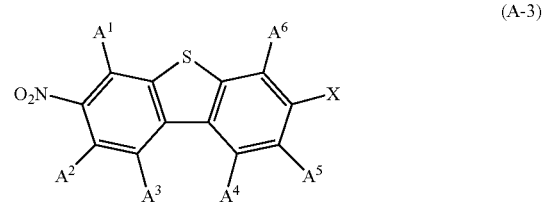

(A-3)

wherein $A^1$ to $A^6$ each independently stands for a hydrogen atom, a fluorine atom, an alkyl or alkoxy group having 1 to 10 carbon atoms optionally substituted with at least one fluorine atom, and X stands for a halogen atom.

2. A dibenzothiophene oxide compound represented by the formula (A-4):

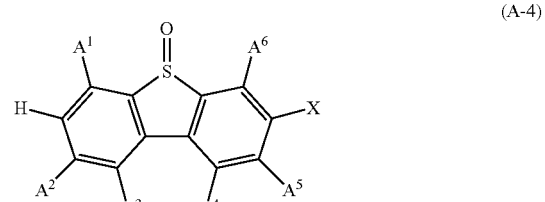

(A-4)

wherein $A^1$ to $A^6$ each independently stands for a hydrogen atom, a fluorine atom, an alkyl or alkoxy group having 1 to 10 carbon atoms optionally substituted with at least one fluorine atom, and X stands for a halogen atom.

3. A method for producing the dibenzothiophene oxide compound of claim 1 comprising reacting a dibenzothiophene oxide compound represented by the formula (A-4):

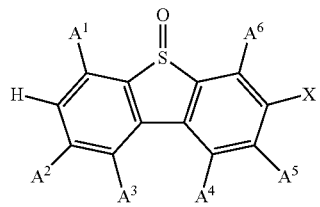

(A-4)

wherein $A^1$ to $A^6$ each independently stands for a hydrogen atom, a fluorine atom, an alkyl or alkoxy group having 1 to 10 carbon atoms optionally substituted with at least one fluorine atom, and X stands for a halogen atom, with a nitrating agent selected from the group consisting of nitrates of sodium, potassium, or silver; nitrites of sodium, potassium, or silver; alkyl nitrates; and nitric acid.

4. A method for producing the dibenzothiophene oxide compound of claim 2 comprising reacting a dibenzothiophene compound represented by the formula (A-5):

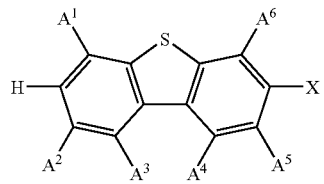

(A-5)

wherein $A^1$ to $A^6$ each independently stands for a hydrogen atom, a fluorine atom, an alkyl or alkoxy group having 1 to 10 carbon atoms optionally substituted with at least one fluorine atom, and X stands for a halogen atom, with an oxidizing agent selected from the group consisting of organic peroxides, perhalides, a mixture of chlorine and water, and hydrogen peroxide.

5. The method of claim 3, wherein said alkyl nitrates comprise butyl or amyl nitrate.

6. The method of claim 3, wherein the amount of said nitrating agent in 1 to 100 times the amount of dibenzothiophene oxide compound (A-4) in mole.

7. The method of claim 3, wherein said reacting is performed at −50 to 200° C.

8. The method of claim 4, wherein the amount of said oxidizing agent is 1 to 100 times the amount of dibenzothiophene compound (A-5) in mole.

9. The method of claim 4, wherein said reacting is performed at −50 to 200° C.

* * * * *